(12) United States Patent
Saltzman et al.

(10) Patent No.: US 9,272,043 B2
(45) Date of Patent: Mar. 1, 2016

(54) ENZYMATIC SYNTHESIS OF POLY(AMINE-CO-ESTERS) AND METHODS OF USE THEREOF FOR GENE DELIVERY

(71) Applicant: Yale University, New Haven, CT (US)

(72) Inventors: W. Mark Saltzman, New Haven, CT (US); Zhaozhong Jiang, New Haven, CT (US); Jiangbing Zhou, Cheshire, CT (US); Jie Liu, Guangdong (CN)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/293,733

(22) Filed: Jun. 2, 2014

(65) Prior Publication Data
US 2014/0342003 A1    Nov. 20, 2014

Related U.S. Application Data

(63) Continuation-in-part of application No. PCT/US2012/067447, filed on Nov. 30, 2012.

(60) Provisional application No. 61/566,412, filed on Dec. 2, 2011, provisional application No. 61/870,497, filed on Aug. 27, 2013.

(51) Int. Cl.
| | |
|---|---|
| *A61K 9/50* | (2006.01) |
| *A61K 9/14* | (2006.01) |
| *C08G 63/685* | (2006.01) |
| *C12N 15/87* | (2006.01) |
| *A61K 47/34* | (2006.01) |
| *A61K 31/7088* | (2006.01) |
| *A61K 9/107* | (2006.01) |

(52) U.S. Cl.
CPC .............. *A61K 47/34* (2013.01); *A61K 9/1075* (2013.01); *A61K 31/7088* (2013.01); *C08G 63/6852* (2013.01); *C12N 15/87* (2013.01)

(58) Field of Classification Search
CPC . A61K 31/7088; A61K 47/34; A61K 9/1075; A61K 47/482; A61K 9/5146; C08G 63/6852; C12N 15/87
USPC ............ 514/1.1, 44 A, 44 R, 772.7; 424/490, 424/501, 93.7; 435/375, 459
See application file for complete search history.

(56) References Cited

U.S. PATENT DOCUMENTS

2008/0166382 A1    7/2008  Hsieh

FOREIGN PATENT DOCUMENTS

| FR | 2873570 | 2/2006 |
|---|---|---|
| WO | 2004073617 | 9/2004 |

OTHER PUBLICATIONS

Liu, rt al., "Enzyme-synthesized poly(amine-co-esters) as nonviral vectors for gene delivery", J Biornedmater Res A, 96A(2):456-65 (2011).
Liu, et al., "Poly(omega-pentadecalactone-co-butylene-co-succinate) nanoparticles as biodegradable carriers for camptothecin delivery", Biomaterials, 30:5707-19 (2009).
Wang, et al., "Synthesis and characterization of cationic micelles self-assembled from a biodegradable copolymer for gene delivery", Biomacromolecules, 8:1028-37 (2008).
Zhou, et al., "Biodegradable poly(amine-co-ester) terpolymers for targeted gene deliver", Nat Mater., 11(1):82-90 (2012).

*Primary Examiner* — Janet Epps-Smith
(74) *Attorney, Agent, or Firm* — Pabst Patent Group LLP

(57) ABSTRACT

Poly(amine-co-ester) polymers, methods of forming active agent-load nanoparticles therefrom, and methods of using the nanoparticles for drug delivery are disclosed. The nanoparticles can be coated with an agent that reduces surface charge, an agent that increases cell-specific targeting, or a combination thereof. Typically, the loaded nanoparticles are less toxic, more efficient at drug delivery, or a combination thereof compared to a control other transfection reagents. In some embodiments, the nanoparticles are suitable for in vivo delivery, and can be administered systemically to a subject to treat a disease or condition.

44 Claims, 17 Drawing Sheets

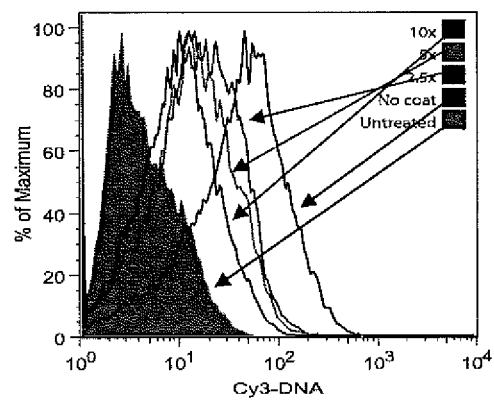
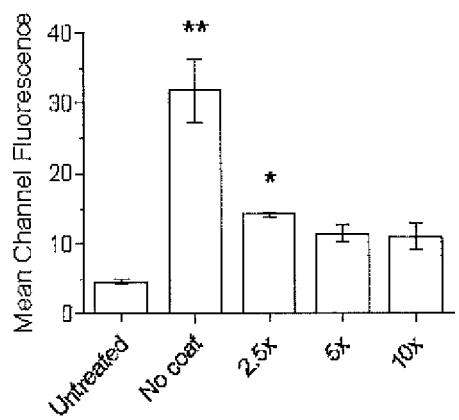
Figure 9
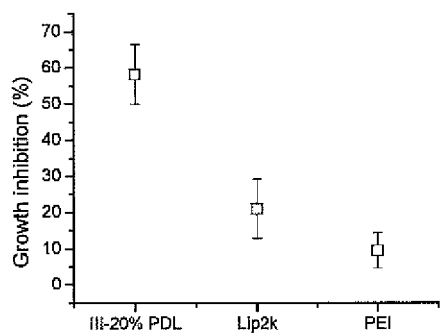
Figure 10

Figures 23A-C

ENZYMATIC SYNTHESIS OF POLY(AMINE-CO-ESTERS) AND METHODS OF USE THEREOF FOR GENE DELIVERY

CROSS-REFERENCE TO RELATED APPLICATIONS

This application claims priority to International Patent Application No. PCT/US2012/067447 entitled "Enzymatic Synthesis of Novel poly(amine-co-esters) and Methods of use Thereof for Gene Delivery", filed Nov. 30, 2012, which claims priority to U.S. Provisional Application No. 61/566,412 entitled "Enzymatic Synthesis of Novel poly(amine-co-esters) and Their Use as Highly Efficient Non-viral Vectors for Gene Delivery" filed Dec. 2, 2011. This application also claims priority to U.S. Provisional Application No. 61/870,497 entitled "Enzymatic Synthesis of Novel poly(amine-co-esters) and Methods of use Thereof for Gene Delivery". Where permissible, these applications are incorporated by reference in their entirety.

REFERENCE TO SEQUENCE LISTING

The Sequence Listing submitted on Aug. 8, 2014 as a text file named "YU_5543_ST25.txt," created on Aug. 5, 2014, and having a size of 2,819 bytes is hereby incorporated by reference pursuant to 37 C.F.R. §1.52(e)(5).

STATEMENT REGARDING FEDERALLY SPONSORED RESEARCH OR DEVELOPMENT

This invention was made with Government Support under Agreement R56 EB000487 awarded by the National Institutes of Health. The Government has certain rights in the invention.

FIELD OF THE INVENTION

The field of the invention is generally related to novel polymer compositions and methods for improved systemic delivery of nucleic acids in vivo.

BACKGROUND OF THE INVENTION

Non-viral vectors for gene delivery have attracted much attention in the past several decades due to their potential for limited immunogenicity, ability to accommodate and deliver large size genetic materials, and potential for modification of their surface structures. Major categories of non-viral vectors include cationic lipids and cationic polymers. Cationic lipid-derived vectors, which were pioneered by Felgner and colleagues, represent some of the most extensively investigated systems for non-viral gene delivery (Felgner, et al. Lipofection: a highly efficient, lipid-mediated DNA-transfection procedure. *PNAS*, 84, 7413-7417 (1987)) (Templeton, et al. Improved DNA: liposome complexes for increased systemic delivery and gene expression. *Nat. Biotechnol.* 15, 647-652 (1997)) (Chen, et al. Targeted nanoparticles deliver siRNA to melanoma. *J. Invest. Dermatol.* 130, 2790-2798 (2010)).

Cationic polymer non-viral vectors have gained increasing attention because of flexibility in their synthesis and structural modifications for specific biomedical applications. Both cationic lipid and cationic polymer systems deliver genes by forming condensed complexes with negatively charged DNA through electrostatic interactions: complex formation protects DNA from degradation and facilitates its cellular uptake and intracellular traffic into the nucleus.

Polyplexes formed between cationic polymers and DNA are generally more stable than lipoplexes formed between cationic lipids and DNA, but both are often unstable in physiological fluids, which contain serum components and salts, and tend to cause the complexes to break apart or aggregate (Al-Dosari, et al. Nonviral gene delivery: principle, limitations, and recent progress. *AAPS J.* 11, 671-681 (2009)) (Tros de Ilarduya, et al. Gene delivery by lipoplexes and polyplexes. *Eur. J. Pharm. Sci.* 40, 159-170 (2010)). Additionally, although some work indicates that anionic polymers or even naked DNA can provide some level of transfection under certain conditions, transfection by both lipids and polymers usually requires materials with excess charge, resulting in polyplexes or lipoplexes with net positive charges on the surface (Nicol, et al. Poly-L-glutamate, an anionic polymer, enhances transgene expression for plasmids delivered by intramuscular injection with in vivo electroporation. *Gene. Ther.* 9, 1351-1358 (2002)) (Schlegel, et al. Anionic polymers for decreased toxicity and enhanced in vivo delivery of siRNA complexed with cationic liposomes. *J. Contr. Rel.* 152, 393-401 (2011)) (Liu, et al, Nonviral gene delivery: What we know and what is next. *AAPS J.* 9, E92-E104 (2007)) (Liu, et al. Hydrodynamics-based transfection in animals by systemic administration of plasmid DNA. *Gene Ther.* 6, 1258-1266 (1999)). When injected into the circulatory system in vivo, the positive surface charge initiates rapid formation of complex aggregates with negatively charged serum molecules or membranes of cellular components, which are then cleared by the reticuloendothelial system (RES).

More importantly, many cationic vectors developed so far exhibit substantial toxicity, which has limited their clinical applicability (Tros de Ilarduya, et al. Gene delivery by lipoplexes and polyplexes. *Eur. J. Pharm. Sci.* 40, 159-170 (2010)) (Gao, et al. The association of autophagy with polyethylenimine-induced cytotoxicity in nephritic and hepatic cell lines. *Biomaterials* 32, 8613-8625 (2011)) (Felgner, et al. Enhanced gene delivery and mechanism studies with a novel series of cationic lipid formulations. *J. Biol. Chem.* 269, 2550-2561 (1994)) (Kafil, et al. Cytotoxic Impacts of Linear and Branched Polyethylenimine Nanostructures in A431 Cells. *BioImpacts* 1, 23-30 (2011)) (Lv, et al. Toxicity of cationic lipids and cationic polymers in gene delivery. *J Contr. Rel.* 114, 100-109 (2006)). This too appears to depend on charge: excess positive charges on the surface of the complexes can interact with cellular components, such as cell membranes, and inhibit normal cellular processes, such as clathrin-mediated endocytosis, activity of ion channels, membrane receptors, and enzymes or cell survival signaling (Gao, et al. The association of autophagy with polyethylenimine-induced cytotoxicity in nephritic and hepatic cell lines. *Biomaterials* 32, 8613-8625 (2011)) (Felgner, et al. Enhanced gene delivery and mechanism studies with a novel series of cationic lipid formulations. *J. Biol. Chem.* 269, 2550-2561 (1994)) (Kafil, et al. Cytotoxic Impacts of Linear and Branched Polyethylenimine Nanostructures in A431 Cells. *BioImpacts* 1, 23-30 (2011)).

As a result, cationic lipids often cause acute inflammatory responses in animals and humans, whereas cationic polymers, such as PEI, destabilize the plasma-membrane of red blood cells and induce cell necrosis, apoptosis and autophagy (Tros de Ilarduya, et al. Gene delivery by lipoplexes and polyplexes. *Eur. J. Pharm. Sci.* 40, 159-170 (2010)) (Gao, et al. The association of autophagy with polyethylenimine-induced cytotoxicity in nephritic and hepatic cell lines. *Biomaterials* 32, 8613-8625 (2011)) (Lv, et al. Toxicity of cationic lipids and cationic polymers in gene delivery. *J. Contr. Rel.*

114, 100-109 (2006)). Because of these undesirable effects, there is a need for highly efficient non-viral vectors that have lower charge densities.

Synthesis of a family of biodegradable poly(amine-co-esters) formed via enzymatic copolymerization of diesters with amino-substituted diols is discussed in Liu, et al. Enzyme-synthesized poly(amine-co-esters) as nonviral vectors for gene delivery. *J. Biomed. Mater. Res. A* 96A, 456-465 (2011) and Jiang, Z. Lipase-catalyzed synthesis of poly (amine-co-esters) via copolymerization of diester with amino-substituted diol. *Biomacromolecules* 11, 1089-1093 (2010).

Diesters with various chain length (e.g., from succinate to dodecanedioate) were copolymerized with diethanolamines with either an alkyl (methyl, ethyl, n-butyl, t-butyl) or an aryl (phenyl) substituent on the nitrogen. The high tolerance of the lipase catalyst allowed the copolymerization reactions to complete in one step without protection and deprotection of the amino functional groups. Upon protonation at slightly acidic conditions, these poly(amine-co-esters) readily condense DNA and form nano-sized polyplexes. Screening studies revealed that one of these materials, poly(N-methyldiethyleneamine sebacate) (PMSC), transfected a variety of cells including HEK293, U87-MG, and 9L, with efficiency comparable to that of leading commercial products, such as Lipofectamine 2000 and PEI14. PMSC had been previously used for gene delivery, but the delivery efficiency of the enzymatically synthesized materials was approximately five orders of magnitude higher than any previously reported (Wang, et al. Synthesis and characterization of cationic micelles self-assembled from a biodegradable copolymer for gene delivery. *Biomacromolecules* 8, 1028-1037 (2007)) (Wang, et al. The self-assembly of biodegradable cationic polymer micelles as vectors for gene transfection. *Biomaterials* 28, 5358-5368 (2007)). However, these poly(amine-co-esters) were not effective for systemic delivery of nucleic acids in vivo. This may be due to the fact that the polyplexes formed by these polymers and genetic materials (1) do not have sufficient efficiency for in vivo applications and/or (2) are not stable enough in the blood and fall apart or aggregate during circulation.

Accordingly, there remains a need for non-viral vectors suitable for efficient systemic, in vivo delivery of nucleic acids with low toxicity.

There is also a need for polymeric nanocarriers which can be prepared in as few steps as possible and in which the molecular weight and/or polymer composition can be easily controlled.

Therefore, it is an object of the invention to provide improved polymers which can effectively deliver therapeutic, diagnostic, and/or prophylactic agents in vivo, and methods of making and using thereof.

It is an object of the invention to provide improved polymers which can effectively deliver genetic materials to cells in high efficiency in vitro and are suitable for in vivo delivery of nucleic acids, and methods of making thereof.

It is also an object of the invention to provide methods of using improved polymers for systemic delivery of nucleic acids in vivo.

SUMMARY OF THE INVENTION

Polymers with improved properties for delivering therapeutic, diagnostic, and/or prophylactic agents are described.

Polymers having the formula below are disclosed.

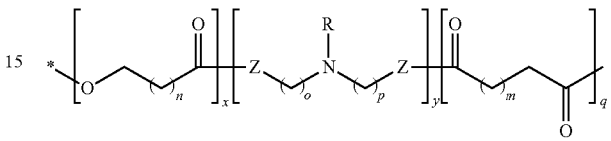

Formula I wherein each occurrence of n is an integer from 1-30, each occurrence of m, o, and p is independently an integer from 1-20, and each occurrence of x, y, and q is independently an integer from 1-1000, and Z is O or NR', wherein R' is hydrogen, substituted or unsubstituted alkyl, or substituted or unsubstituted aryl.

In some embodiments, Z is O.

In some embodiments, Z is O and n is an integer from 1-16, such as 4, 10, 13, or 14.

In some embodiments, Z is O, n is an integer from 1-16, such as 4, 10, 13, or 14, and m is an integer from 1-10, such as 4, 5, 6, 7, or 8.

In some embodiments, Z is O, n is an integer from 1-16, such as 4, 10, 13, or 14, m is an integer from 1-10, such as 4, 5, 6, 7, or 8, and o and p are the same integer from 1-6, such as 2, 3, or 4.

In some embodiments, Z is O, n is an integer from 1-16, such as 4, 10, 13, or 14, m is an integer from 1-10, such as 4, 5, 6, 7, or 8, and R is alkyl, such a methyl, ethyl, n-propyl, isopropyl, n-butyl, or t-butyl, or aryl, such as phenyl.

In certain embodiments, n is 14 (e.g., pentadecalactone, PDL), m is 7 (e.g., diethylsebacate, DES), o and p are 2 (e.g., N-methyldiethanolamine, MDEA). In certain embodiments, n, m, o, and p are as defined above, and PEG is incorporated as a monomer.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees.

The polymers can further include a block of an alkylene oxide, such as polyethylene oxide, polypropylene oxide, and/or polyethylene oxide-co-polypropylene oxide. The structure of a PEG-containing diblock polymer is shown below:

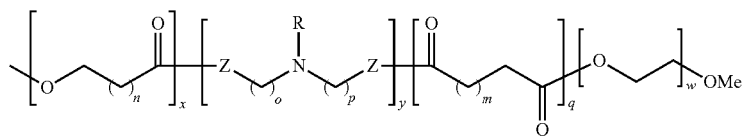

wherein n is an integer from 1-30, m, o, and p are independently an integer from 1-20, x, y, q, and w are independently integers from 1-1000, and Z is O or NR', wherein R' is hydrogen, substituted or unsubstituted alkyl, or substituted or unsubstituted aryl. In particular embodiments, the values of x, y, q, and w are such that the weight average molecular weight of the polymer is greater than 20,000 Daltons.

The structure of a PEG-containing triblock copolymer is shown below:

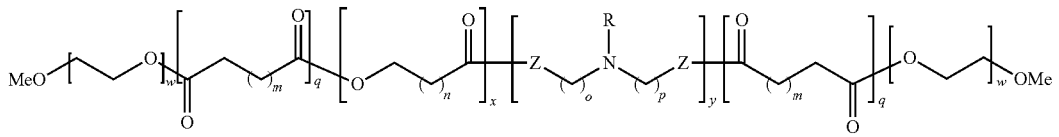

wherein n is an integer from 1-30, m, o, and p are independently an integer from 1-20, x, y, q, and w are independently integers from 1-1000, and Z is O or NR', wherein R' is hydrogen, substituted or unsubstituted alkyl, or substituted or unsubstituted aryl. In particular embodiments, the values of x, y, q, and w are such that the weight average molecular weight of the polymer is greater than 20,000 Daltons.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof.

In particular embodiments, the values of x, y, q, and/or w are such that the weight average molecular weight of the polymer is greater than 20,000 Daltons.

The polymer can prepared from one or more lactones, one or more amine-diols (Z=O) or triamines (Z=NR'), and one or more diacids or diesters. In those embodiments where two or more different lactone, diacid or diester, and/or triamine or amine-diol monomers are used, than the values of n, o, p, and/or m can be the same or different.

The monomers show above can be unsubstituted or can be substituted. "Substituted", as used herein, means one or more atoms or groups of atoms on the monomer has been replaced with one or more atoms or groups of atoms which are different than the atom or group of atoms being replaced. In some embodiments, the one or more hydrogens on the monomer is replaced with one or more atoms or groups of atoms. Examples of functional groups which can replace hydrogen are listed above in the definition. In some embodiments, one or more functional groups can be added which vary the chemical and/or physical property of the resulting monomer/polymer, such as charge or hydrophilicity/hydrophobicity, etc. Exemplary substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymers can be used to form micro- and/or nanoparticles having encapsulated therein therapeutic, diagnostic, and/or prophylactic agent. The agent to be encapsulated and delivered can be a small molecule agent (i.e., non-polymeric agent having a molecular weight less than 2,000, 1500, 1,000, 750, or 500 Dalton) or a macromolecule (e.g., an oligomer or polymer) such as proteins, enzymes, peptides, nucleic acids, etc. The particles can be used for in vivo and/or in vitro delivery of the agent.

The particles prepared from the polymers can be coated with surface charge altering materials, such as polypeptides, that increase stability and half-life of the particles in systemic circulation. The charge altering material can include a targeting moiety that increases targeting of the particles to a cell type or cell state of interest.

In some embodiments, the particles have a mean particle size from about 100 nm to about 300 nm, preferably from about 150 nm to about 275 nm. In some embodiments, the weight:weight ratio of polymer:polynucleotide is between about 25:1 and 250:1.

In some embodiments, the polymers can be used to form polymeric nanoparticulate polynucleotide carriers, referred to herein as polyplexes, which are effective for delivering the polynucleotides to cells in vitro and in vivo. The polyplexes have improved efficacy or reduced toxicity in vivo compared to other polynucleotide delivery approaches, enabling the polyplexes to be utilized in a broad range of therapeutic applications, for example, gene therapy. Typically, the polyplexes are less toxic and more efficient at transfecting polynucleotides when compared to a control, such as LIPOFECTAMINE 2000 or polyethylenimine (PEI). In some embodiments, the polyplexes are suitable for in vivo transfection, and can be used when other transfection reagents are too toxic or too inefficient to support in vivo applications. In some embodiments, the in vivo application includes systemic administration of the polyplexes.

The polyplexes can be coated with one or more agents that reduce the surface charge of the polyplex at physiological pH. The coating can impart a neutral or negative surface charge to the polyplex. The agent can include, for example, a polypeptide with a series of negatively charged amino acids, such as glutamic acids or aspartic acids. In some embodiments, the polypeptide includes a cell targeting signal or cell targeting domain that enhances targeting of the polyplexes to a specific cell-type or cell-state. For example, the cell targeting domain can enhance targeting of the polyplexes to cancer cells. Exemplary cell targeting domains include RGD, R/KxxR/K where "x" is any amino acid, GdPdLGdVdRG (SEQ ID NO:5), and ASGPR (SEQ ID NO:6). In some embodiments, the stretch of negatively charged amino acids and the cell targeting domain are linked by a linker polypeptide. The linker can be a series of glycines. An exemplary coating including an agent that reduces surface charge and provides cell specific targeting to cancer cells is EEEEEEEEEEEEEEEEGGGGGGRGDK (SEQ ID NO:1).

The polynucleotide can include a sequence that encodes a protein, a sequence that encodes a functional nucleic acid, or can itself be a functional nucleic acid, rRNA, or tRNA. Functional nucleic acids include, but are not limited to, antisense molecules, siRNA, miRNA, aptamers, ribozymes, triplex forming molecules, RNAi, and external guide sequences. In some embodiments, the polynucleotide includes an expression control sequence operably linked to a sequence encoding a protein, functional nucleic acid, rRNA, or tRNA. For example, the polynucleotide can be an expression vector.

Compositions, such as pharmaceutical compositions, containing the particles are also disclosed. The particles can be contacted with cells to transfect the agent, such as a polynucleotide, into the cells. In some embodiments, the contacting occurs in vivo by administering the particles, or a pharmaceutical composition containing the particles, to a subject in an effective amount to treat a disease or condition. The disease or condition can be, for example, a mitochondrial disease, an infectious disease, a cancer, a metabolic disorder, an autoimmune disease, an inflammatory disorder, or an age-related disorder. The particles can be administered parenterally, transdermally, or transmucosally. The particles can be administered systemically or locally.

In some embodiments, contacting the cells with polyplexes to transfect the polynucleotide occurs in vitro, or ex vivo. The cells can be primary cells or cells from a cell line. The primary cells can be harvested from a subject. In some embodiments, the transfected cells are administered back to the subject, or to a different subject as part of a cell-based therapy for treating a disease or condition.

BRIEF DESCRIPTION OF THE DRAWINGS

FIG. 9 is a histogram (top panel) and a bar graph (bottom panel) showing cell internalization of III-20% PDL/Cy3-DNA polyplexes as monitored using flow cytometry. For the bar graph, n=3, **p<0.005, *p<0.05 using student's t-test with respect to polyplex with 10× coat.

FIG. 10 is a dot plot showing the toxicity of III-20% PDL/TRAIL, Lip2k/TRAIL and PEI/TRAIL complexes (growth inhibition %) on A549 tumor cells. Toxicity was determined five days after treatment by standard MTT assay.

(FIG. 19A) PBS with pH of 7.4, (FIG. 19B) PBS with pH of 5.0.

(FIG. 23A) blank micelles (medium pH: 7.4), (FIG. 23B) DTX-loaded micelles of the copolymers with different PDL contents (medium pH: 7.4), and (FIG. 23C) DTX-loaded micelles of the copolymer with 11% PDL (medium pH: 7.4 or 6.5). Data are given as mean±SD (n=3). *$p<0.05$ and **$p<0.01$ compared with PEG2K-PPMS-11% PDL copolymer sample.

DETAILED DESCRIPTION OF THE INVENTION

I. Definitions

Figure 1:
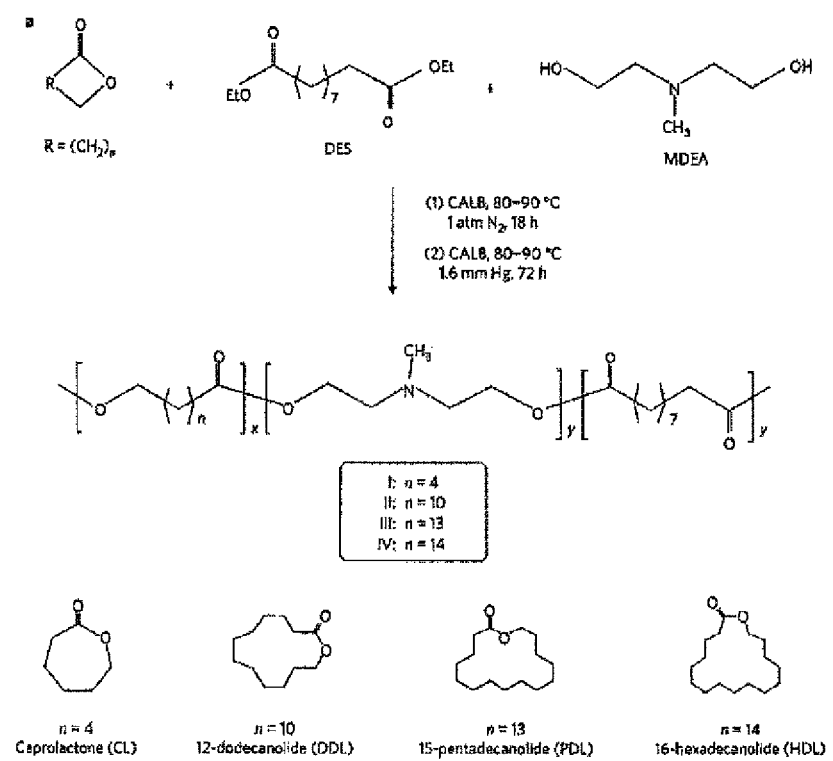
FIG. 1 is a scheme showing a two-stage process for the preparation of terpolymers from a lactone, DES, and MDEA.

The term "polyplex" as used herein refers to polymeric micro- and/or nanoparticles or micelles having encapsulated therein, dispersed within, and/or associated with the surface of, one or more polynucleotides.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Sustained release" as used herein refers to release of a substance over an extended period of time in contrast to a bolus type administration in which the entire amount of the substance is made biologically available at one time.

The term "microspheres" is art-recognized, and includes substantially spherical colloidal structures, e.g., formed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron (1000 nm) in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm. In some embodiments, the average diameter of the particles is from about 200 nm to about 600 nm, preferably from about 200 to about 500 nm. Microparticles can be used for gene therapy, particularly for vaccinations.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10%, 8%, 5%, 3%, or 2% of the median volume diameter.

The term "particle" as used herein refers to any particle formed of, having attached thereon or thereto, or incorporating a therapeutic, diagnostic or prophylactic agent, optionally including one or more polymers, liposomes micelles, or other structural material. A particle may be spherical or nonspherical. A particle may be used, for example, for diagnosing a disease or condition, treating a disease or condition, or preventing a disease or condition.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "surfactant" as used herein refers to an agent that lowers the surface tension of a liquid.

The term "targeting moiety" as used herein refers to a moiety that localizes to or away from a specific locale. The moiety may be, for example, a protein, nucleic acid, nucleic acid analog, carbohydrate, or small molecule, Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thenoimidazolyl, thiophenyl and xanthenyl. One or more of the rings can be substituted as defined above for "aryl".

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA*, 81:2035-39 (1984), or from another source, binds with high specificity, as described by Chamberlin, et al., *Nature*, 228:227-231 (1970).

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

The term "construct" refers to a recombinant genetic molecule having one or more isolated polynucleotide sequences.

The term "expression control sequence" refers to a nucleic acid sequence that controls and regulates the transcription and/or translation of another nucleic acid sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein "to reprogram a cell" or "cellular reprogramming" means to induce a cell to express one or more polypeptides or functional nucleic acids in an effective amount to change a function of the cell. The function can be any function. For example, an immune cell can be induced to express a receptor which changes the cell's ability to recognize an antigen or to mediate an immune response; or a somatic cell can be induced to express a pluripopency marker(s) which can dedifferentiate the cell from a somatic state to a pluripotent state (i.e., induced pluripotent stem cell (iPS)).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, 3$^{rd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli, Thermus thermophilus,* and *Bacillus stearothermophilus,* or organisms of the Archaea phylogenetic domain such as, *Methanocaldococcus jannaschii, Methanothermobacter thermautotrophicus, Halobacterium* such as *Haloferax volcanii* and *Halobacterium* species NRC-1, *Archaeoglobus fulgidus, Pyrococcus furiosus, Pyrococcus horikoshii,* and *Aeuropyrum pernix.*

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter the characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences.

"Transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a cell, bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction $W/Z$, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "purified" and like terms relate to the isolation of a molecule or compound in a form that is substantially free (at least 60% free, preferably 75% free, and most preferably 90% free) from other components normally associated with the molecule or compound in a native environment.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

II. Polymers

Poly(amine-co-ester)s or poly(amine-co-amides) are described herein. In one embodiment, the polymer has the formula:

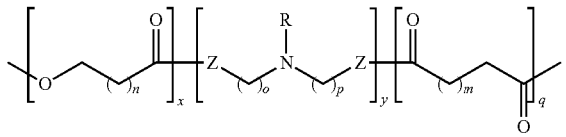

Formula I wherein n is an integer from 1-30, m, o, and p are independently an integer from 1-20, x, y, and q are independently integers from 1-1000, and Z is O or NR', wherein R' is hydrogen, substituted or unsubstituted alkyl, or substituted or unsubstituted aryl. In particular embodiments, the values of x, y, and q are such that the weight average molecular weight of the polymer is greater than 20,000 Daltons. The polymer can prepared from one or more lactones, one or more amine-diols or triamines, and one or more diacids or diesters. In those embodiments where two or more different lactone, diacid or diester, and/or triamine or amine-diol monomers are used, than the values of n, o, p, and/or m can be the same or different.

In some embodiments, Z is O.

In some embodiments, Z is O and n is an integer from 1-16, such 4, 10, 13, or 14.

In some embodiments, Z is O, n is an integer from 1-16, such 4, 10, 13, or 14, and m is an integer from 1-10, such as 4, 5, 6, 7, or 8.

In some embodiments, Z is O, n is an integer from 1-16, such 4, 10, 13, or 14, m is an integer from 1-10, such as 4, 5, 6, 7, or 8, and o and p are the same integer from 1-6, such 2, 3, or 4.

In some embodiments, Z is O, n is an integer from 1-16, such 4, 10, 13, or 14, m is an integer from 1-10, such as 4, 5, 6, 7, or 8, and R is alkyl, such a methyl, ethyl, n-propyl, isopropyl, n-butyl, or t-butyl, or aryl, such as phenyl.

In certain embodiments, n is 14 (e.g., pentadecalactone, PDL), m is 7 (e.g., diethylsebacate, DES), o and p are 2 (e.g., N-methyldiethanolamine, MDEA). In certain embodiments, n, m, o, and p are as defined above, and PEG is incorporated as a monomer.

In particular embodiments, the values of x, y, and q are such that the weight average molecular weight of the polymer is greater than 20,000 Daltons.

The polymer can prepared from one or more substituted or unsubstituted lactones, one or more substituted or unsubstituted amine-diols (Z=O) or triamines (Z=NR'), and one or more substituted or unsubstituted diacids or diesters. In those embodiments where two or more different lactone, diacid or diester, and/or triamine or amine-diol monomers are used, than the values of n, o, p, and/or m can be the same or different.

The monomer units can be substituted at one or more positions with one or more substituents. Exemplary substituents include, but are not limited to, alkyl groups, cyclic alkyl groups, alkene groups, cyclic alkene groups, alkynes, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees.

In other embodiments, the polymer is biocompatible and biodegradable. The nucleic acid(s) encapsulated by and/or associated with the particles can be released through different mechanisms, including diffusion and degradation of the polymeric matrix. The rate of release can be controlled by varying the monomer composition of the polymer and thus the rate of degradation. For example, if simple hydrolysis is the primary mechanism of degradation, increasing the hydrophobicity of the polymer may slow the rate of degradation and therefore increase the time period of release. In all case, the polymer composition is selected such that an effective amount of nucleic acid(s) is released to achieve the desired purpose/outcome.

The polymers can further include a block of an alkylene oxide, such as polyethylene oxide, polypropylene oxide, and/or polyethylene oxide-co-polypropylene oxide. The structure of a PEG-containing diblock polymer is shown below:

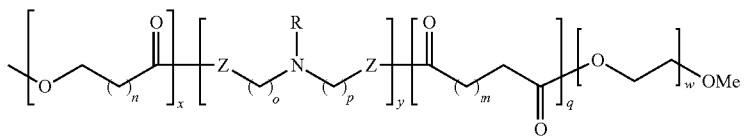

wherein n is an integer from 1-30, m, o, and p are independently an integer from 1-20, x, y, q, and w are independently integers from 1-1000, and Z is O or NR', wherein R' is hydrogen, substituted or unsubstituted alkyl, or substituted or unsubstituted aryl. In particular embodiments, the values of x, y, q, and w are such that the weight average molecular weight of the polymer is greater than 20,000 Daltons.

The structure of a PEG-containing triblock copolymer is shown below:

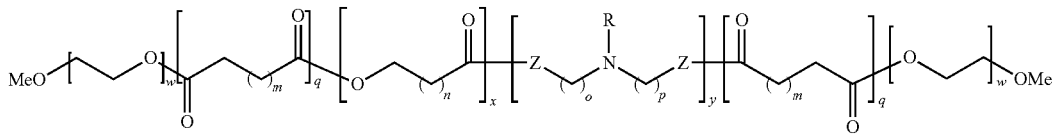

wherein n is an integer from 1-30, m, o, and p are independently an integer from 1-20, x, y, q, and w are independently integers from 1-1000, and Z is O or NR', wherein R' is hydrogen, substituted or unsubstituted alkyl, or substituted or unsubstituted aryl. In particular embodiments, the values of x, y, q, and w are such that the weight average molecular weight of the polymer is greater than 20,000 Daltons.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof.

III. Microparticles Formed from the Polymers

The polymers described above can be used to prepare micro- and/or nanoparticles having encapsulated therein one or more therapeutic, diagnostic, or prophylactic agents. The agent can be encapsulated within the particle, dispersed within the polymer matrix that forms the particle, covalently or non-covalently associated with the surface of the particle or combinations thereof.

The agent to be encapsulated and delivered can be a small molecule agent (i.e., non-polymeric agent having a molecular weight less than 2,000, 1500, 1,000, 750, or 500 Dalton) or a macromolecule (e.g., an oligomer or polymer) such as proteins, enzymes, peptides, nucleic acids, etc. Suitable small molecule active agents include organic, inorganic, and/or organometallic compounds. The particles can be used for in vivo and/or in vitro delivery of the agent.

Exemplary therapeutic agents that can be incorporated into the particles include, but are not limited to tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Exemplary diagnostic agents include paramagnetic molecules, fluorescent compounds, magnetic molecules, and radionuclides, x-ray imaging agents, and contrast agents.

In some embodiments, particles produced using the methods described here in contain less than 80%, less then 75%, less than 70%, less than 60%, less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the agent. In some embodiments, the agent may be a mixture of pharmaceutically active agents. The percent loading is dependent on a variety of factors, including the agent to be encapsulated, the polymer used to prepared the particles, and/or the method used to prepare the particles.

The particles may provide controlled release of the drug. For example, the unaltered particles may provide release of an effective amount of the drug over time based on the rate of diffusion of the drug form the particle and/or the rate of degradation of the polymer. The polymer composition can be varied to manipulate the degradation behavior of the polymer and thus the release rate/time of the agent to be delivered. Alternatively, the particle can be coated with one or more materials to provide controlled release, such as sustained release or delayed release of the agent or agents to be delivered.

Sustained release and delayed release materials are well known in the art. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Controlled release polymers known in the art include acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit®RL, 50% Eudragit®RL and 50% Eudragit® RS, and 10% Eudragit® RL and 90% Eudragit®RS. One skilled in the art will recognize that other acrylic polymers may also be used, such as, for example, Eudragit®L.

Other controlled release materials include methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragit® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac.

A. Compositions for Transfection of Polynucleotides

It has been discovered that the gene delivery ability of polycationic polymers is due to multiple factors, including polymer molecular weight, hydrophobicity, and charge density. Many synthetic polycationic materials have been tested as vectors for non-viral gene delivery, but almost all are ineffective due to their low efficiency or high toxicity. Most polycationic vectors described previously exhibit high charge density, which has been considered a major requirement for effective DNA condensation. As a result, they are able to deliver genes with high efficiency in vitro but are limited for in vivo applications because of toxicity related to the excessive charge density.

High molecular weight polymers, particularly terpolymers, and methods of making them using enzyme-catalyzed copolymerization of a lactone with a dialkyl diester and an amino diol are disclosed. These poly(amine-co-ester) terpolymers have a low charge density. In addition, their hydrophobicity can be varied by selecting a lactone comonomer with specific ring size and by adjusting lactone content in the polymers. High molecular weight and increased hydrophobicity of the lactone-diester-amino diol terpolymers compensate for the low charge density to provide efficient gene delivery with minimal toxicity.

In preferred embodiments, the terpolymers exhibit efficient gene delivery with reduced toxicity. The terpolymers can be significantly more efficient the commercially available non-viral vectors. For examples, the terpolymers described herein can be more than 100× more efficient than commercially available non-viral vectors such as PEI and LIPOFECTAMINE 2000 based on luciferase expression assay while exhibiting minimal toxicity at doses of up to 0.5 mg/ml toxicity compared to these commercially available non-viral vectors. Preferably, the terpolymer is non-toxic at concentrations suitable for both in vitro and in vivo transfection of nucleic acids. For example, in some embodiments, the disclosed terpolymers cause less non-specific cell death compared to other approaches of cell transfection.

As described in more detail below, in some embodiments, the terpolymer is ω-pentadecalactone-diethyl sebacate-N-methyldiethanolamine terpolymer containing 20% PDL (also referred to as terpolymer III-20% PDL).

IV. Micelles Formed from the Polymers

A. Micelle Properties

1. Micelle Size

The polymers described herein, such as PEG-block containing polymers can be used to prepare micelles. The average micelle size is typically in the range from about 100 to about 500 nm, preferably from about 100 to about 400 nm, more preferably from about 100 to about 300 nm, more preferably from about 150 to about 200 nm, most preferably from about 160 to about 190 nm, which were stable at physiological pH of 7.4 in the presence of serum proteins. The copolymers possess high blood compatibility and exhibit minimal activity to induce hemolysis and agglutination.

2. Surface Charge

The size and zeta potential of the micelles were found to change significantly when the pH of the aqueous medium accommodating the micelles was varied. For example, the trends in the size-pH and zeta-pH curves are remarkably similar for the micelles of the three PEG2K-PPMS copolymers with different PDL contents (11%, 30%, and 51%). It is evident that the average size of the micelle samples gradually increases upon decreasing the medium pH from 7.4 to 5.0, and then remains nearly constant when the pH value is below 5.0. This pH-responsive behavior observed for the micelles is anticipated since upon decreasing the pH from 7.4 to 5.0, the PPMS cores of the micelles become protonated and more hydrophilic, thus absorbing more water molecules from the aqueous medium to cause swelling of the micelles. 18 It is assumed that the micelle cores are already fully protonated at pH of 5.0, and as the result, the sizes of the micelles remain fairly constant with further decreasing of the pH from 5.0. The effects of the PDL content in the PEG2K-PPMS copolymers on the magnitude of the micelle size change between 7.4 and 5.0 pH values are also notable. With decreasing PDL content and increasing tertiary amino group content in the copolymer, the capacity of the micelle cores to absorb protons and water molecules is expected to increase. Thus, upon decreasing pH from 7.4 to 5.0, the change in average micelle size was more significant for PEG2K-PPMS-11% PDL (from 200 nm to 234 nm) as compared to PEG2K-PPMS-30% PDL (from 184 nm to 214 nm) and PEG2K-PPMS-51% PDL (from 163 nm to 182 nm) (FIG. 4A).

The zeta potential of the micelles in aqueous medium also exhibits substantial pH-dependence. At physiological and alkaline pH (7.4 to 8.5), the surface charges of blank PEG2K-PPMS copolymer micelles were negative, which changed to positive when the pH of the medium decreased to acidic range (4.0-6.0). For example, the micelles of PEG2K-PPMS-11% PDL, PEG2K-PPMS-30% PDL, and PEG2K-PPMS-51% PDL possessed zeta potential values of −5.8, −7.1, −5.1 mV, respectively, at pH of 7.4, which turned to +7.6, +5.8, +4.0 mV, correspondingly, at a lower pH of 5.0. On the basis of the above discussions, this surface charge dependence on pH is attributable to the protonation or deprotonation of the PPMS cores of the micelles at different medium pH. At an alkaline pH (7.4-8.5), most of the amino groups in the micelles presumably are not protonated, and the micelle particles remain negatively charged due to the absorption of HPO42- and/or H2PO4-anions in PBS by the micelles. In particular, at pH of 8.5, the zeta-potential values were −8.1 mV, −7.9 mV, −9.0 mV for PEG2K-PPMS-11% PDL, PEG2K-PPMS-30% PDL, and PEG2K-PPMS-51% PDL, respectively. Upon decreasing pH from 7.4 to 5.0, the tertiary amino moieties in the micelle PPMS cores become mostly protonated, turning the micelles to positively charged particles. Consistently, among the three micelle samples, PEG2K-PPMS-11% PDL micelles with the largest capacity to absorb protons displayed the highest zeta potential values at pH of 4.0-5.0, whereas PEG2K-PPMS-51% PDL micelles with the smallest protonation capacity showed the lowest zeta potentials. The observed micelle surface charge responses to the medium pH are highly desirable since the negative surface charge of the micelles at physiological pH can alleviate the interaction of the micelles with serum protein in the blood and prolong their in vivo circulation time. On the other hand, the reverse to positive surface charge at the tumor extracellular pH of approximately 6.5 could enhance the uptake of these micelles by target tumor cells.

The surface charge of the particles/micelles were slightly negative in PBS solution (0.01M, pH=7.4), which are beneficial for in vivo drug delivery applications of the micelles. It is known that nanoparticles with nearly neutral surface charge (zeta potential between −10 and +10 mV) can decrease their uptake by the reticuloendothelial system (RES) and prolong their circulation time in the blood. The negative surface charges of the micelles could result from the absorption of $HPO_4^{2-}$ and/or $H_2PO_4^-$ anions in PBS by the micelle particles via hydrogen bonding interactions between the anions and the ether groups of PEG shells or the amino groups of PPMS cores. For amphiphilic block copolymer micelles, it is anticipated that hydrophilic chain segments (e.g., PEG) in the outer shell of the micelles can shield the charges in the micelle core with the long chain blocks being more effective in reducing zeta potential than the short chain blocks. Thus, significantly lower zeta potential values were observed for PEG5K-PPMS copolymer micelles as compared to PEG2K-PPMS copolymer micelles.

The copolymer micelles are pH-responsive: decreasing the medium pH from 7.4 to 5.0, the sizes of the micelles significantly increased micelle size while the micelle surface charges reversed from negative charges to positive charges. Correspondingly, DTX-encapsulated copolymer micelles showed gradual sustained drug release at pH of 7.4, but remarkably accelerated DTX release at acidic pH of 5.0. This phenomenon can be exploited to improve release of agents at tumor site, since it is known that the tumor microenvironment is typically weakly acidic (e.g., 5.7-7.0) as the result of lactic acid accumulation due to poor oxygen perfusion. In contrast, the extracellular pH of the normal tissue and blood is slightly basic (pH of 7.2-7.4). Thus, enhanced drug delivery efficiency is anticipated for anticancer drug-loaded micelles that are pH-responsive and can be triggered by acidic pH to accelerate the drug release. Furthermore, even more acidic conditions (pH=4.0-6.0) are encountered in endosomes and lysosomes after uptake of the micelles by tumor cells via endocytosis pathways, which may further increase the cytotoxicity of the drug-encapsulated micelles.

V. Methods of Making the Polymers

Methods for the synthesis of the polymers from a lactone, a dialkyl ester, and a dialkyl amine using an enzyme catalyst, such as a lipase, are also provided. Exemplary lactones are shown in FIG. 1. In one embodiment, the polymers are prepared as shown in Scheme 1:

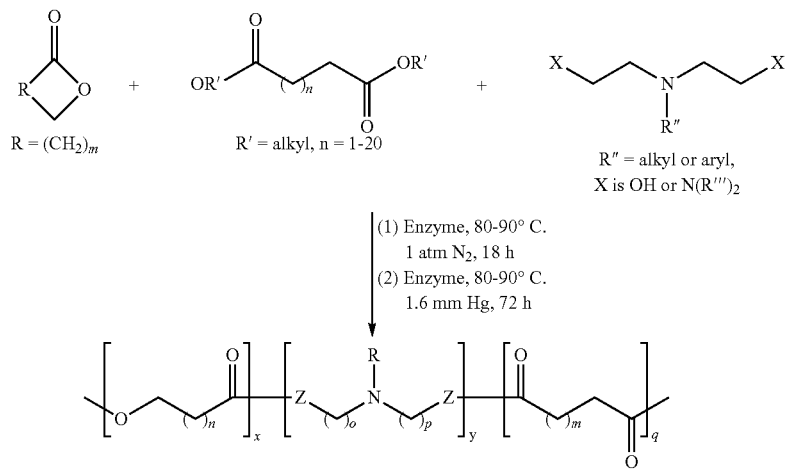

Scheme 1: Preparation of poly(amine-co-ester) terpolymers wherein n is an integer from 1-30, m, o, and p are independently an integer from 1-20, and x, y, and q are independently integers from 1-1000. The polymer can prepared from one or more lactones, one or more amine-dials or triamines, and one or more diacids or diesters. In those embodiments where two or more different lactone, diacid or diester, and/or triamine or amine-diol monomers are used, than the values of n, o, p, and/or m can be the same or different.

The synthesis of the polymers described herein using PDL, DES, MDA, and PEG as reactants is shown in Scheme 2.

Scheme 2: Enzymatic Synthesis of PEG-PPMS Block Copolymers

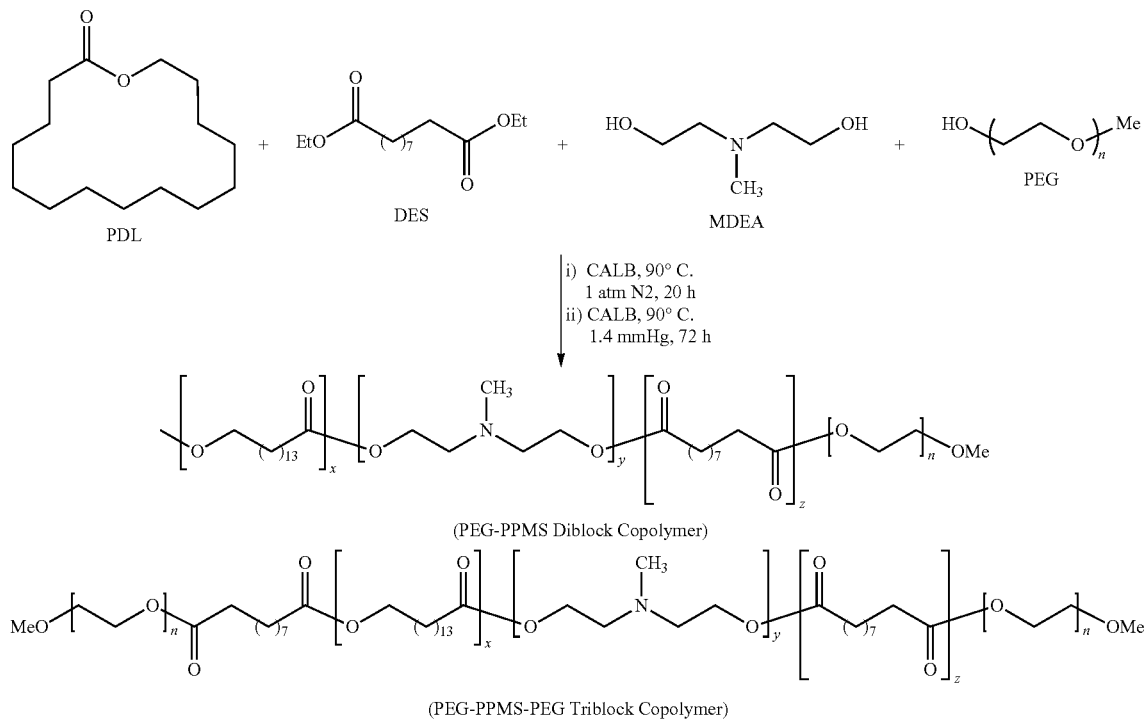

The molar ratio of the monomers can vary, for example from about 10:90:90 to about 90:10:10. In some embodiments, the ratio is 10:90:90, 20:80:80, 40:60:60, 60:40:40, or 80:20:20. The weight average molecular weight, as determined by GPC using narrow polydispersity polystyrene standards, can vary for example from about 10,000 Daltons to about 50,000 Daltons, preferably from about 15,000 Daltons to about 50,000 Daltons.

The enzymatic method described herein allows for the synthesis of polymers with diverse chain structures and tunable hydrophobicities. In some embodiments, the hydrophobicity is varied by varying the ring size and/or molar amount of the lactone monomer. Lactone with a wide range of ring sizes (e.g., $C_4$-$C_{24}$, preferably $C_6$-$C_{24}$, more preferably from $C_6$-$C_{16}$) can be used as comonomers. The reaction can be performed in a single step without protection and deprotection of the amino group(s). Such amino-bearing copolyesters are extremely difficult to prepare using conventional organometallic catalysts, as such catalysts are often sensitive to or deactivated by organic amines. These catalysts are also known to be inefficient for polymerizing large lactone ring monomers. Enzymatic catalysts have distinct advantages for producing biomedical polymers owing to the high activity and selectivity of the enzyme and the resulting high purity of products that are metal-free.

Exemplary polymers prepared from a lactone (e.g., caprolactone (CL), ω-pentadecalactone (PDL), 16-hexadecanolide (HDL)), diethyl sebacate (DES), and a dialkyl amine (e.g., N-methyldiethanolamine (MDEA)) are described in Table 1 below. To simplify nomenclature, CL-DES-MDEA, DDL-DES-MDEA, PDL-DES-MDEA, and HDL-DES-MDEA terpolymers are designated as polymer I, II, III, and IV, respectively.

TABLE 1 shows the yield, composition, weight average molecular weight, polydispersity, and other characterization data of selected terpolymers.

| Name[a] | Lactone/DES/MDEA (Feed Molar Ratio) | Lactone/Sebacate/MDEA (Unit Molar Ratio)[b] | Isolated Yield (%) | $M_w$[c] | $M_w/M_n$[c] | Nitrogen Content (wt %) | Solubility in DMSO mg ml$^{-1}$ |
|---|---|---|---|---|---|---|---|
| PMSC | 0:50:50 | 0:50:50 | — | 31800 | 2.3 | 4.9 | >25 |
| I-10% CL | 10:90:90 | 10:90:90 | 85 | 18400 | 1.9 | 4.7 | >25 |
| I-20% CL | 20:80:80 | 20:80:80 | 80 | 19100 | 1.9 | 4.5 | >25 |
| I-40% CL | 40:60:60 | 40:60:60 | 83 | 18400 | 1.8 | 3.9 | >25 |
| I-60% CL | 60:40:40 | 60:40:40 | 81 | 17800 | 1.8 | 3.1 | >25 |
| I-80% CL | 80:20:20 | 80:20:20 | 86 | 20300 | 2.0 | 1.9 | >25 |

TABLE 1-continued shows the yield, composition, weight average molecular weight,
polydispersity, and other characterization data of selected terpolymers.

| Name[a] | Lactone/DES/MDEA (Feed Molar Ratio) | Lactone/Sebacate/MDEA (Unit Molar Ratio)[b] | Isolated Yield (%) | $M_w$[c] | $M_w/M_n$[c] | Nitrogen Content (wt %) | Solubility in DMSO mg ml$^{-1}$ |
|---|---|---|---|---|---|---|---|
| II-10% DD | 10:90:90 | 10:90:90 | 82 | 24900 | 1.9 | 4.6 | >25 |
| II-20% DD | 20:80:80 | 20:80:80 | 80 | 29300 | 2.0 | 4.2 | >25 |
| II-40% DD | 40:60:60 | 40:60:60 | 81 | 25800 | 1.8 | 3.4 | >25 |
| II-60% DD | 60:40:40 | 60:40:40 | 84 | 47400 | 2.1 | 2.4 | |
| II-80% DD | 80:20:20 | 80:20:20 | 87 | 40600 | 2.1 | 1.3 | |
| III-10% PD | 10:90:90 | 10:90:90 | 81 | 30700 | 2.1 | 4.5 | >25 |
| III-20% PD | 20:80:80 | 20:80:80 | 83 | 38700 | 2.3 | 4.1 | ≈25 |
| III-40% PD | 40:60:60 | 40:60:60 | 85 | 33300 | 2.1 | 3.1 | |
| III-61% PD | 60:40:40 | 61:39:39 | 83 | 34500 | 2.3 | 2.1 | |
| III-82% PD | 80:20:20 | 82:18:18 | 88 | 41700 | 2.7 | 1.0 | |
| IV-10% HD | 10:90:90 | 10:90:90 | 80 | 25700 | 1.8 | 4.5 | >25 |
| IV-20% HD | 20:80:80 | 20:80:80 | 81 | 26600 | 1.9 | 4.0 | |
| IV-40% HD | 40:60:60 | 40:60:60 | 83 | 31200 | 2.2 | 3.1 | |
| IV-61% HD | 60:40:40 | 61:39:39 | 86 | 37400 | 2.2 | 2.0 | |
| IV-80% HD | 80:20:20 | 80:20:20 | 89 | 59000 | 2.1 | 1.1 | | a. The polymer names are abbreviated or simplified. PMSC: poly(N-methyldiethyleneamine sebacate). Polymers I, II, III, and IV represent CL-DES-MDEA, DDL-DES-MDEA, PDL-DES-MDEA, and HDL-DES-MDEA terpolymers, respectively. Each polymer is denoted with x % lactone indicating the lactone unit content [mol % vs. (lactone+sebacate) units] in the polymer.
b. Measured by $^1$H NMR spectroscopy.
c. Measured by GPC using narrow polydispersity polystyrene standards.

C. Therapeutic, Prophylactic and Diagnostic Agents

The polymers described herein can form various polymer compositions, which are useful for preparing a variety of biodegradable medical devices and for drug delivery. Devices prepared from the PHA copolymers described herein can be used for a wide range of different medical applications. Examples of such applications include controlled release of therapeutic, prophylactic or diagnostic agents; drug delivery; tissue engineering scaffolds; cell encapsulation; targeted delivery; biocompatible coatings; biocompatible implants; guided tissue regeneration; wound dressings; orthopedic devices; prosthetics and bone cements (including adhesives and/or structural fillers); and diagnostics.

The polymers described herein can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomagraphy (CT) and positron emission tomagraphy (PET). Ultrasound diagnostic agents are typically a gas such as air, oxygen or perfluorocarbons. In a preferred embodiment, the polymers are used for delivery of nucleic acids.

Polynucleotides

As discussed in more detail below, the disclosed terpolymers can be used to transfect cells with nucleic acids. Accordingly, polyplexes including terpolymers and one or more polynucleotides are also disclosed.

The polynucleotide can encode one or more proteins, functional nucleic acids, or combinations thereof. The polynucleotide can be monocistronic or polycistronic. In some embodiments, polynucleotide is multigenic.

In some embodiments, the polynucleotide is transfected into the cell and remains extrachromosomal. In some embodiments, the polynucleotide is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the polynucleotide is incorporated into or part of a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, the polynucleotide of interest is operably linked to a promoter or other regulatory elements known in the art. Thus, the polynucleotide can be a vector such as an expression vector. The engineering of polynucleotides for expression in a prokaryotic or eukaryotic system may be performed by techniques generally known to those of skill in recombinant expression. An expression vector typically comprises one of the disclosed compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors. It will be appreciated that any of these vectors may be packaged and delivered using the disclosed polymers.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

1. Polypeptide of Interest

The polynucleotide can encode one or more polypeptides of interest. The polypeptide can be any polypeptide. For example, the polypeptide encoded by the polynucleotide can be a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polynucleotide(s) to be expressed may encode a polypeptide that functions as a ligand or receptor for cells of the immune system, or can function to stimulate or inhibit the immune system of an organism. As discussed in the example below, a polynucleotide encoding TNF-related apoptosis-inducing ligand (TRAIL) can be delivered to tumor cells using the disclosed polyplexes in a method of treating cancer.

In some embodiments, the polynucleotide supplements or replaces a polynucleotide that is defective in the organism.

In some embodiments, the polynucleotide includes a selectable marker, for example, a selectable marker that is effective in a eukaryotic cell, such as a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the polynucleotide includes a reporter gene. Reporter genes are typically genes that are not present or expressed in the host cell. The reporter gene typically encodes a protein which provides for some phenotypic change or enzymatic property. Examples of such genes are provided in Weising et al. *Ann. Rev. Genetics*, 22, 421 (1988). Preferred reporter genes include glucuronidase (GUS) gene and GFP genes.

2. Functional Nucleic Acids

The polynucleotide can be, or can encode a functional nucleic acid. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

3. Composition of the Polynucleotides

The polynucleotide can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

The polynucleotide can be composed of nucleotide analogs that have been chemically modified to improve stability, half-life, or specificity or affinity for a target sequence, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge. Modifications should not prevent, and preferably enhance, the ability of the oligonucleotides to enter a cell and carry out a function such inhibition of gene expression as discussed above.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

As discussed in more detail below, in one preferred embodiment, the oligonucleotide is a morpholino oligonucleotide.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl)uracil (pU), 5-(1-propynyl)cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Polynucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-β-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or deoxyribose and also forms a bridge with the i–1 phosphate in the purine strand of the duplex.

The polynucleotide can be a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer: RNA heteroduplex to resist RNAse degradation. In some embodiments, oligonucleotides employ morpholino-based subunits bearing base-pairing moieties, joined by uncharged linkages.

c. Internucleotide Linkages

Internucleotide bond refers to a chemical linkage between two nucleoside moieties. Modifications to the phosphate backbone of DNA or RNA oligonucleotides may increase the binding affinity or stability polynucleotides, or reduce the susceptibility of polynucleotides to nuclease digestion. Cationic modifications, including, but not limited to, diethylethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571, and 5,786,571.

Polynucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. For example, lysine and arginine residues can be added to a bis-PNA linker or can be added to the carboxy or the N-terminus of a PNA strand. Polynucleotides may further be modified to be end capped to prevent degradation using a 3' propylamine group. Procedures for 3' or 5' capping oligonucleotides are well known in the art.

D. Coating Agents for Polyplexes

Efficiency of polynucleotide delivery using the disclosed polymers can be affected by the positive charges on the polyplex surface. For example, a zeta potential of the polyplex of +8.9 mV can attract and bind with negatively charged plasma proteins in the blood during circulation and lead to rapid clearance by the reticuloendothelial system (RES). Efficiency can also be affected by instability of the polyplex nanoparticles. For example, as discussed in the Examples below, polyplex particles incubated in NaAc buffer solution containing 10% serum nearly doubled in size within 15 minutes and increased by over 10-fold after 75 minutes. As a result of this increase in size, enlarged polyplexes might be cleared from the circulation by uptake in the liver. Therefore, in some embodiments the polyplexes are treated or coated to improve polynucleotide delivery efficiency. In some embodiments, the coating improves cell specific targeting of the polyplex, improves the stability (i.e., stabilizes the size of the polyplex in vivo), increases the half-life of the polyplex in vivo (i.e., in systemic circulation), or combinations thereof compared to a control. In some embodiments, the control is a polyplex without a coating.

1. Compositions for Altering Surface Charge

Polynucleotide delivery efficiency of the disclosed polyplexes can be improved by coating the particles with an agent that is negatively charged at physiological pH. Preferably, the negatively charged agent is capable of electrostatic binding to the positively charged surface of the polyplexes. The negatively charged agent can neutralize the charge of the polyplex, or reverse the charge of the polyplex. Therefore, in some embodiments, the negatively charged agent imparts a net negative charge to the polyplex.

In some embodiments, the negatively charged agent is a negatively charged polypeptide. For example, the polypeptide can include aspartic acids, glutamic acids, or a combination therefore, such that the overall charge of the polypeptide is a negative at neutral pH. In some embodiments, the polypeptide is a poly aspartic acid polypeptide consisting of 3, 4, 5, 6, 7, 8, 9, 10, 11, 12, 13, 14, 15, 16, 17, 18, 19, 20, or more than 20 aspartic acid residues. In some embodiments, the polypeptide is a poly glutamic acid polypeptide consisting of 3, 4, 5, 6, 7, 8, 9, 10, 11, 12, 13, 14, 15, 16, 17, 18, 19, 20, or more than 20 glutamic acid residues. Other negatively charged molecules include small molecules (i.e., MW less than 1500, 100, 750, or 500 Daltons) such as hyaluronic acid.

Increasing the negative charge on the surface of the particle can reduce or prevent the negative interactions described above, wherein more positively charged particles attract and bind negatively charged plasma proteins in the blood during circulation and lead to rapid clearance by the reticuloendothelial system (RES). In some embodiments, the zeta potential of the particles is from about −15 mV to about 10 mV, preferably from about −15 mV to about 8 mV, more preferably from about −10 mV to about 8 mV, more preferably from about −8 mV to about 8 mV. The zeta potential can be more negative or more positive than the ranges above provided the particles are stable (i.e., don't aggregate, etc.) and not readily cleared from the blood stream The zeta potential can be manipulated by coating or functionalizing the particle surface with one or more moieties which varies the surface charge. Alternatively, the monomers themselves can be functionalized and/or additional monomers can be introduced into the polymer, which vary the surface charge.

2. Targeting Moieties

In some embodiments, the polyplexes include a cell-type or cell-state specific targeting domain or targeting signal. Examples of moieties which may be linked or unlinked to the polyplexes include, for example, targeting moieties which provide for the delivery of molecules to specific cells. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

The targeting moiety can be an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

One skilled in the art will appreciate that the tropism of the polyplexes described can be altered by merely changing the targeting signal. It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

Tumor Targeting

In one embodiment, the targeting signal is used to selectively target tumor cells. Tumor cells express cell surface markers which may only be expressed in the tumor or present in non-tumor cells but preferentially presented in tumor cells. Such markers can be targeted to increase delivery of the polyplexes to cancer cells.

For example, in some embodiments, the targeting moiety is a polypeptide including an arginine-glycine-aspartic acid sequence. For example, the targeting moiety can be an arginine-glycine-aspartic acid-lysine (RGDK, mRGD) other polypeptide that includes the RGD sequence and is capable of binding to tumor endothelium through the interaction of RGD with $\alpha_v\beta_3$ and $\alpha_v\beta_5$. In some embodiments, a targeting moiety includes the polypeptide sequence R/KxxR/K, where "x" is any amino acid, and which allows binding to neuropilin-1. Binding with integrins or neuropilin-1 are two approaches for improving tumor-targeted and tissue-penetrating delivery to tumors in vivo. Similar approaches have been reported to facilitate ligand-specific gene delivery in vitro and targeted gene delivery to liver, spleen, and bone marrow in vivo.

Other, exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, NCAM, EGFR, CD44, and folate receptor. In one embodiment, the targeting signal consists of antibodies which are specific to the tumor cell surface markers.

Antibodies

Another embodiment provides an antibody or antigen binding fragment thereof bound to the disclosed polyplex acts as the targeting signal. The antibodies or antigen binding fragment thereof are useful for directing the polyplex to a cell type or cell state. In one embodiment, the polyplex is coated with a polypeptide that is an antibody binding domain, for example from a protein known to bind antibodies such as Protein A and Protein G from *Staphylococcus aureus*. Other domains known to bind antibodies are known in the art and can be substituted. The antibody binding domain links the antibody, or antigen binding fragment thereof, to the polyplex.

In certain embodiments, the antibody that serves as the targeting signal is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the polyplex to the desired target cell type or cell state. Antibodies can be monoclonal or polyclonal, but are preferably monoclonal. For human gene therapy purposes, antibodies can be derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Brain Targeting

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neurosphere.

Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7, and MR4.

3. Linkers

In some embodiments the polyplex can be coated with both a negatively charged agent and a targeting moiety. In some embodiments, the negatively charged agent and the targeting moiety are linked together by a linker. The linker can be a polypeptide, or any other suitable linker that is known in the art, for example, poly ethylene glycol (PEG).

In some embodiments, the linker is polypeptide that has approximately neutral charge at physiological pH. In some embodiments, the linker polypeptide is a polyglycine. For example, in some embodiments the linker consists of 3, 4, 5, 6, 7, 8, 9, 10, 11, 12, 13, 14, 15, 16, 17, 18, 19, 20, or glycine residues. In a preferred embodiment, the linker is a 6-residue polyglycine.

In some embodiments, the negatively charged agent alone, or in combination with a targeting moiety is linked to the polyplex by electrostatic interactions. In some embodiments, the negative charged agent, the targeting moiety, or a combination thereof is linked to the polyplex by covalent conjugation to the polymer backbone or to a side chain attached to the polymer backbone.

4. Exemplary Polyplex Coating

An exemplary polyplex coating for targeting tumor cells is polyE-mRGD. As used herein, polyE-mRGD refers to a synthetic peptide containing three segments: a first segment including a polyglutamic acid (polyE) stretch, which is negatively charged at physiological pH and, therefore, capable of electrostatic binding to the positively charged surface of the polyplexes; a second segment including a neutral polyglycine stretch, which serves as a neutral linker; and a third segment that includes a RGD sequence that binds the tumor endothelium through the interaction of RGD with $\alpha_v\beta_3$ and $\alpha_v\beta_5$.

As discussed in more detail below, the polyE-mRGD used in the Examples reversed the surface charge of III-20% PDL/ pLucDNA polyplex. When polyE-mRGD was added at 5:1 peptide/DNA weight ratio, the zeta potential of the polyplex changed from +8.9 mV to −5.8 mV. Peptide coated polyplexes were stable upon incubation in NaAc buffer containing 10% serum and resistant to aggregation indicating that the modified polyplexes can escape clearance by RES during circulation in vivo.

In one embodiment, polyE-mRGD includes the sequence EEEEEEEEEEEEEEEEGGGGGGRGDK (SEQ ID NO:1), or RGDKGGGGGG EEEEEEEEEEEEEEEE (SEQ ID NO:2), or a variant thereof with 85%, 90%, 95%, or more than 95% sequence identity to SEQ ID NO:1 or 2.

Another exemplary coating that can be used to prepare charge neutral, or negatively charged particles that maintain their size in vivo are described in Harris, et al., *Biomaterials*, 31:998-1006 (2010)), and can include the amino acid sequence GGGGGGEEEEEEEEEEEEEEEE (SEQ ID NO:3, poly-E), for non-specific systemic administration, or the amino acids sequence GdPdLGdVdRG-GGGGGG-EE-EEEEEEEEEEEEEE-CONH2 (SEQ ID NO:4, poly-E-cat), which contains a polycationic sequence that increase targeting to the spleen, spine, sternum, and femur. In some embodiments, the polypeptide used in the coating is a variant SEQ ID NO:3 or 4, with 85%, 90%, 95%, or more than 95% sequence identity to SEQ ID NO:3 or 4

In vitro studies have indicated that adsorption of immunoglobulin G (IgG) and complement protein C3 to nanoparticles increases their uptake by Kupffer cells and incubation in serum increases hepatic uptake in vivo following liver perfusion (Nagayama, et al., *Int. J. Pharm.*, 342:215-21 (2007)). Reports also indicate that galactose can be used to guide polymeric gene delivery particles to hepatocytes via the asialoglycoprotein receptor (ASGPR (SEQ ID NO:6) (Zhang, et al., *J. Controlled Release,* 102:749-63 (2005)).

E. Size of Polyplexes and Methods of Reducing Aggregation

Resistance to aggregation can be important because maintaining a small particle size limits clearance by the liver and maintains transfection ability of polyplex particles into target cells. Therefore, in preferred embodiments, the polyplexes are resistant to aggregation. Preferably, polyplexes with or without coating are between about 1 nm and 1000 nm in radius, more preferably between about 1 nm and about 500 nm in radius, most preferably between about 15 nm and about 250 nm in radius. For example, in some embodiments, coated polyplexes loaded with polynucleotide are between about 150 nm and 275 nm in radius.

The ratio of polynucleotide weight to polymer weight (polynucletide:polymer), the content and quantity of polyplex coating, or a combination thereof can be used to adjust the size of the polyplexes.

For example, the Examples below show that in some embodiments, transfection efficiency of particles with 25:1 polymer to DNA ratio is lower than the transfection efficiency of particles with 50:1, 100:1, 150:1, and 200:1 polymer:DNA ratios. The most preferred polymer:polynucleotide ratio for a particular formulation can be determined empirically using the methods that are known in the art, such as those described in the Examples below. Generally, the weight:weight ratio of polymer:polynucleotide is preferably greater than about 10:1, more preferably greater than about 50:1, most preferably greater than about 100:1. The weight:weight ratio of polymer:polynucleotide is preferably between about 10:1 and 500:1, more preferably between about 25:1 and 250:1, most preferably between about 50:1 and 150:1. In some embodiments, the weight ratio of polymer:polynucleotide is about 100:1. Preferably, the polyplexes has are spherical in shape.

Examples below also show that in some embodiments, transfection efficiency of particles by the ratio of coating agent molecules to polynucleotide molecules (coating agent:polynucleotide). The ratio is expressed by weight. The most preferred coating agent:polynucleotide ratio for a particular formulation can be determined empirically using the methods that are known in the art, such as those described in the Examples below. Generally, the ratio of coating agent:polynucleotide is greater than 0, and preferably lower than about 50:1, more preferably lower than about 25:1, most preferably lower than about 10:1. The ratio coating agent:polynucleotide is preferably between about 1:1 and 10:1, more preferably between about 2.5:1 and 7.5:1. In some embodiments, the ratio of coating agent:polynucleotide is about 5:1. Ratios of coating agent:polynucleotide of 10:1, 5:1, and 2.5:1 are also referred to herein as 10×, 5×, and 2.5× respectively. Preferably, the polyplexes are spherical in shape.

F. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristo-amphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit®. L30D-55 and L100-55 (soluble at pH 5.5 and above), Eudragit®. L-100 (soluble at pH 6.0 and above), Eudragit®. S (soluble at pH 7.0 and above, as a result of a higher degree of esterification), and Eudragit®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multilayer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release Formulations

By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

For dosage forms mimicking a twice a day dosing profile, a first group of beads, granules or particles releases drug substantially immediately following ingestion of the dosage form, while a second group of beads or granules preferably releases drug approximately 3 hours to less than 14 hours following ingestion of the dosage form. For dosage forms mimicking a three times daily dosing profile, a first group of beads, granules or particles releases drug substantially immediately following ingestion of the dosage form, a second group of beads or granules preferably releases drug approximately 3 hours to 10 hours following ingestion of the dosage form, and a third group of beads, granules or particles releases drug at least 5 hours to approximately 18 hours following ingestion of the dosage form. The above-mentioned tablets, beads, granules or particles of different drug release profiles (e.g., immediate and delayed release profiles) may be mixed and included in a capsule, tablet or matrix to provide a pulsatile dosage form having the desired release profile.

In another embodiment, the individual dosage units are compacted in a single tablet, and may represent integral but discrete segments thereof (e.g., layers), or may be present as a simple admixture. For example, drug-containing beads, granules or particles with different drug release profiles (e.g., immediate and delayed release profiles) can be compressed together into a single tablet using conventional tableting means.

In a further alternative embodiment, a dosage form is provided that comprises an inner drug-containing core and at least one drug-containing layer surrounding the inner core. An outer layer of this dosage form contains an initial, immediate release dose of the drug. For dosage forms mimicking twice daily dosing, the dosage form has an outer layer that releases drug substantially immediately following oral administration and an inner core having a polymeric-coating that preferably releases the active agent approximately 3 hours to less than 14 hours following ingestion of the dosage unit. For dosage forms mimicking three times daily dosing, the dosage form has an outer layer that releases drug substantially immediately following oral administration, an inner core that preferably releases drug at least 5 hours to 18 hours following oral administration and a layer interposed between the inner core and outer layer that preferably releases drug approximately 3 hours to 10 hours following ingestion of the dosage form. The inner core of the dosage form mimicking three times daily dosing may be formulated as compressed delayed release beads or granules.

Alternatively, for dosage forms mimicking three times daily dosing, the dosage form has an outer layer and an inner layer free of drug. The outer layer releases drug substantially immediately following oral administration, and completely surrounds the inner layer. The inner layer surrounds both the second and third doses and preferably prevents release of these doses for approximately 3 hours to 10 hours following oral administration. Once released, the second dose is immediately available while the third dose is formulated as delayed release beads or granules such that release of the third dose is effected approximately 2 hours to 8 hours thereafter effectively resulting in release of the third dose at least 5 hours to approximately 18 hours following ingestion of the dosage form. The second and third doses may be formulated by admixing immediate release and delayed release beads, granules or particles and compressing the admixture to form a second and third dose-containing core followed by coating the core with a polymer coating to achieve the desired three times daily dosing profile.

In still another embodiment, a dosage form is provided which comprises a coated core-type delivery system wherein the outer layer is comprised of an immediate release dosage unit containing an active agent, such that the active agent therein is immediately released following oral administration; an intermediate layer there under which surrounds a core; and a core which is comprised of immediate release beads or granules and delayed release beads or granules, such that the second dose is provided by the immediate release beads or granules and the third dose is provided by the delayed release beads or granules.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material; increasing drug particle size; placing the drug within a matrix; and forming complexes of the drug with suitable complexing agents.

Exemplary methods of preparing polyplexes for transfection are discussed in the Examples below.

VI. Methods of Preparing Polyplexes

A. Methods for Making Particles

Particles can be prepared using a variety of techniques known in the art. The technique to be used can depend on a variety of factors including the polymer used to form the nanoparticles, the desired size range of the resulting particles, and suitability for the material to be encapsulated. Suitable techniques include, but are not limited to:

a. Solvent Evaporation. In this method the polymer is dissolved in a volatile organic solvent. The drug (either soluble or dispersed as fine particles) is added to the solution, and the mixture is suspended in an aqueous solution that contains a surface active agent such as polyvinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

b. Hot Melt Microencapsulation. In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting nanoparticles are washed by decantation with petroleum ether to give a free-flowing powder. The external surfaces of spheres prepared with this technique are usually smooth and dense.

c. Solvent Removal. In this method, the drug is dispersed or dissolved in a solution of the selected polymer in a volatile organic solvent. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

d. Spray-Drying. In this method, the polymer is dissolved in organic solvent. A known amount of the active drug is suspended (insoluble drugs) or co-dissolved (soluble drugs) in the polymer solution. The solution or the dispersion is then spray-dried.

e. Phase Inversion. Nanospheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposomes).

In one embodiment, the loaded particles are prepared by combining a solution of the polymer, typically in an organic solvent, with the polynucleotide of interest. The polymer solution is prepared by dissolving or suspending the polymer in a solvent. The solvent should be selected so that it does not adversely effect (e.g., destabilize or degrade) the nucleic acid to be encapsulated. Suitable solvents include, but are not limited to DMSO and methylene chloride. The concentration of the polymer in the solvent can be varied as needed. In some embodiments, the concentration is for example 25 mg/ml. The polymer solution can also be diluted in a buffer, for example, sodium acetate buffer.

Next, the polymer solution is mixed with the agent to be encapsulated, such as a polynucleotide. The agent can be dissolved in a solvent to form a solution before combining it with the polymer solution. In some embodiments, the agent is dissolved in a physiological buffer before combining it with the polymer solution. The ratio of polymer solution volume to agent solution volume can be 1:1. The combination of polymer and agent are typically incubated for a few minutes to form particles before using the solution for its desired purpose, such as transfection. For example, a polymer/polynucleotide solution can be incubated for 2, 5, 10, or more than 10 minutes before using the solution for transfection. The incubation can be at room temperature.

In some embodiments, the particles are also incubated with a solution containing a coating agent prior to use. The particle solution can be incubated with the coating agent for 2, 5, 10, or more than 10 minutes before using the polyplexes for transfection. The incubation can be at room temperature.

In some embodiments, if the agent is a polynucleotide, the polynucleotide is first complexed to a polycation before mixing with polymer. Complexation can be achieved by mixing the polynucleotides and polycations at an appropriate molar ratio. When a polyamine is used as the polycation species, it is useful to determine the molar ratio of the polyamine nitrogen to the polynucleotide phosphate (N/P ratio). In a preferred embodiment, inhibitory RNAs and polyamines are mixed together to form a complex at an N/P ratio of between approximately 1:1 to 1:25, preferably between about 8:1 to 15:1. The volume of polyamine solution required to achieve particular molar ratios can be determined according to the following formula:

$$V_{NH2} = \frac{C_{inhRNA,final} \times M_{w,inhRNA} / C_{inhRNA,final} \times M_{w,P} \times \Phi_{N:P} \times \Phi V_{final}}{C_{NH2} / M_{w,NH2}}$$

where $M_{w,inhRNA}$=molecular weight of inhibitory RNA, $M_{w,P}$=molecular weight of phosphate groups of inhibitory RNA, $\Phi_{N:P}$=N:P ratio (molar ratio of nitrogens from polyamine to the ratio of phosphates from the inhibitory RNA), $C_{NH2}$, stock=concentration of polyamine stock solution, and $M_{w,NH2}$=molecular weight per nitrogen of polyamine. Methods of mixing polynucleotides with polycations to condense the polynucleotide are known in the art. See for example U.S. Published Application No. 2011/0008451.

The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values. Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In some embodiments, the polycation is a polyamine. Polyamines are compounds having two or more primary amine groups. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/

012096 and WO 2002/010142. Exemplary cyclic polyamines include, but are not limited to, cyclen.

Spermine and spermidine are derivatives of putrescine (1,4-diaminobutane) which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

B. Methods for Transfection

Transfection is carried out by contacting cells with the solution containing the polyplexes. For in vivo methods, the contacting typically occurs in vivo after the solution is administered to the subject. For in vitro methods, the solution is typically added to a culture of cells and allowed to contact the cells for minutes, hours, or days. The cells can subsequently be washed to move excess polyplexes.

V. Methods of Using the Particles/Micelles

A. Drug Delivery

The particles described herein can be use to deliver an effective amount of one or more therapeutic, diagnostic, and/or prophylactic agents to a patient in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles may be administered as a dry powder, as an aqueous suspension (in water, saline, buffered saline, etc), in a hydrogel, organogel, or liposome, in capsules, tablets, troches, or other standard pharmaceutical excipient.

B. Transfection

The disclosed compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000 or polyethylenimine (PEI).

The particular polynucleotide delivered by the polyplex can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

In some embodiments, the polynucleotide encodes a protein. Exemplary proteins include, for example, (a) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor-α, hepatocyte growth factor and insulin-like growth factor; (b) cell cycle inhibitors such as cyclin-dependent kinases, thymidine kinase ("TK"), and other agents useful for interfering with cell proliferation; (c) bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. BMPs are typically dimeric proteins that can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the polyplexes are used to deliver mRNA or non-integrating expression vectors that are expressed transiently in the host cell.

In a preferred embodiment, the polynucleotide is a pro-apoptotic construct, for example an expression vector encoding TNF-related apoptosis-inducing ligand (TRAIL), which is targeted to tumor cells.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule.

The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs).
Pseudocomplementary oligonucleotides can be more efficient and provide increased target site flexibility over methods of induced recombination such as triple-helix oligonucleotides and bis-peptide nucleic acids which require a polypurine sequence in the target double-stranded DNA.

A. In Vivo Methods

The disclosed compositions can be used in a method of delivering polynucleotides to cells in vivo. It has been discovered that the disclosed polymers are more efficient and/or less toxic for systemic in vivo transfection of polynucleotides than alternative transfection reagents includes LIPO-FECTAMINE 2000, PEI, and even other PMSCs. Accordingly, in some embodiments, the cell specific polyplexes including a therapeutic polynucleotide are administered systemically in vivo to a treat a disease, for example cancer.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

1. Pharmaceutical Compositions

Pharmaceutical compositions including nucleic acids and, optionally, polypeptides are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the polyplexes to the immediate area of the implant.

The polyplexes can be provided to the cell either directly, such as by contacting it with the cell, or indirectly, such as through the action of any biological process. For example, the polyplexes can be formulated in a physiologically acceptable carrier or vehicle, and injected into a tissue or fluid surrounding the cell. The polyplexes can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the polyplex-associated nucleic acid administered to an individual will be less than the amount of the unassociated nucleic acid that must be administered for the same desired or intended effect.

2. Formulations for Parenteral Administration

In a preferred embodiment the polyplexes are administered in an aqueous solution, by parenteral injection. As discussed in the Examples below, in some embodiments, a formulation suitable for systemic administration by injection includes glucose.

The formulation can be in the form of a suspension or emulsion. In general, pharmaceutical compositions are provided including effective amounts of nucleic acids optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

3. Formulations for Topical and Mucosal Administration

The polyplexes can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges.

Transdermal formulations may also be prepared. These will typically be ointments, lotions, sprays, or patches, all of which can be prepared using standard technology. Transdermal formulations can include penetration enhancers.

4. Co-Administration

Polyplexes disclosed herein can optionally be co-administered with one or more additional active agents. Co-administration can include the simultaneous and/or sequential administration of the one or more additional active agents and the polyplexes. The one or more additional active agents and the polyplexes can be included in the same or different pharmaceutical formulation. The one or more additional active agents and the polyplexes can achieve the same or different clinical benefit. An appropriate time course for sequential administration may be chosen by the physician, according to such factors as the nature of a patient's illness, and the patient's condition. In certain embodiments, sequential administration includes the co-administration of one or more additional active agents and the nanoparticle gene carriers within a period of one week, 72 hours, 48 hours, 24 hours, or 12 hours.

The additional active agent can be chosen by the user based on the condition or disease to be treated. Example of additional active agents include, but are not limited to, vitamin supplements, nutritional supplements, anti-anxiety medication, anti-depression medication, anti-coagulants, clotting factors, anti-inflammatories, steroids such as corticosteroids, analgesic, etc.

If the disease to be treated is cancer, the polyplexes can be administered to a subject in combination with a chemotherapeutic regime, a radiological treatment, a surgical intervention, or combinations thereof. For example, in some methods, the polyplexes are co-administered with a chemotherapeutic drug or immunostimulatory drug. The disclosed compositions can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1 receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor receptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Other agents that can be administered in combination with polyplexes include PD-1 antagonists such as an anti-B7-H1 antibody or an anti-PD-1 antibody, an anti-CTLA4 antibody, a mitosis inhibitor, such as paclitaxel, an aromatase inhibitor, such as letrozole, an A2AR antagonist, an angiogenesis inhibitor, anthracyclines, oxaliplatin, doxorubicin, TLR4 antagonists, and IL-18 antagonists.

B. In Vitro Methods

The disclosed compositions can be used in a method of delivering polynucleotides to cells in vitro. For example, the polyplexes can be used for in vitro transfection of cells. The method typically involves contacting the cells with polyplex including a polynucleotide in an effective amount to introduce the polynucleotide into the cell's cytoplasm. In some embodiments, the polynucleotide is delivered to the cell in an effective amount to change the genotype or a phenotype of the cell. The cells can primary cells isolated from a subject, or cells of an established cell line. The cells can be of a homogenous cell type, or can be a heterogeneous mixture of different cells types. For example, the polyplexes can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions described herein.

The methods are particularly useful in the field of personalized therapy, for example, to repair a defective gene, de-differentiate cells, or reprogram cells. For example, target cells are first isolated from a donor using methods known in the art, contacted with the polyplexes including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use. In one embodiment, fibroblasts, keratinocytes or hematopoietic stem cells are isolated from a patient and repaired, de-differentiated, or reprogrammed in vitro to provide therapeutic cells for the patient.

C. Diseases to be Treated

Embodiments of the present disclosure provide compositions and methods applicable for gene therapy protocols and the treatment of gene related diseases or disorders. Cell dysfunction can also be treated or reduced using the disclosed compositions and methods. In some embodiments, diseases amenable to gene therapy are specifically targeted. The disease can be in children, for example individuals less than 18 years of age, typically less than 12 years of age, or adults, for example individuals 18 years of age or more. Thus, embodiments of the present disclosure are directed to treating a host diagnosed with a disease, by transfection of the polyplex including a polynucleotide into the cell affected by the disease and wherein the polynucleotide encodes a therapeutic protein. In another embodiment, an inhibitory RNA is directed to a specific cell type or state to reduce or eliminate the expression of a protein, thereby achieving a therapeutic effect. The present disclosure encompasses manipulating, augmenting or replacing genes to treat diseases caused by genetic defects or abnormalities.

Suitable genetic based diseases that can be treated with the compositions disclosed herein include but are not limited to:

Mitochondrial Disease:

Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis;

FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephaloeardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease:

Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease:

Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers:

Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders:

Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome, progerias, SCID.

Autoimmune Disorders:

Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders:

Alopecia, Diastrophic dysplasia, Ellis-van Creveld syndrome, Asthma, Arthritis, including osteoarthritis, rheumatoid arthritis, and spondyloarthropathies.

Age-Related Disorders:

Alzheimer Disease, Parkinson's Disease, Atherosclerosis, Age-Related Macular Degeneration, Age-related Osteoporosis.

The disclosed methods and compositions can also be used to treat, manage, or reduce symptoms associated with aging, in tissue regeneration/regenerative medicine, stem cell transplantation, inducing reversible genetic modifications, expressing inhibitory RNA, cognitive enhancement, performance enhancement, and cosmetic alterations to human or non-human animal.

D. Research Tools

In one embodiment, the present disclosure is used as a tool to investigate cellular consequences of gene expression. Mutant mice can be generated using this approach, allowing investigators to study various biological processes. More particularly, the methods and compositions disclosed herein can be used to generate cells that contain unique gene modifications known in the art and at the discretion of one skilled in the art.

E. Transgenic Non-Human Animals

The techniques described in the present disclosure can also be used to generate transgenic non-human animals. In particular, zygote microinjection, nuclear transfer, blastomere electrofusion and blastocyst injection of embryonic stem (ES) cell hybrids have each provided feasible strategies for creating transgenic animals. In one embodiment an embryonic stem (ES) cell is transfected and injected into the blastocyst of a mammalian embryo as a means of generating chimeric mice. In another embodiment, embryonic stem (ES) cell are first prepared, followed by blastocyst injection into embryos. The use of cells carrying specific genes and modifications of interest allows the creation and study of the consequences of the transfected DNA. In theory, this technique offers the prospect of transferring any polynucleotide into a whole organism. For example, the disclosed methods and compositions could be used to create mice possessing the delivered polynucleotide in a specific cell type or cell state.

Another embodiment of the disclosure provides transfected non-human organisms and methods making and using them. Single or multicellular non-human organisms, preferably non-human mammals, more preferably mice, can be transfected with the compositions described herein by administering the compositions of the present disclosure to the non-human organism. In one embodiment, the polynucleotide remains episomal and does not stably integrate into the genome of the host organism. In another embodiment, the polynucleotide prevents the expression of a gene of interest. Thus, the expression of the polynucleotide in specific cells of the host can be controlled by the amount of polynucleotide administered to the host.

The disclosed transfected non-human organisms have several advantages over traditional transgenic organisms. For example, the transfected organism disclosed herein can be produced in less time that traditional transgenic organisms without sexual reproduction. Moreover, the expression of the polynucleotide of interest in the host can be directly regulated by the amount of polynucleotide of interest administered to the host. Dosage controlled expression of a polynucleotide of interest can be correlated to observed phenotypes and changes in the transfected animal. Additionally, inducible expression and/or replication control elements can be included in the polynucleotide of interest to provide inducible and dosage dependent expression and/or replication. Suitable inducible expression and/or replication control elements are known in the art. Furthermore, the effect of genes and gene modifications in specific cell types and states can be studied without affecting the entire cells of the animal.

F. PEG-Blocking Containing Polymers

The polymers described herein can be used for drug delivery, for example, in the formation of particles, such as microparticles or nanoparticles, or micelles which can release one or more therapeutic, prophylactic, and/or diagnostic agents in a controlled release manner over a desirable period of time.

Various pH-responsive micelle nanocarriers have been investigated previously. Such micelles are often formed via self-assembly of amphiphilic block copolymers and consist of a hydrophilic (e.g. PEG) outer shell and a hydrophobic inner core capable of response to medium pH. Typically, upon changing the medium pH from neutral or slightly basic to mildly acidic, the micelle cores undergo accelerated degradation, become completely soluble in water, or swell substantially in aqueous medium. As the result, the drug-encapsulated micelles with a slow drug-release rate at the physiological pH can be triggered by an acidic pH to rapidly unload the drug molecules. The polymer segments constituting the micelle cores in previous reports include poly(ortho esters), poly($\beta$-amino esters), poly(L-histidine), and others. The major disadvantages with most of the previous micelle systems are the multiple steps required for preparing the copolymers and the difficulty of controlling the polymer molecular weight and adjusting the polymer composition during the copolymer synthesis.

The copolymers described herein exhibited variation in the rate of release as a function of pH. In vitro drug release behaviors of the DTX-encapsulated micelles of PEG2K-PPMS copolymer samples (PEG2K-PPMS-11% PDL, PEG2K-PPMS-30% PDL, and PEG2K-PPMS-51% PDL) were studied in PBS solution at both physiological pH of 7.4 and acidic pH of 5.0. In general, the DTX release from all micelle samples followed biphasic release kinetics and exhibited remarkable pH-dependence. The DTX-loaded PEG2K-PPMS copolymer micelles release 25-45% drug rapidly during the initial 12 h, followed by a more gradual release of additional 25-40% drug for the subsequent 132 h. The influence of the medium pH on the drug release rate is substantial. For example, at the end of the incubation period (144 h), the values of accumulated DTX released from the micelles of PEG2K-PPMS-11% PDL, PEG2K-PPMS-30% PDL, and PEG2K-PPMS-51% PDL copolymers are respectively 66%, 60%, and 55% at physiological pH of 7.4, which increase correspondingly to 85%, 81%, and 75% at acidic pH of 5.0. The observed pH-triggered acceleration of DTX release from the PEG2K-PPMS copolymer micelles is consistent with the earlier observation that changing of the medium pH from 7.4 to 5.0 causes significant swelling of the micelles due to the protonation and size increase of the micelle PPMS cores. This pH-triggered micelle size expansion would certainly facilitate the diffusion and release of entrapped DTX from the micelle cores to the aqueous medium. On the other hand, at a given pH, the DTX release rate is presumably controlled by the interactions between the drug and the PPMS matrix in the micelle cores. Since PDL-rich PEG2K-PPMS copolymers are expected to form strong hydrophobic domains in their micelle inner cores to better trap and retain hydrophobic DTX molecules, the drug release from such copolymer micelles should be more gradual and sustained. This hypothesis is supported by the experimental result showing that at both pH of 7.4 and 5.0, the DTX release rate from PEG2K-PPMS copolymer micelles decreases with increasing PDL content in the PPMS chain segments of the copolymer.

It is known that upon uptake of micelles by tumor cells, the micelle particles are subjected to entrapment in endosomes with pH ranging from 5.5 to 6.0 and in lysosomes with pH ranging from 4.5 to 5.0. As the above results clearly show, these acidic environments would inevitably trigger fast DTX release from PEG2K-PPMS copolymer micelles, thus enhancing the cytotoxicity of the drug-loaded micelles. The amino groups in the copolymers would act as proton sponges to facilitate endosomal escape. Therefore, the pH-responsive properties exhibited by the PEG2K-PPMS copolymer micelles are highly desirable, which render them to be superior carriers for delivery of anticancer drugs.

The cytotoxicity of blank copolymer micelles, DTX-loaded copolymer micelles, and free DTX was evaluated on SK-BR-3 cells at pH of 7.4 using the MTT assay. The blank micelles exhibited no obvious cytotoxicity on SK-BR-3 cells as the cell viabilities of all treated cell groups were over 90%. For example, after treatment with the micelles of PEG2K-PPMS-11% PDL, PEG2K-PPMS-30% PDL, and PEG2K-PPMS-51% PDL copolymers at concentration as high as 200 µg/mL, the three treated cell groups had respectively 97%, 94%, and 90% of the cells remaining viable. As expected, the cell viability decreases with increasing concentration of DTX either in the form of the free drug or in the form of the drug encapsulated in the micelles. To quantify the in vitro efficacy of these micelle formulations, $IC_{50}$ values for DTX-loaded micelles of copolymers PEG2K-PPMS-11% PDL, PEG2K-PPMS-30% PDL, and PEG2K-PPMS-51% PDL were calculated to be 0.57 nM, 0.83 nM, and 1.42 nM, respectively. In comparison, the $IC_{50}$ value for free DTX was found to be 1.27 nM. $IC_{50}$ is defined as the drug concentration of a specific formulation which is required to kill 50% of cells after they are incubated with the drug for a designated time period (48 h). Thus, except the PEG2K-PPMS-51% PDL copolymer micelles, both DTX-loaded PEG2K-PPMS-11% PDL copolymer micelles and DTX-loaded PEG2K-PPMS-30% PDL copolymer micelles possess significantly higher cytotoxicity against SK-BR-3 cells than free DTX. The exceptionally high efficacy observed for DTX-loaded PEG2K-PPMS-11% PDL copolymer micelles is likely attributed to fast cellular uptake of the micelles and anticipated rapid intracellular DTX release from the micelles upon entrapment of the micelle particles in acidic endosomes/lysosomes.

The rate of DTX release from the micelles, particularly pH-triggered acceleration of the drug release, appears to play a more important role than the cellular uptake in influencing the cytotoxicity of the DTX-loaded micelles. Thus, although the cellular uptake is faster for DTX-loaded PEG2K-PPMS-51% PDL copolymer micelles vs. DTX-loaded PEG2K-PDMS-30% PDL copolymer micelles (FIG. 8), the latter micelles release the drug at a higher rate to exert higher cytotoxicity toward SK-BR-3 cells.

The drug-loaded micelle particles were readily absorbed by SK-BR-3 cells and were able to escape from entrapment by endosomes and lysosomes after the cellular uptake. Because of these desirable properties, DTX-loaded micelles prepared from the copolymers described herein (e.g., PEG2K-PPMS-11% PDL and PEG2K-PPMS-30% PDL) with low PDL content, high protonation capability, and fast drug release at an acidic pH exert substantially higher potency against SK-BR-3 cancer cells than free DTX drug. These results demonstrate that copolymer micelles have great potential to serve as pH-responsive nano-carriers for controlled release delivery of anticancer agents, such as DTX, to treat cancers.

G. Kits

Kits or packs that supply the elements necessary to conduct transfection of eukaryotic or prokaryotic organisms, in particular the transfection of specific cell types or cell states are also disclosed. In accordance with one embodiment a kit is provided comprising the disclosed polymers, and optionally a polyplex coating, for example a target specific coating. The polymer can be combined with a polynucleotide of the user's choosing to form a complex which can be used to transfect a host or a host cell. The polyplex can be further mixed with the coating to provide cell-type or cell-state specific tropism.

The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

EXAMPLES

Example 1

Synthesis and Characterization of Poly(Amine-Co-Ester) Terpolymers

Materials and Methods

Materials

ε-Caprolactone (CL, 99%), 12-dodecanolide (DDL, 98%), ω-pentadecalactone (PDL, 98%), 16-hexadecanolide (HDL, 97%), diethyl sebacate (DES, 98%), N-methyldiethanolamine (MDEA, 99+%), N-phenyldiethanolamine (PDEA, 97%), and diphenyl ether (99%) were purchased from Aldrich Chemical Co. and were used as received. Chloroform (HPLC grade), dichloromethane (99+%), hexane (97+%), methanol (98%), and chloroform-d were also obtained from Aldrich Chemical Co.

Immobilized *Candida antarctica* lipase B (CALB) supported on acrylic resin or Novozym 435 (Aldrich Chemical) dried at 50° C. under 2.0 mmHg for 20 h prior to use.

Synthesis and Purification of Lactone-DES-MDEA Terpolymers

The copolymerization of a lactone with a diacid or diester (e.g., diethyl sebacate (DES)), and a dialkyl amine (e.g., N-methyldiethanolamine (MDEA)) was performed in diphenyl ether solution using a parallel synthesizer connected to a vacuum line with the vacuum (±0.2 mmHg) controlled by a digital vacuum regulator. In a typical experiment, reaction mixtures were prepared, which contained three monomers (lactone, DES, and MDEA), Novozym 435 catalyst (10 wt % vs. total monomer), and diphenyl ether solvent (200 wt % vs. total monomer). The copolymerization reactions were carried out at a constant temperature in two stages: first stage oligomerization, followed by second stage polymerization. The reaction temperature was 80° C. for the reactions of ε-caprolactone (CL) with DES and MDEA and was set at 90° C. for the copolymerizations of all other lactones [12-dodecanolide (DDL), 15-pentadecanolide (PDL), and 16-hexadecanolide (HDL)] with DES and MDEA.

During the first stage reaction, the reaction mixtures were stirred under 1 atm of nitrogen gas, after which the reaction pressure were reduced to 1.6 mmHg and the reactions were continued for additional 72 h. The terpolymer products were isolated and purified according to the following procedures.

Because the solubility and physical properties of the terpolymers vary substantially depending on the ring size of the lactones and the lactone unit content in the polymers, two different purification methods were developed to isolate the polymer products. For purification of those polymers that are viscous liquids or waxy solids (e.g., CL-DES-MDEA terpolymers with ≤80% CL, DDL-DES-MDEA terpolymers with ≤40% DDL, PDL-DES-MDEA terpolymers with ≤20% PDL, and HDL-DES-MDEA terpolymers with ≤20% HDL), the crude product mixtures were first mixed with hexane to cause the precipitation of the polymers. The precipitated polymers were then washed several times with fresh hexane to extract and remove the residual diphenyl ether solvent from the polymers. Subsequently, the terpolymers were dissolved in dichloromethane and filtered to remove catalyst particles. Evaporation and complete removal of the $CH_2Cl_2$ solvent from the filtrates at 40° C. under high vacuum (1.0 mmHg) yielded the purified terpolymers.

For purification of the solid lactone-DES-MDEA terpolymers (e.g., DDL-DES-MDEA terpolymers with >40% DDL, PDL-DES-MDEA terpolymers with >20% PDL, and HDL-DES-MDEA terpolymers with >20% HDL), the crude product mixtures were first dissolved in chloroform. The resultant polymer solutions were then filtered to remove the enzyme catalyst. After being concentrated under vacuum, the filtrates were added dropwise to stirring methanol to cause precipitation of the terpolymers. The obtained white solid polymers were subsequently washed with methanol three times and dried at 40° C. under high vacuum (1.0 mmHg) for 16 h. The isolated yield, composition, molecular weight ($M_w$), and polydispersity ($M_w/M_n$) of the synthesized terpolymers are reported in Table 1.

Size Determination of Polyplexes

Size of the polyplexes was determined by Zetasizer (Malvern). The polyplex nanoparticles were placed on a round cover glass mounted on an aluminum stub using carbon adhesive tape. After drying at room temperature, the stub was sputter-coated with a mixture of gold and palladium (60:40) under low pressure of argon using a Dynavac Mini Coater and subjected to SEM analysis.

Determination of Amount of III-20% PDL Polymer Associated with DNA

Figure 6:
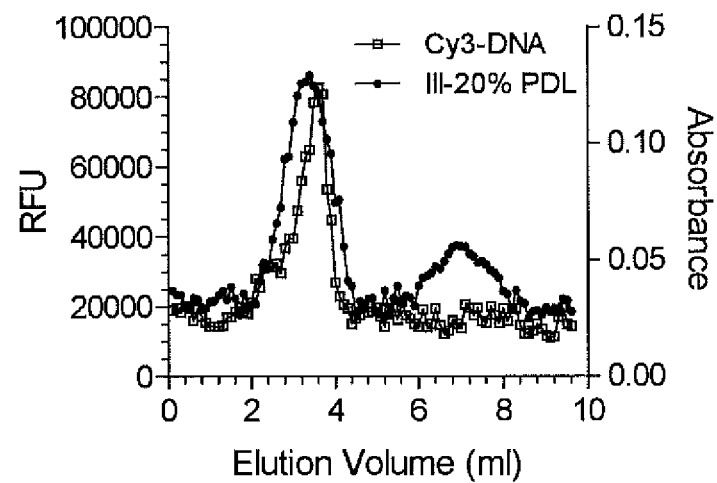
FIG. 6 is a line graph showing RFU and absorbance of elution fractions (elution volume (ml)) following size exclusion chromatography to determine the amount of III-20% PDL polymer associated with or without DNA when mixed with DNA at a 100:1 weight ratio. Elution fractions were monitored for both III-20% PDL polymer (●) and Cy3-DNA (□) content after loading III-20% PDL/Cy3-DNA polyplexes on a Sepharose CL-2B column. Representative data from three separate experiments are shown. The amount of DNA-associated polymer was determined by area under curve analysis.

Size exclusion chromatography was used to determine the amount of III-20% PDL polymer associated with or without DNA when mixed with DNA at a 100:1 weight ratio. Size exclusion chromatography was performed using a Sepharose CL-2B column (14.5×50 mm, 8.3 ml column volume) at a flow rate of 0.4 ml/min. Twenty percentage of N-methyldiethyleneamine in III-20% PDL polymer was replaced with N-phenyldiethyleneamine, which allows sensitive detection of polymer based on UV absorption. Plasmid DNA was labeled with Cy3 Label IT® Tracker™ Intracellular Nucleic Acid Localization Kit (Mirus Bio LLC) following manufacturer's protocol. Columns were pre-conditioned with 100 µg free III-20% PDL to prevent non-specific interactions between the polymer and column. After column equilibration, fractions (0.1 ml) were collected using a phosphate buffered saline (pH 7.4) elution buffer. Elution samples were analyzed by absorbance at 300 nm and spectrofluorescence (ex/em: 550/570). The results are illustrated in FIG. 6. Elution fractions were monitored for both III-20% PDL polymer (●) and Cy3-DNA (□) content after loading III-20% PDL/Cy3-DNA polyplexes on a Sepharose CL-2B column. FIG. 6 shows representative data from three separate experiments. The amount of DNA-associated polymer was determined by area under curve analysis.

Instrumental Methods $^1$H and $^{13}$C NMR spectra were recorded on a Bruker AVANCE 500 spectrometer. The chemical shifts reported were referenced to internal tetramethylsilane (0.00 ppm) or to the solvent resonance at the appropriate frequency.

The number and weight average molecular weights ($M_n$ and $M_w$, respectively) of polymers were measured by gel permeation chromatography (GPC) using a Waters HPLC system equipped with a model 1515 isocratic pump, a 717 plus autosampler, and a 2414 refractive index (RI) detector with Waters Styragel columns HT6E and HT2 in series. Empower II GPC software was used for running the GPC instrument and for calculations. Both the Styragel columns and the RI detector were heated and maintained at 40° C. temperature during sample analysis. Chloroform was used as the eluent at a flow rate of 1.0 mL/min. Sample concentrations of 2 mg/mL and injection volumes of 100 µL were used. Polymer molecular weights were determined based on a conventional calibration curve generated by narrow polydispersity polystyrene standards from Aldrich Chemical Co.

Results

PMSC was shown previously to be an efficient vector for in vitro transfection of cell lines and for direct intratumoral gene delivery in vivo, but was not able to deliver genes after systemic administration. To determine if PMSC chain structures with additional hydrophobic repeat units might lead to more efficient gene vectors a new method for the synthesis of terpolymers from lactone, diethyl sebacate (DES), and N-methyldiethanolamine (MDEA) was developed using *Candida antarctica* lipase B (CALB) as catalyst. CALB is an efficient catalyst for combined ring-opening and condensation copolymerization of lactone with dialkyl diester and conventional diol monomers.

The terpolymerization of DES and MDEA with various ring size lactones was performed in two stages: oligomerization under 1 atmospheric pressure of nitrogen, followed by polymerization at 1.6 mmHg vacuum (FIG. 1). During the initial oligomerization, the monomers were converted to non-volatile oligomers. The subsequent use of high vacuum facilitates removal of the byproduct ethanol, thus accelerating polymer chain growth. This method allowed for the synthesis of novel poly(amine-co-esters) with diverse chain structures and tunable hydrophobicity.

Using this method, lactones in a wide range of ring sizes ($C_4$ to $C_{24}$, preferably $C_6$ to $C_{16}$) can serve as comonomers and the copolymerization reactions were accomplished in one step without protection and deprotection of the amino group of MDEA. Such amino-bearing copolyesters would be extremely difficult to synthesize using conventional organometallic catalysts since metal catalysts are often sensitive to (or deactivated by) organic amines and are known to be inefficient for polymerizing large ring lactone monomers (Stridsberg, et al., Controlled ring-opening polymerization: Polymers with designed macromolecular architecture. Degradable Aliphatic Polyesters 157, 41-65 (2002)) (Nomura, et al. Anionic Ring-Opening Polymerization of Macrocyclic Esters. *Macromolecules* 27, 620-621 (1994)).

Furthermore, enzymatic polymerization catalysis has distinct advantages for producing biomedical polymers due to the high activity and extraordinary selectivity of enzyme catalysts and resultant high purity of products that are also metal-free (DeRouchey, et al. Structural investigations of DNA-polycation complexes. Eur Phys J E Soft Matter 16, 17-28 (2005)). In design of the current polycationic gene carriers, lactone was chosen as one of the comonomers because the hydrophobicity of lactone-DES-MDEA terpolymers could be effectively altered by choosing a lactone with a specific ring-size and/or by adjusting lactone unit content in the terpolymers. In addition, readily available lactones of various ring size are known to possess low toxicity: for example, polyesters derived from small lactones, such as poly(c-caprolactone) and poly(p-dioxanone), are commercial biomaterials and have been used in clinical applications. Large (e.g., $C_{16}$-$C_{24}$) lactones and their polyester derivatives are natural products that were found to be present in several different types of bees.

Table 1, above, shows the yield, composition, molecular weight, polydispersity, and other characterization data of selected lactone-DES-MDEA terpolymers that were prepared as described above. Table 1 includes data from samples that have low solubility in polar organic solvents (e.g., DMSO) and thus were not able to form polyplexes with DNA. To simplify nomenclature, CL-DES-MDEA, DDL-DES-MDEA, PDL-DES-MDEA, and HDL-DES-MDEA terpolymers are designated as polymer I, II, III, and IV, respectively (Table 1A). The composition of each individual terpolymer is further denoted as x % lactone indicating the lactone unit content [mol % vs. (lactone sebacate) units] in the polymer. For example, II-40% DDL and III-20% PDL represent DDL-DES-MDEA copolymer with 40% DDL and PDL-DES-MDEA copolymer with 20% PDL, correspondingly.

The lactone-DES-MDEA terpolymers were obtained in good yields (80-86%) and the composition of the terpolymers were readily controlled by adjusting the corresponding monomer feed ratio (Table 1). The molecular weight ($M_w$) of the polymers ranged from 18000 to 39000 with polydispersity ($M_w/M_n$) between 1.8 and 2.3. Compared to PEI, which contains 32.6 wt % nitrogen, the lactone-DES-MDEA terpolymers had low nitrogen contents (1.9-4.7 wt %). In general, the solubility of lactone-DES-MDEA terpolymer in DMSO decreases with increasing lactone ring size at a given lactone content. Among terpolymers synthesized from a same lactone, solubility in DMSO is lower at a higher lactone content.

The lactone-DES-MDEA terpolymers were characterized by $^1$H and $^{13}$C NMR spectroscopy. The polymer chains consist of three different types of repeat units: lactone, dialkyl amine (e.g., N-methyldiethyelenamine (MDEA)), and a diester (e.g., sebacate) (FIG. 1). Proton NMR spectra were used to measure the composition (repeat unit ratio) of the terpolymers. The repeat unit sequence distributions (diad distributions) in the polymers were analyzed by $^{13}$C NMR spectroscopy and the experimental results were compared to the values calculated for statistically random terpolymers at same compositions. Consistent with the microstructures of PDL-diethyl succinate-1,4-butanediol terpolymers that were prepared previously using the same catalyst, the unit arrangements in lactone-DES-MDEA copolymers were also random. Thus, these polymers can also be described as poly(lactone-co-N-methyldiethyleneamine-co-sebacate).

Because of branching nature of the tertiary amino groups in polymer chains, PMSC was a viscous liquid at ambient temperature. Incorporation of lactone into the poly(amine-co-ester) resulted in lactone-DES-MDEA terpolymers in which the physical properties vary substantially depending on the ring size of the lactone and its content in the polymers. In general, the terpolymers with a small ring lactone and low lactone content are liquids and those with a large lactone and a high lactone content are waxy or solid materials. Thus, I-(10-80) % CL, II-(10-40) % DDL, III-(10-20) % PDL, and IV-10% HDL were viscous liquids at room temperature while II-(60-80) % DDL, II-(40-80) % PDL, and IV-(20-80) % HDL were either semisolid or solid polymers (Table 1).

Synthesis and Purification of Lactone-DES-MDEA Polymers

General procedures for CALB-catalyzed terpolymerization of lactone with DES and MDEA and the procedures for isolation and purification of the formed terpolymer products are described above. The $^1$H and $^{13}$C NMR resonance absorptions of the polymers are shown below. Table 1 summarizes the yield, composition, molecular weight ($M_w$), polydispersity ($M_w/M_n$), and nitrogen content of all purified Lactone-DES-MDEA terpolymers.

CL-DES-MDEA terpolymer (I): $^1$H NMR (CDCl$_3$; ppm) 1.29 (br.), 1.34-1.39 (m), 1.60 (br.), 2.25-2.30 (m), 2.32 (s), 2.67 (t), 4.04 (t), 4.15 (t); $^{13}$C NMR (CDCl$_3$; ppm) 24.48, 24.53, 24.84, 24.89, 25.46, 25.48, 28.32, 29.02-29.06 (m), 33.97, 34.02, 34.15, 34.20, 42.83, 55.91, 61.91, 61.97, 63.92, 64.01, 173.21, 173.31, 173.50, 173.60, plus a small absorption at 14.22 ppm.

DDL-DES-MDEA terpolymer (II): $^1$H NMR (CDCl$_3$; ppm) 1.27-1.29 (br.), 1.61 (m, br.), 2.26-2.31 (m), 2.34 (s), 2.69 (t), 4.05 (t), 4.16 (t); $^{13}$C NMR (CDCl$_3$; ppm) 24.87, 24.91, 24.95, 25.00, 25.93, 28.66, 29.06, 29.08, 29.14, 29.25, 29.27, 29.43, 29.50, 34.21, 34.24, 34.31, 34.35, 42.88, 55.95, 61.95, 64.35, 173.63, 173.68, 173.81, 173.86, plus a small absorption at 14.25 ppm.

PDL-DES-MDEA terpolymer (III): $^1$H NMR (CDCl$_3$; ppm) 1.26-1.29 (br.), 1.61 (m, br.), 2.26-2.32 (m), 2.34 (s), 2.69 (t), 4.05 (t), 4.16 (t), plus a small absorption (triplet) at 3.57 ppm due to —CH$_2$CH$_2$OH end groups; $^{13}$C NMR (CDCl$_3$; ppm) 24.84, 24.90, 24.92, 24.99, 25.92, 28.65, 29.03, 29.07, 29.12, 29.25, 29.28, 29.47, 29.53, 29.58-29.63 (m), 34.13, 34.18, 34.23, 34.28, 42.77, 55.87, 61.86, 64.27, 173.44, 173.50, 173.62, 173.68, plus two small absorptions at 14.22 and 61.58 ppm due to —CO—OCH$_2$CH$_3$ terminal groups.

HDL-DES-MDEA terpolymer (IV): $^1$H NMR (CDCl$_3$; ppm) 1.26-1.29 (br.), 1.60 (m, br.), 2.25-2.31 (m), 2.32 (s), 2.68 (t), 4.05 (t), 4.15 (t); $^{13}$C NMR (CDCl$_3$; ppm) 24.86, 24.91, 24.94, 25.00, 25.92, 28.65, 29.05, 29.07, 29.14, 29.25, 29.28, 29.47, 29.53, 29.59-29.65 (m), 34.18, 34.23, 34.28, 34.34, 42.86, 55.94, 61.94, 64.33, 173.57, 173.64, 173.75, 173.82, plus a small absorption at 14.24 ppm.

Synthesis of Purified PDL-DES-MDEA-PDEA Copolymer

A reaction mixture containing PDL/DES/MDEA/PDEA monomers in a molar ratio of 1:9:7.2:1.8, Novozym 435 catalyst (10 wt % vs. total monomer), and diphenyl ether (200 wt % vs. total monomer) was stirred at 90° C. under 1 atmosphere of nitrogen for 19 h. Subsequently, the reaction pressure was reduced to 1.2 mmHg and the reaction was continued at 90° C. for additional 72 h. The resultant, liquid PDL-DES-MDEA-PDEA copolymer was purified according to a procedure similar to that used for purification of PDL-DES-MDEA terpolymer III-10% PDL as described above. This copolymer consists of four repeat units: PDL, sebacate, N-methyldiethyleneamine, N-phenyldiethyleneamine; and its composition was determined by $^1$H NMR spectroscopy.

PDL-DES-MDEA-PDEA copolymer: yield 87%; 10 mol % PDL vs. (PDL+sebacate); 20 mol % PDEA vs. (MDEA+PDEA); $M_w$=243000; $M_w/M_n$=1.8; $^1$H NMR (CDCl$_3$; ppm): 1.26-1.29 (br.), 1.61 (m, br.), 2.25-2.31 (m), 2.33 (s), 2.68 (t), 3.58 (t, —CH$_2$—CH$_2$—N(Ph)—CH$_2$—CH$_2$—), 4.05 (t), 4.15 (t), 4.22 (t, —CH$_2$—CH$_2$—N(Ph)—CH$_2$—CH$_2$—), 6.69 (t), 6.75 (d), 7.20 (t).

Study on Polymer Chain Growth during Lactone-DES-MDEA

Terpolymerization

Terpolymerization of PDL with DES and MDEA was selected as a typical example for polymer chain growth study. The reaction mixture contained 2:3:3 (molar ratio) PDL/DES/MDEA comonomers, Novozym 435 catalyst (10 wt % vs. total monomer), and diphenyl ether solvent (200 wt % vs. total monomer). The copolymerization reactions were carried out at 60, 70, 80, and 90° C. temperatures in two stages: first stage oligomerization under 1 atmosphere pressure of nitrogen for 19 h, followed by second stage polymerization under 1.4 mm Hg vacuum for 72 h. To monitor the polymer chain growth, aliquots were withdrawn at various time intervals during the second stage polymerization. The formed polymers were then dissolved in HPLC-grade chloroform and filtered to remove the enzyme catalyst. Polymer products were not fractionated by precipitation prior to analysis of molecular weight. The filtrates containing whole products were analyzed by GPC using narrow polydispersity polystyrene standards to measure polymer molecular weights.

Figure 2A:
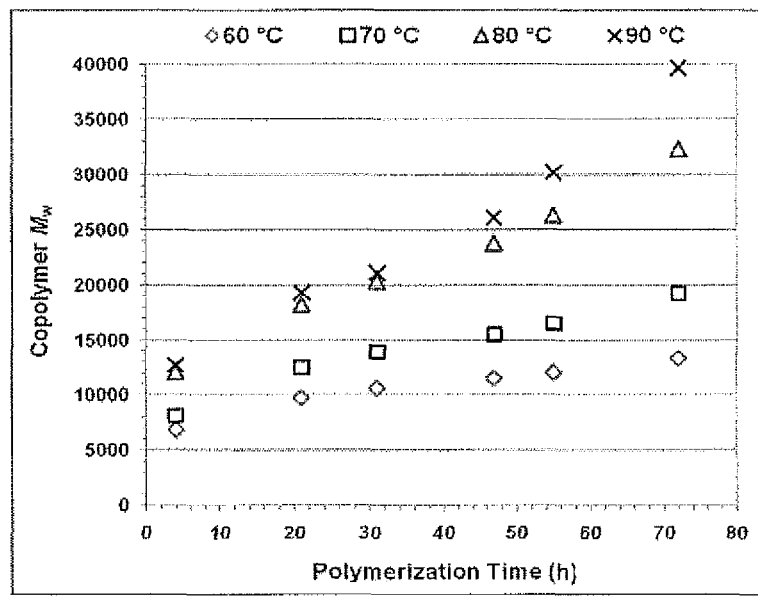
FIGS. 2A and 2B are scatter plots of copolymer $M_w$ over polymerization time (hours), and $M_w/M_n$ over copolymer $M_w$, respectively, illustrating variations of product molecular weight and polydispersity during copolymerization of PDL with DES and MDEA at different temperatures ($\diamond$=60° C., $\square$=70° C., $\Delta$=80° C., and X=90° C. Polymerization conditions: 2:3:3 (molar ratio) PDL/DES/MDEA, 1.4 mmHg pressure.
Figure 2B:
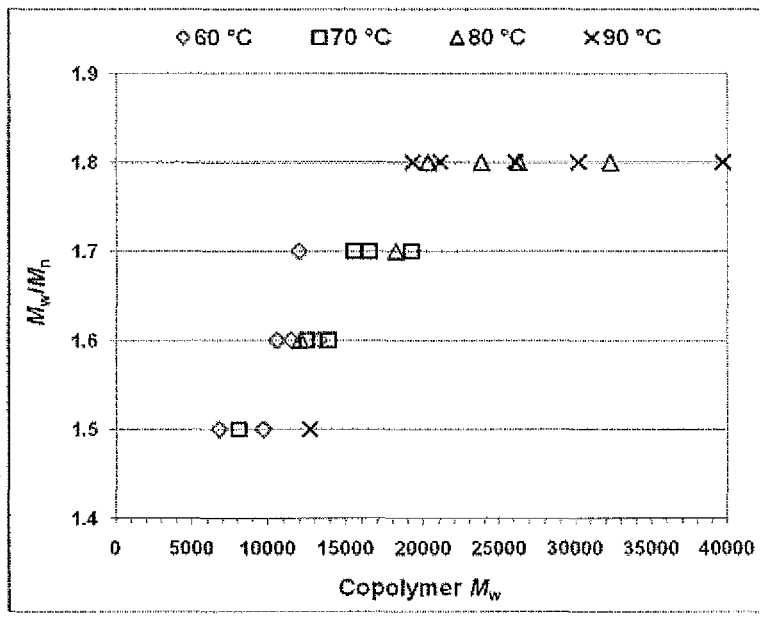

FIG. 2 shows the changes in polymer molecular weight ($M_w$) vs. polymerization time for the copolymerization at different temperatures. For all reactions, continuous chain growth was observed during the 72 hour polymerization period. For example, at 4, 21, 31, 47, 55, 72 h, the products formed at 90° C. had $M_w$ values of 12700, 19300, 21100, 26100, 30200, and 39700, respectively. Among these reactions, the copolymer molecular weight at a given reaction time was found to increase with increasing reaction temperature from 60 to 90° C. Thus, at 72 h, the resultant copolymers of the reactions at 60, 70, 80, and 90° C. possessed $M_w$ values of 13300, 19200, 32300, and 39700, correspondingly. These results indicate that the molecular weight of the PDL-DES-MDEA terpolymers could be readily controlled by adjusting the reaction time and/or reaction temperature. The product polydispersity ($M_w/M_n$) vs. molecular weight ($M_w$) for the copolymerization reactions is delineated in FIG. 2B. The polydispersity values of all products follow a similar trend, which changed from 1.5 to 1.7 with increasing polymer molecular weight ($M_w$) from 6800 to 19000, and remained fairly constant at 1.8 in the molecular weight range between 19000 and 40000. Furthermore, NMR analysis showed that during the copolymerization reactions, byproduct ethanol was formed and condensed in the dry ice trap between the reactors and vacuum pump.

To determine whether the polymerization reactions were indeed catalyzed by CALB, control experiments were performed without the lipase. The control reaction was carried out at 90° C. in diphenyl ether under identical conditions (stage 1: 2:3:3 PDL/DES/MDEA monomer ratio, under 1 atmosphere pressure of nitrogen for 19 h; stage 2: 1.4 mmHg for 72 h). GPC analysis showed that the product had a $M_w$ of less than 800. This demonstrates that CALB catalyzes lactone-DES-MDEA terpolymerization.

Structural Characterization of Lactone-DES-MDEA Terpolymers

The lactone-DES-MDEA terpolymers were characterized by $^1H$ and $^{13}C$ NMR spectroscopy. The polymer chains consist of three different types of repeat units: lactone, N-methyldiethanolamine (MDEA), and sebacate (FIG. 1). Proton NMR spectra were used to measure the composition (repeat unit ratio) of the terpolymers. The repeat unit sequence distributions (diad distributions) in the polymers were analyzed by $^{13}C$ NMR spectroscopy and the experimental results were compared to the values calculated for statistically random terpolymers at same compositions. Consistent with the microstructures of PDL-diethyl succinate-1,4-butanediol terpolymers that were prepared previously using the same catalyst, the unit arrangements in lactone-DES-MDEA copolymers were also random (Jiang, Z. Lipase-catalyzed synthesis of aliphatic polyesters via copolymerization of lactone, diallyl diester, and diol. Biomacromolecules 9, 3246-3251 (2008)) (Mazzocchetti, et al. Enzymatic Synthesis and Structural and Thermal Properties of Poly(omega-pentadecalactone-co-butylene-co-succinate). Macromolecules 42, 7811-7819 (2009)). Thus, these polymers can also be described as poly(lactone-co-N-methyldiethyleneamine-co-sebacate).

The structure and composition of the lactone-DES-MDEA terpolymers were determined by $^1H$ and $^{13}C$ NMR spectroscopy. NMR resonance absorptions were assigned by comparing signals of the terpolymers to those of reference polymers, poly(lactone) homopolymers and poly(N-methyldiethyleneamine sebacate) (PMSC), and by observing changes in signal intensities among the terpolymers synthesized from various lactone/DES/MDEA monomer feed ratios.

The proton NMR spectra of the lactone-DES-MDEA terpolymers showed that the copolymers contained three different types of repeating units: lactone, N-methyldiethyleneamine, and sebacate. The molar ratios of lactone to N-methyldiethyleneamine to sebacate units in the terpolymers were calculated from proton resonance absorptions: number of lactone units from methylene absorption at 4.05 (±0.01) ppm, number of N-methyldiethyleneamine units from absorptions at 4.15 (±0.01) or 2.68 (±0.01) ppm, and number of sebacate units from absorption at 1.60 (±0.01) ppm after subtracting contribution from lactone units.

The above structural assignments for the terpolymers I-IV were further supported by the $^{13}C$ NMR spectra of the polymers. All terpolymers exhibited four ester carbonyl resonance absorptions at 173.2-173.9 ppm due to two diads of lactone unit and two diads of sebacate unit. For terpolymers II, III, and IV that contain large ($\geq C_{12}$) lactone units, the four resonance peaks with decreasing chemical shift are attributable to lactone*-lactone, sebacate*-lactone, lactone*-MDEA, and sebacate*-MDEA diads, respectively. For CL-DES-MDEA terpolymer (or terpolymer I), the carbon-13 absorbances at 173.60, 173.50, 173.31, and 173.21 ppm are ascribable to CL*-MDEA, sebacate*-MDEA, CL*-CL, and sebacate*-CL diads, correspondingly. Furthermore, for terpolymers H, III, and IV, the —$CH_2O$— group of the lactone units and the —$CH_2O$— group of the MDEA units resonated at 64.3 (±0.05) and 61.9 (±0.05) ppm, respectively.

It was found that increasing lactone content in the polymers resulted in higher resonance intensity at 64.3 ppm, but lower absorbance intensity at 61.9 ppm. However, terpolymer I showed four resonance absorptions of the —$CH_2O$— groups at 64.01, 63.92, 61.97, and 61.91 ppm, which are attributable to CL*-CL, CL*-sebacate, MDEA*-CL, and MDEA*-sebacate diads, correspondingly. In support of this structural assignment, it was observed that increasing CL content in terpolymer I increases the absorption intensity at 64.01 ppm, but decreases the absorption intensity at 61.91 ppm. On the other hand, the intensities of the two resonances at 63.92 and 61.97 ppm were comparable regardless of the polymer composition. For all four terpolymers, the resonance absorptions of the methyl and methylene groups adjacent to the nitrogen in MDEA units appeared at 42.8 (±0.08) and 55.9 (±0.05) ppm, respectively.

To determine the repeat unit sequence distributions in the terpolymers, the abundance of lactone*-lactone (L*-L), lactone-MDEA (L*-M), sebacate*-lactone (S*-L), and sebacate*-MDEA (S*-M) diads in the polymers was measured by $^{13}C$ NMR spectroscopy and the obtained experimental values were then compared to theoretical diad distribution values calculated for random copolymers with same compositions. For a completely random lactone-DES-MDEA terpolymer, distributions of L*-L, L*-M, S*-L, and S*-M diads can be calculated by the following equations:

$$L\text{*-}L \text{ distribution} = f_L \times f_L$$

$$L\text{*-}M \text{ distribution} = f_L \times (2f_M)$$

$$S\text{*-}L \text{ distribution} = (2f_S) \times f_L$$

$$S\text{*-}M \text{ distribution} = (2f_S) \times (2f_M)$$

where $f_L$, $f_S$, $f_M$ are correspondingly molar fractions of L, S, and M repeating units in the terpolymers. It needs to be noted that in the above formulae, molar fractions of S and M units are doubled because both ends of the units can form an ester linkage of a diad, while only one end of L units can serve the purpose. Table 2 summarizes the measured diad distributions of terpolymers I, II, III, and IV with different compositions, as well as the values calculated for random copolymers. For all copolymers studied, the experimental values match remarkably well with the calculated values. Thus, the lactone-DES-MDEA terpolymers synthesized using CALB catalyst contain lactone, sebacate, and N-methyldiethyleneamine repeat units randomly distributed in the polymer chains, and can be described as poly(lactone-co-N-methyldiethylenamine-co-sebacate). These results are consistent with previous reports showing that enzymatic PDL-diethyl succinate-1,4-butanediol terpolymers also possessed random chain structures (Jiang, Z. Lipase-catalyzed synthesis of aliphatic polyesters via copolymerization of lactone, dialkyl diester, and diol. *Biomacromolecules* 9, 3246-3251 (2008)).

TABLE 2

Diad Distributions of Lactone-DES-MDEA Terpolymers: Comparison between Experimental Values and Theoretical Values Calculated for Random Copolymers

| Polymer[a] | L/S/M[b] (unit ratio) | L*-L meas[c] | L*-L calc[d] | L*-M meas[c] | L*-M calc[d] | S*-L meas[c] | S*-L calc[d] | S*-M meas[c] | S*-M calc[d] |
|---|---|---|---|---|---|---|---|---|---|
| I-20% CL | 20:80:80 | 0.01 | 0.01 | 0.10 | 0.10 | 0.10 | 0.10 | 0.80 | 0.79 |
| I-40% CL | 40:60:60 | 0.06 | 0.06 | 0.19 | 0.19 | 0.19 | 0.19 | 0.56 | 0.56 |
| I-60% CL | 60:40:40 | 0.18 | 0.18 | 0.25 | 0.25 | 0.25 | 0.25 | 0.33 | 0.33 |
| I-80% CL | 80:20:20 | 0.45 | 0.45 | 0.22 | 0.22 | 0.22 | 0.22 | 0.11 | 0.11 |
| II-20% DDL | 20:80:80 | 0.02 | 0.01 | 0.11 | 0.10 | 0.11 | 0.10 | 0.76 | 0.79 |
| II-40% DL | 40:60:60 | 0.06 | 0.06 | 0.20 | 0.19 | 0.20 | 0.19 | 0.54 | 0.56 |
| II-60% DDL | 60:40:40 | 0.18 | 0.18 | 0.25 | 0.25 | 0.25 | 0.25 | 0.32 | 0.33 |
| II-80% DDL | 80:20:20 | 0.46 | 0.45 | 0.22 | 0.22 | 0.22 | 0.22 | 0.10 | 0.11 |
| III-40% PDL | 40:60:60 | 0.06 | 0.06 | 0.18 | 0.19 | 0.20 | 0.19 | 0.56 | 0.56 |
| III-82% PDL | 82:18:18 | 0.48 | 0.48 | 0.22 | 0.21 | 0.20 | 0.21 | 0.10 | 0.09 |
| IV-20% HDL | 20:80:80 | 0.01 | 0.01 | 0.10 | 0.10 | 0.11 | 0.10 | 0.78 | 0.79 |
| IV-40% HDL | 40:60:60 | 0.06 | 0.06 | 0.19 | 0.19 | 0.20 | 0.19 | 0.55 | 0.56 |
| IV-61% HDL | 61:39:39 | 0.18 | 0.19 | 0.25 | 0.25 | 0.25 | 0.25 | 0.32 | 0.32 |
| IV-80% HDL | 80:20:20 | 0.45 | 0.44 | 0.23 | 0.22 | 0.23 | 0.22 | 0.09 | 0.11 |

[a]See Table 1 for meanings of the polymer abbreviations.
[b]Unit abbreviations: L for lactone; S for sebacate; M for N-methyldiethyleneamine.
[c]Measured from $^{13}$C NMR spectra.
[d]Calculated for a copolymer with statistically random unit distribution in the polymer chains.

Example 2

Terpolymers are Effective for Gene Delivery In Vitro

Materials and Methods

In Vitro Transfection and Characterization

Human embryonic kidney 293 (HEK293) cell line and lung cancer cell line A549 were obtained from ATCC (American Type Culture Collection). Cells were grown in DMEM medium (Invitrogen) supplemented with 10% fetal bovine serum (Invitrogen), 100 units/ml penicillin, and 100 μg/ml streptomycin (Invitrogen) in a 37° C. incubator containing 5% $CO_2$. For in vitro transfection, DNA polyplexes with weight ratio of 100:1 were used unless otherwise noted. Polymers were dissolved in DMSO at 25 mg/ml.

For preparing DNA polyplexes for transfection in 24 well plates, 4 μl of polymer solution (25 mg/ml in DMSO) was first diluted in 50 μl sodium acetate buffer (25 mM, pH=5.2). After brief vortexing, the polymer solution was mixed with the same volume of a DNA solution containing 1 μg DNA and vortexed for additional 10 seconds. The polymer/DNA mixture was incubated at room temperature for 10 min and then added to cells, which were seeded in 24-well plates at density of 75,000 cells/well in 500 μl of medium one night before transfection. Transfection using Lipofectamine 2000 (Invitrogen Corp.) was performed using the procedures provided by the manufacturer. PEI transfection was performed using the standard protocol by keeping the weight ratio of PEI to DNA at 3. The same amount of DNA was used in experiments comparing lactone-DES-MDEA terpolymer with Lipofectamine 2000 and PET.

For luciferase gene transfection, plasmid DNA expression luciferase, pGL4.13 (Promega) was used. Two days after transfection, the culture medium was removed and the cells were washed with cold PBS. Two hundred micro-liter Report Lysis Buffer (Promega) was added to each well. With a freeze-thaw cycle, cell lysate was collected. After a quick spin, 20 μl was subjected to luciferase assay using Luciferase Assay Reagent according to the standard protocol described in manufacturer manual (Promega). Additional 25 μl was used to quantify protein content using Pierce BCA protein assay kit (Pierce, Thermo Scientific). Luciferase signal was divided by the amount of total protein for comparison. Internal controls were used for normalization for group by group comparison. For experiments to detect cytotoxicity due to TRAIL, plasmid pEGFP-TRAIL (Kagawa, et al. Antitumor activity and bystander effects of the tumor necrosis factor-related apoptosis-inducing ligand (TRAIL) gene. Cancer Res 61, 3330-3338 (2001)) (Addgene) was used. Control plasmid, pEGFP, was obtained by removing TRAIL gene from pEGFP-TRAIL. Cell proliferation was determined by a standard MTT assay five days after transfection. The particle size and zeta potential of freshly prepared polyplexes were measured by ZetaPals dynamic light scattering (Brookhaven Instruments Corp). The morphology of polyplexes, which was stained with uranyl acetate, was visualized using FEI Tencai Biotwin TEM at 80 Kv. Images were taken using Morada CCD and iTEM (Olympus) software.

Results

Figures 3A, 3B, 3C, 3D:
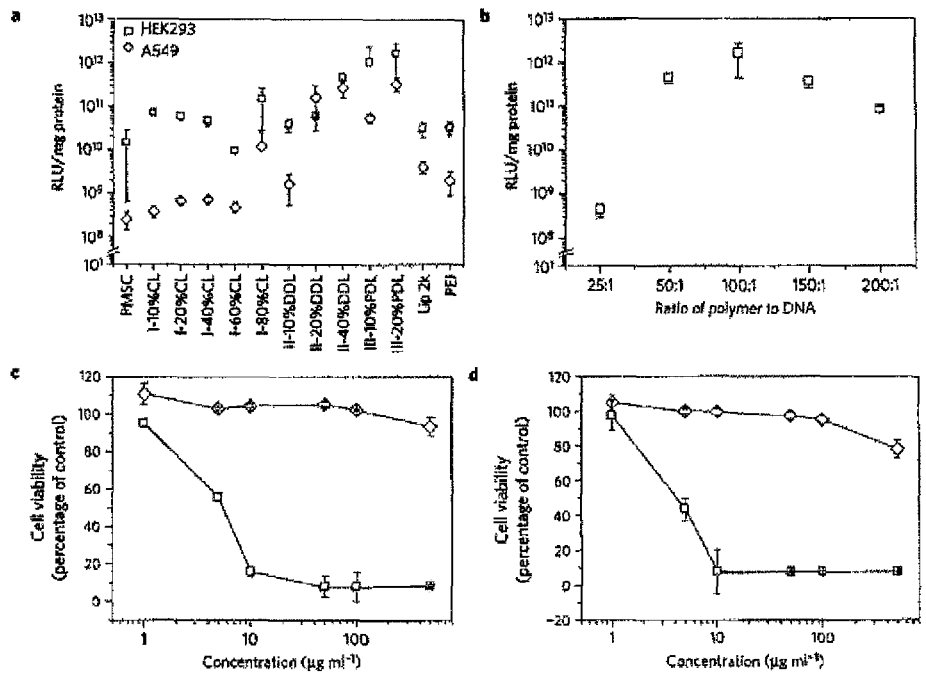
FIG. 3A is a graph showing the gene deliver efficiency (RLU/mg protein) of various terpolymers (as labeled) on HEK293 cells ($\square$) and A549 cells ($\diamond$).
FIG. 3B is a scatter plot showing the effect of III-20% PDL to DNA ratio (ratio of polymer to DNA) on transfection efficiency on HEK293 cells (RLU/mg protein).
FIG. 3C is a line graph showing cell viability (percentage of control) as a function of PEI ($\square$) or III-20% PDL ($\diamond$) concentration ($\mu$g ml$^{-1}$) on HEK293 cells.
FIG. 3D is a line graph showing cell viability (percentage of control) as a function of PEI ($\square$) or III-20% PDL ($\diamond$) concentration ($\mu$g ml$^{-1}$) on A549 cells.

All liquid terpolymers were evaluated for luciferase gene transfection on HEK293 and A549 cells. Gene transfection efficiency increased with increasing lactone content for both terpolymer II and III (FIG. 3A). Thus, II-40% DDL transfected A549 cells with an efficiency that is 2, 162, and 1047 times higher than that of II-20% DDL, II-10% DDL, and PMSC, respectively. On the other hand, III-20% PDL was 6 and 1259 time more efficient than III-10% PDL and PMSC, respectively, in transfecting A549 cells (FIG. 3A). A similar trend was observed for transfecting HEK293 cells (FIG. 3A). Although group I terpolymers in general were more effective gene carriers than PMSC, the correlation between their transfection efficiency and lactone (CL) content does not follow a simple, consistent trend as observed for terpolymers II and III. Lactone ring size also significantly affects the gene delivery performance of the terpolymers. At a given lactone content, terpolymers with long chain lactone units deliver genes with higher efficiency than those with short chain lactone units. For example, the efficiency of HEK293 cell transfection was 27 times higher for III-10% PDL vs. II-10% DDL, and was 27 times higher for III-20% PDL vs. II-20% DDL (FIG. 3A). Similar lactone size effects were observed for the transfection of A549 cells (FIG. 3A). These results demonstrate that gene transfection efficiency of lactone-DES-MDEA terpolymers can be improved by using a large lactone and by adjusting lactone content in the polymers. The remarkable effects of lactone ring size and lactone unit content on gene transfection performance of lactone-DES-MDEA terpolymers support our hypothesis that hydrophobicity plays an important role in influencing transfection efficiency of cationic polymers.

Among all terpolymers evaluated, III-20% PDL showed the best gene delivery. Terpolymer III with a higher PDL content (e.g., III-40% PDL and III-60% PDL) and lactone-DES-MDEA terpolymers with a larger lactone (e.g., group IV terpolymers) had low solubility in polar organic solvents (e.g., DMSO), and were not able to form polyplexes in aqueous solution. Despite the fact that III-20% PDL has lower nitrogen density than PMSC (Table 3), the optimal polyplex composition for gene delivery was the same (at 100:1 weight ratio of polymer to DNA) for both polymers (FIG. 3B) (Kafil, et al. Cytotoxic Impacts of Linear and Branched Polyethylenimine Nanostructures in A431 Cells. BioImpacts 1, 23-30 (2011)).

TABLE 3

Physical properties of polyplex nanoparticles formed from DNA (pGL4.13) and lactone-DES-MDEA terpolymer

| Polymer name* | N/P** (molar ratio) | Mean particle radius (nm) | Zeta potential (mV) |
|---|---|---|---|
| PMSC*** | 116 | 70 | 15.7 |
| I-10% CL | 111 | 73 | 11.3 |
| I-20% CL | 105 | 107 | 10.8 |
| I-40% CL | 91 | 45 | 15.3 |
| I-60% CL | 72 | 43 | 16.7 |
| I-80% CL | 45 | 117 | 7.3 |
| II-10% DDL | 107 | 69 | 10.4 |
| II-20% DDL | 99 | 93 | 11.6 |
| II-40% DDL | 79 | 90 | 8.9 |
| III-10% PDL | 106 | 86 | 13.2 |
| III-20% PDL | 96 | 75 | 8.9 |
| IV-10% HDL | 105 | — | — |

*See Table 1 for polymer nomenclature.
**All polyplex nanoparticles were formed at 100:1 weight ratio (polymer/DNA).
***PMSC is included here as a reference polymer.

Figure 4:
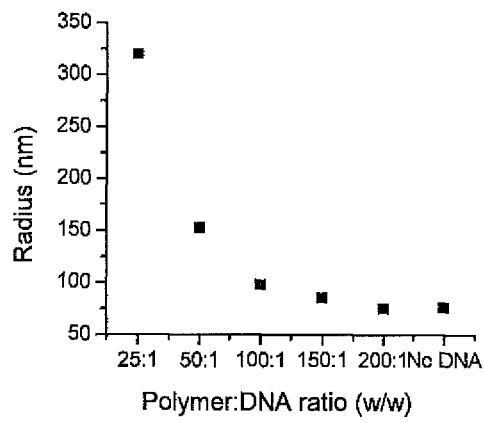
FIG. 4 is a graph showing the size of III-20% PDL/DNA complexes (radius) with different polymer-to-DNA ratios (Polymer:DNA ratio w/w).
Figure 5:
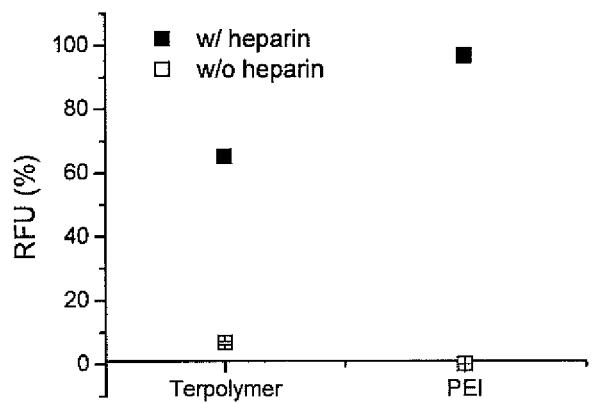
FIG. 5 is a graph showing release of DNA (relative fluorescence unit (RFU) (%)) from III-20% PDL/DNA complexes ("terpolymer") and PEI/DNA complexes ("PEI") with (■) and without (□) heparin. Heparin was added to polyplexes solution with a final concentration of 2% w/v. The values are expressed as a percentage of the fluorescence obtained with naked DNA. Each value is the mean of duplicates.
Figure 7:
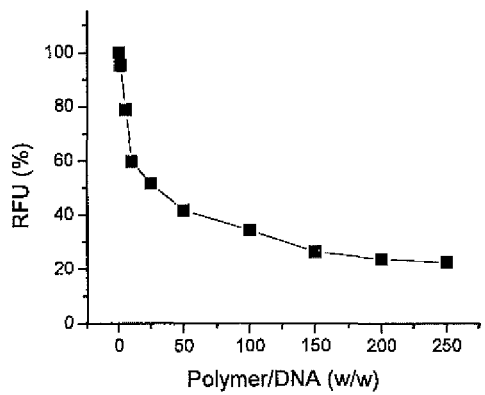
FIG. 7 is a line graph showing RFU (%) as a function of polymer/DNA (w/w) in an ethidium bromide exclusion assay using III-20% PDL. The values are expressed as a percentage of the fluorescence relative (RFU) to the initial fluorescence without polymer.
Figure 8:
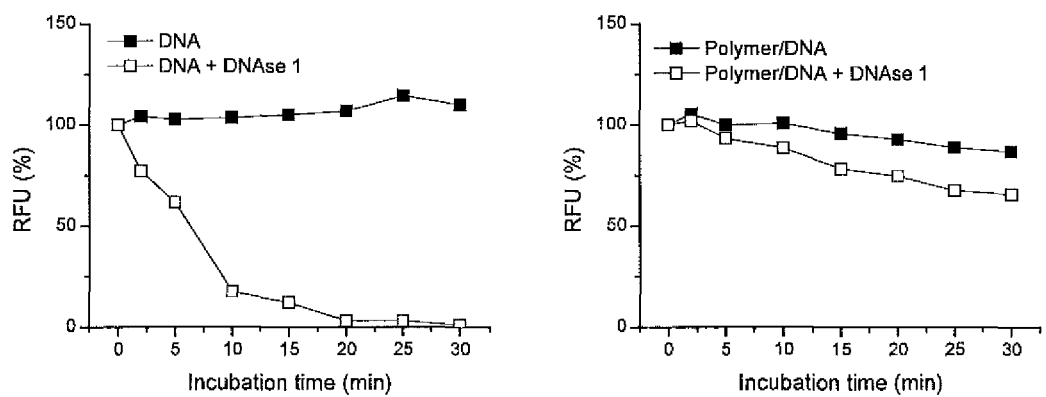
FIG. 8 is two line graphs showing (RFU (%)) of naked DNA (A) or III-20% PDL/DNA complexes (B) with (□) or without (■) DNase degradation at 37° C. at various time points (incubation time (min)). Residual DNA was quantified using PICOGREEN (Invitrogen). The values are expressed as a percentage of the fluorescence obtained at time 0 min.

There was a dramatic increase in transfection efficiency between particles with 25:1 and 50:1 polymer to DNA ratio, which potentially can be explained by the difference in size of these complexes (FIG. 4). A polymer to DNA ratio of 100:1 was selected for all subsequent experiments: at this ratio, nanoparticle complexes are spherical in shape as determined by both TEM and SEM. III-20% PDL/DNA complexes are more stable than traditional polyplexes, such as PEI/DNA complexes: incubation of complexes in 2% heparin released 65% of DNA from III-20% PDL/DNA complexes, compared to 97% for PEI/DNA complexes (FIG. 5). In a typical III-20% PDL/DNA suspension, 80% of III-20% PDL is associated with DNA (FIG. 6). Due to the low charge density and predominantly hydrophobic composition of III-20% PDL, the terpolymer that is not associated with DNA is water insoluble, so the rest of the 20% of terpolymer is likely present as particulates (FIG. 6). Further experiments demonstrated that III-20% PDL with 100:1 polymer to DNA ratio was sufficient to condense DNA (FIG. 7) and protect DNA from enzymatic degradation (FIG. 8).

At the 100:1 weight ratio, III-20% PDL transfected A549 cells with 81 and 166 times higher efficiency than Lipofectamine 2000 and PEI, respectively. For transfection of HEK293 cells, III-20% PDL was ~50 times more efficient than Lipofectamine 2000 and PEI (FIG. 3A). However, under conditions that allow optimal transfection efficiency, Lipofectamine 2000 and PEI are toxic. Incubation of complexes of DNA with Lipofectamine 2000 at the optimal transfection conditions in this study inhibited cell proliferation by over 50%. PEI has similar toxicity. For this reason, Lipofectamine and PEI are normally used to transfect cells only at high confluence, where sufficient numbers of cells can survive. III-20% PDL is much less toxic than Lipofectamine and PEI (FIGS. 3C and 3D). PEI killed all cells three days after treatment at 10 µg/ml. In contrast, III-20% PDL was non-toxic even at concentrations as high as 500 µg/ml (FIGS. 3C and 3D).

Example 3

Terpolymers are Effective for Gene Delivery In Vivo

Materials and Methods

Preparation of Coated Polyplexes for In Vivo Evaluations

To prepare polyplexes for in vivo gene delivery, 40 µl polymer solution in DMSO (50 mg/ml) was diluted to 40 µl NaAc buffer. After brief vortexing, the polymer solution was mixed with 80 µl NaAc buffer containing 0.25 mg/ml plasmid DNA, followed by a vigorous vortex for 10 second. Coating polyplexes with peptide polyE-mRGD was conducted 10 min after incubation at room temperature, by adding 40 µl buffer containing peptide at 2.5 mg/ml and allowing further incubation for 5 min. Peptide polyE-mRGD (EE-EEEEEEEEEEEEEEE-GGGGGG-RGDK (SEQ ID NO:1)) was synthesized at the W. M. Keck Facility at Yale University. Immediately before injection, another 40 µl buffer containing 30% glucose was added. Two hundred microliter of the resulted mixture was then injected through tail vein of each mouse.

To test the effect of serum of polyplex surface change, polyplexes were prepared by mixing polymer and DNA and incubating at room temperature for 10 min. Then, polyE-mRGD was added at various concentrations and coating allowed for 5 min. The zeta potential of the coated polyplexes was determined 5 min after their incubation in NaAc buffer containing 10% FBS.

Measurement of Cellular Uptake

Cell internalization of III-20% PDL/Cy3-DNA polyplexes was monitored using flow cytometry. HEK293 cells were incubated with III-20% PDL/Cy3-DNA polyplexes using the same conditions as the transfection procedure. After incubating for 4 h at either 37° C., cells were washed with PBS and harvested using enzyme-free cell dissociation buffer (Gibco). Cells were washed with 1% BSA in PBS and then analyzed on a BD Biosciences FACScan. To quantify cell association with coated and uncoated polyplexes HEK293 cells were incubated for 4 hours with III-20% PDL/Cy3-DNA polyplexes coated with various polyE-mRGD densities.

Results

Figures 13A, 13B, 13C, 13D:
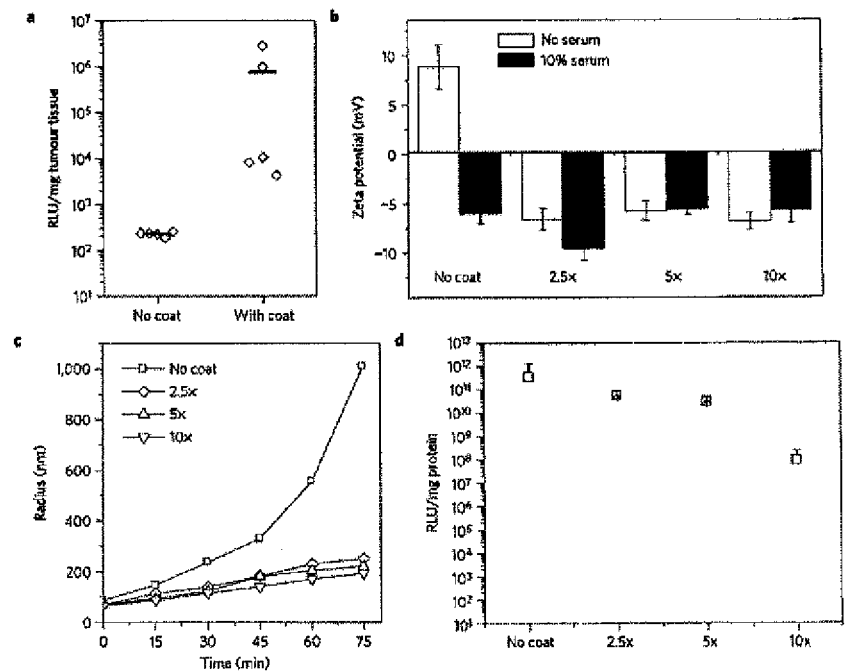
FIG. 13A is a scatter plot comparing in vivo luciferase expression of a construct delivered by polyE-mRGD coated (with coat) and uncoated (no coat) polyplexes transfection. Polyplexes were administrated through tail vein injection and luciferase expression was determined 48 h after the last treatment of three consecutive daily treatments.
FIG. 13B is a bar graph showing the zeta potential (mv) of polyplexes with no coat, or 2.5×, 5×, or 10× coating of polyE-mRGD in the presence (shaded bars) or absence (open bars) of 10% serum.
FIG. 13C is a line graph showing the size (radius (nm)) of polyplexes with no coat (□), or 2.5× (◇), 5× (Δ), or 10× (∇) coating of polyE-mRGD determined by dynamic light scattering at various time intervals.
FIG. 13D is a dot plot showing the gene delivery efficiency (RLU/mg protein) for polyplexes with no coat, or 2.5×, 5×, or 10× coating of polyE-mRGD.

Because of its excellent transfection capability and low toxicity, III-20% PDL was tested for in vivo gene therapy by injection into mice bearing A549-derived tumor xenografts. First, polyplexes of III-20% PDL terpolymer with luciferase plasmid (pLucDNA) was administered through the tail vein: this treatment resulted in limited expression of luciferase in the tumors (no coat, FIG. 13A). It was possible that low gene delivery efficiency was caused by 1) the positive charges on the polyplex surface (the zeta potential of the polyplex: +8.9 mV) (FIG. 13B), which attracts and binds with negatively charged plasma proteins in the blood during circulation, leading to its rapid clearance by the reticuloendothelial system (RES) and 2) the instability of the polyplex nanoparticles. As evidence of instability, polyplex particles incubated in NaAc buffer solution containing 10% serum nearly doubled in size within 15 minutes and increased by over 10-fold after 75 minutes (FIG. 13C). As the result of this increase in size, polyplexes might be cleared from the circulation by uptake in the liver.

To improve in vivo gene delivery the surface of III-20% PDL/pLucDNA polyplexes was modified by coating the particles with polyE-mRGD, a synthetic peptide containing three distinct segments. The first segment is a 16-(amino acid) polyglutamic acid (polyE), which is negatively charged at physiological pH and, therefore, capable of electrostatic binding to the positively charged surface of the polyplexes. The second segment is a 6-unit neutral polyglycine, which serves as a neutral linker. The third segment is the amino acid sequence arginine-glycine-aspartic acid-lysine (RGDK, mRGD), which includes the RGD sequence that binds the tumor endothelium through the interaction of RGD with $\alpha_v\beta_3$ and $\alpha_v\beta_5$. In addition, R/KxxR/K allows binding to neuropilin-1 (Sugahara, et al. Tissue-penetrating delivery of compounds and nanoparticles into tumors. Cancer Cell 16, 510-520 (2009)) (Teesalu, et al. C-end rule peptides mediate neuropilin-1-dependent cell, vascular, and tissue penetration. Proc Natl Acad Sci USA 106, 16157-16162 (2009)). Bindings with integrins and neuropilin-1 can improve tumor-targeted and tissue-penetrating delivery to tumors in vivo. Similar approaches have been reported to facilitate ligand-specific, gene delivery in vitro and targeted gene delivery to liver, spleen, and bone marrow in vivo (Green, et al. Electrostatic ligand coatings of nanoparticles enable ligand-specific gene delivery to human primary cells. Nano Lett 7, 874-879 (2007)). (Harris, et al. Tissue-specific gene delivery via nanoparticle coating. Biomaterials 31, 998-1006 (2010)). Coating with polyE-mRGD reversed the surface charge of III-20% PDL/pLucDNA polyplex (FIG. 13B): when polyE-mRGD was added at 5:1 peptide/DNA weight ratio, the zeta potential of the polyplex changed from +8.9 mV to −5.8 mV.

Peptide coated polyplexes were stable upon incubation in NaAc buffer containing 10% serum (FIG. 13B) and resistant to aggregation (FIG. 13B), indicating that the modified polyplexes can escape clearance by RES during circulation in vivo. Resistance to aggregation is particularly important, because small particle size limits clearance by liver and maintains transfection ability of polyplex particles at the tumor site. It was observed that overcoating of III-20% PDL/pLucDNA polyplex significantly decreased transfection (FIG. 13D), despite our observation that uptake efficiency for overcoated (10×) polyplexes was not reduced in comparison to optimally coated (5×) particles (FIG. 9). On the basis of these results, the ratio of peptide to DNA at 5:1 was selected for the subsequent in vivo studies.

Compared with the uncoated polyplex particles, intravenous administration of coated III-20% PDL/pLucDNA polyplexes exhibited ~14,000 times higher gene expression in tumor (FIG. 13A).

Example 4

Terpolymers can Mediate Transfection of Cancer Cells and Inhibit Cancer Growth In Vivo PolyE-mRGD coated polyplex particles of III-20% PDL with therapeutic DNA were tested for their ability to deliver genes and inhibit tumor growth in vivo. It is well known that tumor necrosis factor-related apoptosis-inducing ligand (TRAIL) can preferentially kill malignant tumor cells, inhibit tumor related angiogenesis, but not harm normal cells (Kagawa, et al. Antitumor activity and bystander effects of the tumor necrosis factor-related apoptosis-inducing ligand (TRAIL) gene. Cancer Res 61, 3330-3338 (2001)) (Matsubara, et al. Gene therapy with TRAIL against renal cell carcinoma. Mol Cancer Ther 5, 2165-2171 (2006)) (Cantarella, et al. TRAIL inhibits angiogenesis stimulated by VEGF expression in human glioblastoma cells. Br J Cancer 94, 1428-1435 (2006)). In addition to direct tumor cell killing via transfection, FRAIL is also known to induce apoptosis in adjacent tumor cells due to a bystander effect (Kagawa, et al. Antitumor activity and bystander effects of the tumor necrosis factor-related apoptosis-inducing ligand (TRAIL) gene. Cancer Res 61, 3330-3338 (2001)). For this reason, a construct containing a fused TRAIL-GFP segment, pEGFP-TRAIL, was chosen as a therapeutic agent. III-20% PDL/pEGFP-TRAIL polyplexes were prepared, coated with polyE-mRGD, and then injected via tail vein in animals bearing tumors (Kagawa, et al. Antitumor activity and bystander effects of the tumor necrosis factor-related apoptosis-inducing ligand (TRAIL) gene. Cancer Res 61, 3330-3338 (2001)).

Figures 11A, 11B, 11C, 11D, 11E, 11F:
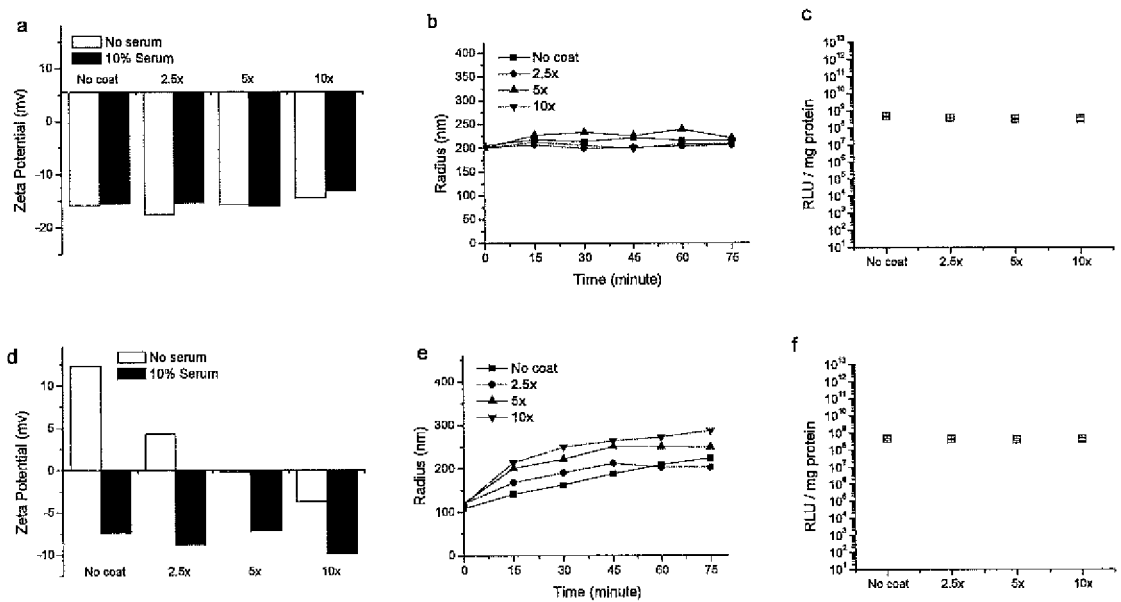
FIGS. 11A and 11D are bar graphs showing the zeta potential (my) of Lip2k/DNA complexes (A) or PEI/DNA complexes (D) with no coat, or 2.5×, 5×, or 10× coating of polyE-mRGD in the presence (shaded bars) or absence (open bars) of 10% serum.
FIGS. 11B and 11E are line graphs showing the radius (nm) of Lip2k/DNA complexes (B) or PEI/DNA complexes (E) with no coat (■), or 2.5× (●), 5× (▲), or 10× (▼) coating of polyE-mRGD.
FIGS. 11C and 11F are dot plots showing the gene delivery efficiency (RLU/mg protein) for Lip2k/DNA complexes (C) or PEI/DNA complexes (F) with no coat, or 2.5×, 5×, or 10× coating of polyE-mRGD.
Figures 14A, 14B, 14C:
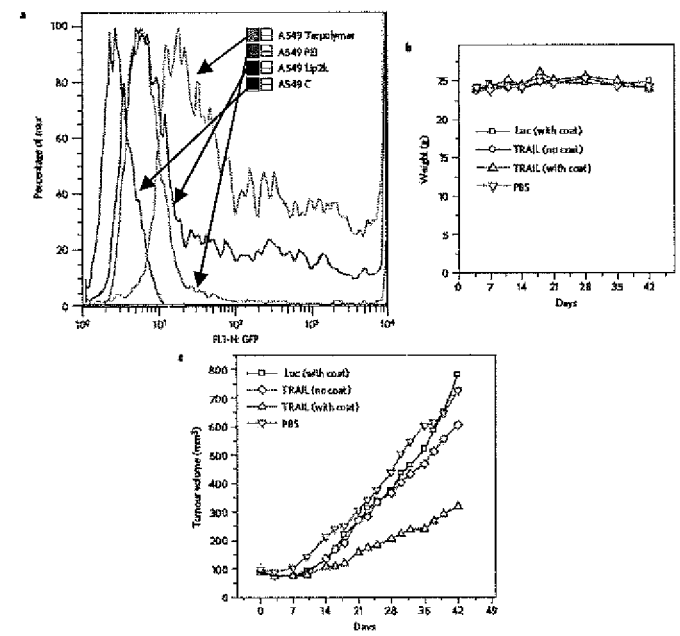
FIG. 14A is a histogram showing the results of flow cytometry analysis of A549 cells 2 days after transfection with four pg of pEGFP plasmid DNA, using III-20% PDL, Lipofectamine 2000 and PEI.
FIG. 14B is a line graph showing weight (grams) of mice during a time course of tail vein administration of PBS control (∇), or III-20% PDL polyplexes with Luc with polyE-mRGD coat (□), TRAIL no coat (○), or TRAIL with polyE-mRGD coat (A) three days a week, at a dose of 1.7 mg per mouse (based on the maximum dosage of polymer that can be used in 200 $\mu$l buffer), for 6 weeks.
FIG. 14C is a line graph showing tumor volume (mm$^3$) of tumor on mice during a time course of tail vein administration of PBS control (∇), or III-20% PDL polyplexes with Luc with polyE-mRGD coat (□), TRAIL no coat (◊), or TRAIL with polyE-mRGD coat (Δ) three days a week, at a dose of 1.7 mg per mouse (based on the maximum dosage of polymer that can be used in 200 μl buffer), for 6 weeks.

In preliminary in vitro studies, III-20% PDL complexed with pEGFP delivered the gene with an efficiency significantly higher than that of Lipofectamine 2000 or PEI (FIG. 14A). Cytotoxicity due to TRAIL was efficiently achieved in vitro by III-20% PDL/pEGFP-TRAIL polyplexes: three days after transfection, proliferation of A549 cells was inhibited by 58%, compared with cells treated with a vector control. In contrast, treatments with Lipofectamine/TRAIL and PEI/TRAIL complexes inhibited cell proliferation by only 21% and 9%, respectively (FIG. 10). In addition, 5× coating, which was selected as the optimal for our in vivo study, did not coat Lipofectamine/DNA complexes and was insufficient to coat PEI/TRAIL complexes (FIG. 11).

Figure 12:
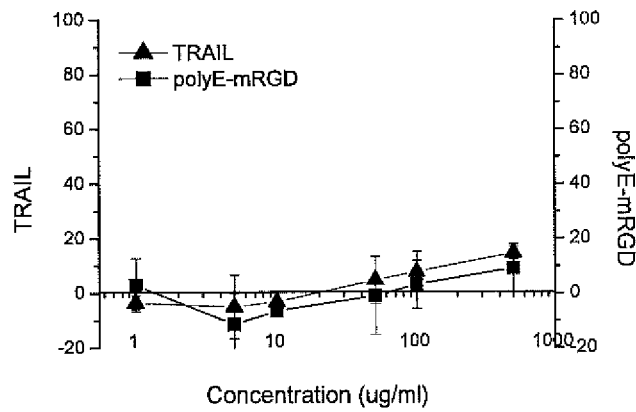
FIG. 12 is a line graph showing the toxicity of naked DNA (▲) and polyE-mRGD (■) on A549 cells at the indicated concentrations. Toxicity was determined five days after treatment by standard MTT assay.

For in vivo tumor treatment, polyE-mRGD coated III-20% PDL/pEGFP-TRAIL polyplexes were administrated three times a week for six weeks at a dose of 1.7 mg per mouse. During the entire course of treatment, no toxicity—as measured by weight loss, for example—was observed (FIG. 14B). Treatment of polyE-mRGD coated III-20% PDL/pEGFP-TRAIL polyplexes significantly inhibited tumor growth. By the end of the experiment, the average tumor size in the mouse group treated with the coated TRAIL polyplex was ~300 mm$^3$, which was significantly smaller than the average tumor size for the groups treated with control polyplexes (polyE-mRGD coated III-20% PDL/pLuc) or PBS, which were ~700 mm$^3$ (p<0.05, one-way ANOVA) (FIG. 14C). Histochemical analysis by TUNEL staining revealed a significant increase in the number of apoptotic cells after treatment with TRAIL (FIG. 14D). The tumor inhibition activity of coated III-20% PDL/pEGFP-TRAIL polyplexes was not due to either naked DNA or polyE-mRGD, since independently, both of them exhibited limited toxicity (FIG. 12).

Example 5

Synthesis and Purification of Poly(Ethylene Glycol)-Poly(ω-Pentadeca Lactone-Co-N-Methyldiethyleneamine-Co-Sebacate) (PEG-PPMS) Block Copolymers The block copolymers were synthesized via copolymerization of ω-pentadecalactone (PDL), diethyl sebacate (DES), and N-methyldiethanolamine (MDEA) using MeO-PEG-OH as the chain-terminating agent and Novozym 435 as the catalyst. The molar ratios of the comonomers and the PEG substrates are reported in Table 4. The amount of MeO-PEG-OH with Mn of 5000 Da or 2000 Da (PEG5K or PEG2K) was selected to form PEG-PPMS block copolymers with approximately 40 wt % PEG upon complete conversion of the feeds. The PDL content in the PPMS blocks of the copolymers is controlled by adjusting the molar ratio of PDL/DES/MDEA comonomers. Thus, PDL, DES, MDEA, and PEG5K or PEG2K in various ratios (Table 4) were blended with Novozym 435 (10 wt % vs. total substrates) and diphenyl ether solvent (200 wt % vs. total substrates) to form reaction mixtures.

All copolymerization reactions were carried out in two stages: first stage oligomerization at 90° C. under 1 atm pressure of nitrogen gas for 20 h, and second stage polymerization at 90° C. under 1.4 mmHg vacuum for 72 h. At the end of the reactions, n-hexane was added to the product mixtures to precipitate the resultant copolymers. The obtained crude products were then washed with fresh n-hexane twice to extract and remove the residual diphenyl ether solvent in the polymers. Subsequently, the copolymers were dissolved in chloroform and were filtered to remove the catalyst particles. Complete evaporation and removal of the of the chloroform solvent from the filtrates at 30° C. under high vacuum (<0.5 mmHg) overnight yielded the purified block copolymers.

The data on polymer yield, molecular weight, and composition are summarized in Table 4.

PEG-PPMS block copolymer: 1H NMR (CDCl3; ppm) 1.26-1.30 (br.), 1.61 (m, br.), 2.26-2.32 (m), 2.34 (s), 2.70 (t), 3.64 (s), 4.05 (t), 4.16 (t); 13C NMR (CDCl$_3$; ppm) 24.84, 24.90, 24.93, 24.99, 25.92, 28.64, 29.04, 29.07, 29.13, 29.25, 29.28, 29.47, 29.53, 29.58-29.63 (m), 34.16, 34.21, 34.27, 34.32, 42.79, 55.87, 61.86, 64.32, 70.54, 173.55, 173.61, 173.74, 173.80.

At the end of the reactions, all formed polymer products prior to purification showed mono-modal molecular weight distributions and no un-reacted MeO-PEG-OH was detected by GPC. During the copolymerization, the amino group of MDEA does not require protection and deprotection steps owning to the high tolerance of the enzyme catalyst towards the tertiary amine functionality.

The molecular structures of the PEG-PPMS block copolymers were characterized by both 1H and 13C NMR spectroscopy. Consistent with block copolymer structures, the copolymer NMR spectra exhibited resonance absorptions (e.g., singlet proton resonance at 3.64 ppm and carbon-13 resonance at 70.54 ppm) due to poly(ethylene glycol) segments in addition to the absorbances attributable to random poly(ω-pentadecalactone-co-N-methyldiethyleneamine-co-sebacate) chains. No other resonance signals were observed. The PDL contents in PPMS chain blocks of the copolymers were calculated from the copolymer $^1$H NMR spectra according to the method reported previously. The PEG contents in the block copolymers were measured by comparing the intensity of the proton resonance at 3.64 ppm vs. the intensities of the other proton absorbances due to the repeat units of PPMS blocks. The random distribution of PDL, MDEA, and sebacate units in the PPMS chain segments was confirmed by $^{13}$C NMR spectroscopy analysis. Such random structures are desirable for drug delivery purposes since micelles made of PEG-PPMS block copolymers with random PPMS chains allow encapsulation and even distribution of drug molecules in the micelle cores to minimize burst release of the drug during delivery.

The PEG-PPMS block copolymers with different compositions were prepared and successfully purified in good yield (up to 90%). During the polymer syntheses, the PEG block length were varied from 2000 Da to 5000 Da. Table 4 summarizes the characterization data on the purified copolymers. The results show that both PEG and PDL contents in the copolymers can be readily controlled by adjusting the feed ratios employed during the copolymerization reactions. All synthesized block copolymers contained approximately 40 wt % PEG (Table 4) since the screening studies indicated that at this PEG content, PEG-PPMS block copolymers readily

TABLE 1

Characterization of The Purified PEG-PPMS Block Copolymers Synthesized Using Different Feed ratios

| Sample[a] | Feeds (mmol) | | | | Polymer Yield (%) | $M_w^b$ | $M_w/M_n^b$ | PEG Content (wt %) | PDL Content (mol %)[c] |
|---|---|---|---|---|---|---|---|---|---|
| | MeO-PEG-OH | PDL | DES | MDEA | | | | | |
| PEG2K-PPMS-11% PDL | 0.675 | 0.73 | 6.58 | 6.24 | 79 | 10400 | 1.7 | 42 | 11 |
| PEG2K-PPMS-20% PDL | 0.690 | 1.53 | 6.12 | 5.77 | 80 | 11000 | 1.8 | 42 | 20 |
| PEG2K-PPMS-30% PDL | 0.705 | 2.36 | 5.50 | 5.14 | 80 | 10800 | 2.0 | 42 | 30 |
| PEG2K-PPMS-40% PDL | 0.715 | 3.25 | 4.88 | 4.52 | 75 | 11500 | 1.8 | 42 | 40 |
| PEG2K-PPMS-51% PDL | 0.725 | 4.26 | 4.26 | 3.90 | 81 | 11600 | 1.8 | 42 | 51 |
| PEG5K-PPMS-10% PDL | 0.270 | 0.73 | 6.58 | 6.44 | 85 | 23100 | 1.6 | 42 | 10 |
| PEG5K-PPMS-20% PDL | 0.276 | 1.53 | 6.12 | 5.98 | 85 | 24500 | 1.5 | 42 | 20 |
| PEG5K-PPMS-30% PDL | 0.282 | 2.36 | 5.50 | 5.36 | 87 | 25200 | 1.5 | 42 | 30 |
| PEG5K-PPMS-41% PDL | 0.286 | 3.25 | 4.88 | 4.73 | 80 | 23900 | 1.5 | 42 | 41 |
| PEG5K-PPMS-50% PDL | 0.290 | 4.14 | 4.14 | 4.00 | 90 | 27200 | 1.6 | 42 | 50 |

[a]PEG2K-PPMS copolymer and PEG5K-PPMS copolymer represent PEG-PPMS block copolymers consisting of 2000 Da and 5000 Da PEG chain segments, respectively. Both PEG2K-PPMS and PEG5K-PPMS copolymers are denoted with x mol % PDL indicating the content of PDL units vs. (PDL + sebacate) units in the PPMS blocks.
[b]Measured by GPC.
[c]Mol % PDL units vs. (PDL + sebacate) units in the PPMS chain segments calculated from the $^1$H NMR spectra.

formed stable micelles in aqueous medium (details regarding the micelle stability are discussed in a latter section).

Because MeO-PEG-OH can only link to the ends of PPMS chains, the PEG-PPMS copolymers have two possible types of block structures: PEG-PPMS diblock chains and/or PEG-PPMS-PEG triblock chains. The PEG5K-PPMS and PEG2K-PPMS copolymers at ~40 wt % PEG content should have molecular weight values of approximately 12500 Da and 5000 Da respectively if the synthesized copolymers are primarily diblock copolymers, but would possess molecular weights of approximately 25000 Da and 10000 Da correspondingly if the copolymers are primarily triblock copolymers. The observed molecular weight ($M_w$) values of 23000 to 27000 Da for the PEG5K-PPMS copolymers and the values of 10000 to 12000 Da for the PEG2K-PPMS copolymers indicate that these block copolymers are substantially rich in PEG-PPMS-PEG triblock chain structures.

Thermal Characterization

Figures 15A, 15B:
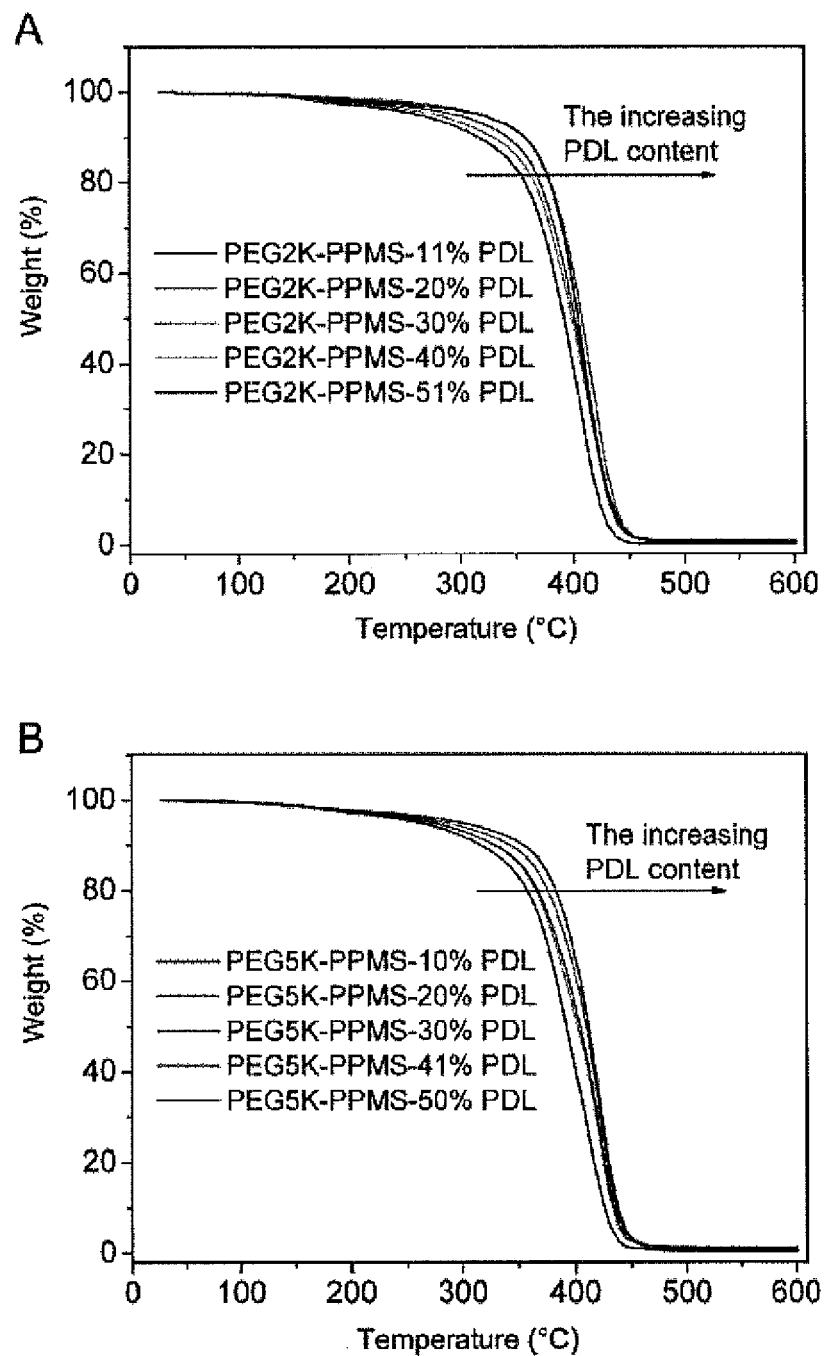
FIGS. 15A and 15B are thermogravimetric curves of the PEG2K-PPMS (A) and PEG5K-PPMS (B) copolymers with different PDL contents.

The thermal stability of the PEG-PPMS block copolymers was investigated by thermogravimetric analysis (TGA). The weight loss curves of the copolymers are depicted in FIG. 15 and the copolymer thermal degradation data are shown in Table 5. The copolymers are thermally stable up to 300° C., start to degrade at about 360° C., and undergo essentially complete thermal degradation at approximately 440° C. The temperature at the maximal degradation rate (Tmax) is in the range of 408-421° C. for PEG2K-PPMS copolymers and of 413-424° C. for PEG5K-PPMS copolymers. It is noticeable that for either PEG2K-PPMS or PEG5K-PPMS copolymers, Tmax gradually increases with increasing PDL content in the polymers (Table 5).

melting transitions at a high PDL content are possibly associated with the crystallites formed by PPMS chain segments in the copolymers. Previous results show that poly(ω-pentadecalactone-co-N-methyldiethyleneamine-co-sebacate) copolymer with a low (10-20%) PDL content is liquid at 25° C. and does not have a melting point above ambient temperature.

Example 6

Preparation of Blank and DTX-Loaded PEG-PPMS Micelles

The micelles were fabricated using a dialysis method. In a typical experiment, 38 mg of PEG-PPMS copolymer with or without docetaxel (DTX, 2 mg) was dissolved in 1 mL of THF in a sealed vial. The micellization was then induced by continuously adding the organic solution into 10 mL of PBS (0.01 M, pH=7.4) using a syringe. The resultant mixture was stirred at room temperature for 10 min and was subsequently dialyzed with a dialysis membrane (MWCO 3,500 Da) against 1 L of PBS (0.01 M, pH=7.4) overnight at ambient temperature. To remove the un-entrapped drug, the micelle solutions were placed in ultrafiltration centrifuge tubes (MWCO 100 kDa) and were centrifuged for 30 min at 5000 rpm. The obtained ultrafiltrates were used for subsequent studies.

For DTX-encapsulated PEG-PPMS micelles, the drug loading and entrapment efficiency were determined by HPLC

TABLE 2

Thermal Properties of The PEG-PPMS Block Copolymers

| Sample[a] | TGA Analysis[b] | | | DSC Analysis | |
|---|---|---|---|---|---|
| | $T_o$ (° C.) | $T_f$ (° C.) | $T_{max}$ (° C.) | $T_m$ (° C.)[c] | $T_g$ (° C.)[d] |
| PEG2K-PPMS-11% PDL | 366 | 430 | 408 | 43.3 | |
| PEG2K-PPMS-20% PDL | 365 | 436 | 413 | 42.3 | |
| PEG2K-PPMS-30% PDL | 369 | 435 | 413 | 44.0 | |
| PEG2K-PPMS-40% PDL | 374 | 439 | 417 | 47.5 | 54.0 |
| PEG2K-PPMS-51% PDL | 376 | 443 | 421 | 47.2 | 59.2 |
| PEG5K-PPMS-10% PDL | 361 | 434 | 413 | 53.0 | |
| PEG5K-PPMS-20% PDL | 363 | 436 | 420 | 53.2 | 27.6 |
| PEG5K-PPMS-30% PDL | 366 | 438 | 420 | 52.1 | 33.6 |
| PEG5K-PPMS-41% PDL | 372 | 440 | 423 | 53.8 50.1 | 34.4 |
| PEG5K-PPMS-50% PDL | 375 | 442 | 424 | 54.2 50.4 | 37.9 |

[a]See Table 1 for the meaning of the abbreviated sample names.
[b]$T_o$, $T_f$, and $T_{max}$ represent the starting degradation temperature, final degradation temperature, and the temperature at the maximum degradation rate, respectively.
[c]$T_m$: melting temperature.
[d]$T_g$: glass transition temperature.

Figures 16A, 16B:
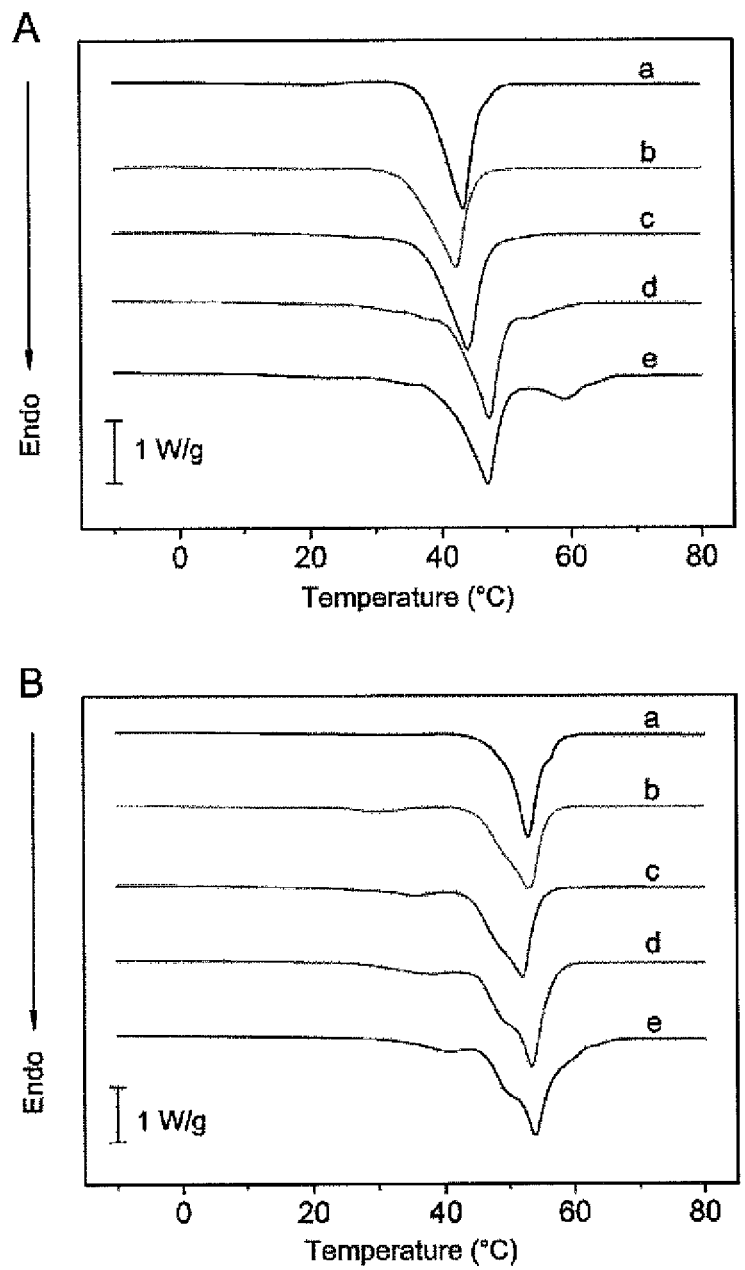
FIGS. 16A and 16B are DSC heating curves of (A) PEG2K-PPMS copolymers with different PDL contents: (a) 11% PDL, (b) 20% PDL, (c) 30% PDL, (d) 40% PDL, (e) 51% PDL; and (B) PEG5K-PPMS copolymers with different PDL contents: (a) 10% PDL, (b) 20% PDL, (c) 30% PDL, (d) 41% PDL, (e) 50% PDL.

As shown in FIG. 15 and Table 5, the effects of PEG chain block length on the PEG-PPMS copolymer thermal degradation are minimal. The melting behaviors of the copolymers were studied by DSC. The obtained DSC curves from the second heating runs are displayed in FIG. 16, and the melting temperatures ($T_m$)/glass transition temperatures ($T_g$) of all samples are summarized in Table 5. The DSC results show that all PEG-PPMS copolymers, are semicrystalline materials and several samples possess more than one melting temperature due to the block structures of the polymers. The major melting events at 43-47° C. for PEG2K-PPMS copolymers and those at 53-54° C. for PEG5K-PPMS copolymers are attributable to the PEG crystallites in the copolymers, which are molecular weight dependent with longer PEG chains increasing the melting temperature. The other weaker (Agilent 1260, USA) equipped with a C18 chromatographic column at 30° C. using 50:50 (v/v) acetonitrile/water mixed solvent as the mobile phase. The mobile phase flow rate was maintained at 1.0 mL/min. In a typical procedure, 50 μL of the above micelle solutions in PBS were diluted in 1 mL of THF and 20 μL of the resultant mixtures were injected to the HPLC during the analyses. The amount of DTX was quantitatively measured by a UV detector at 230 nm wavelength. 30 The drug loading and entrapment efficiency in micelles are calculated according to the following equations:

$$\text{Drug loading (\%)} = \frac{\text{drug amount in micelles}}{\text{mass of micelles}} \times 100\%$$

-continued $$\text{Entrapment efficiency (\%)} = \frac{\text{drug amount in micelles}}{\text{drug feeding}} \times 100\%$$

Characteristics of the DTX-Loaded PEG-PPMS Copolymer Micelles

Docetaxel (a typical anticancer drug) was encapsulated into PEG-PPMS copolymer micelles using a dialysis method. The average size, polydispersity index (PDI), zeta-potential, drug loading, and entrapment efficiency for all DTX-loaded micelles are summarized in Table 6. The average sizes of the micelles are dependent on the copolymer composition. 34 The DTX-loaded micelles of all PEG5K-PPMS copolymers were larger than 300 nm (Table 6).

is anticipated that hydrophilic chain segments (e.g., PEG) in the outer shell of the micelles can shield the charges in the micelle core with the long chain blocks being more effective in reducing zeta potential than the short chain blocks. Thus, significantly lower zeta potential values were observed for PEG5K-PPMS copolymer micelles as compared to PEG2K-PPMS copolymer micelles (Table 6).

The drug loading and entrapment efficiency for the DTX-loaded micelles of PEG2K-PPMS and PEG5K-PPMS copolymers were determined by HPLC analysis (Table 6). The DTX entrapment efficiency for PEG2K-PPMS copolymer micelles ranges from 46% to 60%, which increases with increasing PDL content in the copolymer. This is expected since the PDL-rich block copolymers would form more hydrophobic micelle cores, thus attracting more hydrophobic

TABLE 3

Characteristics of The DTX-loaded PEG-PPMS Copolymer Micelles

| Copolymer[a] | Size (nm) | Zeta[b] (mV) | PDI | Drag loading (%) | Entrapment efficiency (%) |
|---|---|---|---|---|---|
| PEG2K-PPMS-11% PDL | 192 ± 3 | −8.2 ± 0.6 | 0.204 | 2.25 ± 0.04 | 45.8 ± 0.7 |
| PEG2K-PPMS-20% PDL | 184 ± 1 | −8.5 ± 1.4 | 0.164 | 2.31 ± 0.10 | 47.1 ± 2.1 |
| PEG2K-PPMS-30% PDL | 180 ± 3 | −8.7 ± 2.1 | 0.166 | 2.34 ± 0.05 | 47.8 ± 1.0 |
| PEG2K-PPMS-40% PDL | 174 ± 6 | −10 ± 0.6 | 0.201 | 2.61 ± 0.10 | 53.2 ± 2.0 |
| PEG2K-PPMS-51% PDL | 166 ± 3 | −8.5 ± 1.0 | 0.168 | 2.92 ± 0.01 | 60.0 ± 0.2 |
| PEG5K-PPMS-10% PDL | 404 ± 45 | −2.5 ± 0.2 | 0.592 | 1.77 ± 0.02 | 36.1 ± 0.4 |
| PEG5K-PPMS-20% PDL | 319 ± 10 | −1.5 ± 0.1 | 0.473 | 1.37 ± 0.06 | 27.9 ± 1.3 |
| PEG5K-PPMS-30% PDL | 442 ± 25 | −1.7 ± 0.2 | 0.372 | 0.94 ± 0.04 | 19.2 ± 0.8 |
| PEG3K-PPMS-41% PDL | 343 ± 23 | −1.1 ± 0.2 | 0.172 | 0.47 ± 0.04 | 9.5 ± 0.9 |
| PEG5K-PPMS-50% PDL | 355 ± 17 | −1.6 ± 0.2 | 0.149 | 0.43 ± 0.02 | 8.7 ± 0.4 |

[a]See Table 1 for the meaning of the abbreviated sample names.
[b]Measured in PBS solution (0.01M, pH = 7.4).

Figures 17A, 17B:
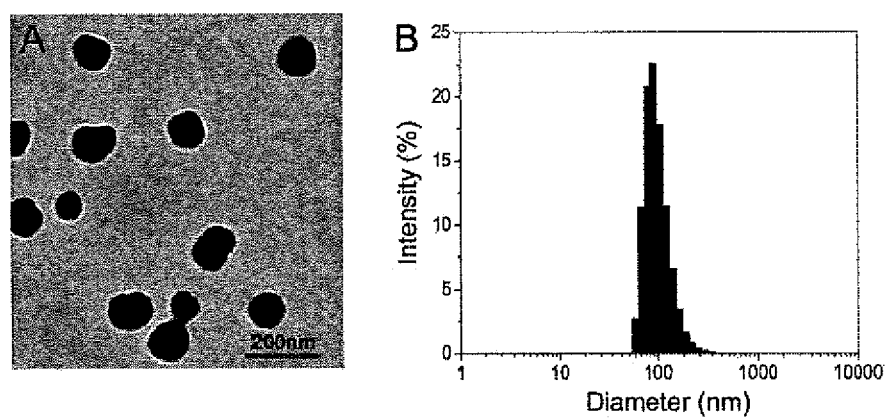
FIG. 17A is a TEM image (A) and FIG. 17B is a graph showing the particle size distribution (B) of DTX-loaded PEG2K-PPMS-30% PDL copolymer micelles.

In comparison, the average sizes of the PEG2K-PPMS copolymer micelles were between 160 and 200 nm, which are attributable to the shorter PEG2K-PPMS copolymer chains vs. their counterparts PEG5K-PPMS copolymer chains. The TEM micrograph and size distribution of the DTX-loaded micelles prepared from PEG2K-PPMS copolymer with 30% PDL content in the PPMS blocks are shown in FIG. 17. Image analysis of the TEM micrograph indicated that the micelles possessed 100-150 nm particle sizes with a narrow size distribution. The DTX-loaded micelles were well dispersed and were nearly spherical in shape. There are no significant differences in morphology among the micelles made from the PEG2K-PPMS copolymers with different PDL contents.

The surface charges of all micelle samples were slightly negative in PBS solution (0.01M, pH=7.4) (Table 6), which is beneficial for in vivo drug delivery applications of the micelles. It is known that nanoparticles with nearly neutral surface charge (zeta potential between −10 and +10 mV) can decrease their uptake by the reticuloendothelial system (RES) and prolong their circulation time in the blood. The negative surface charges of the micelles could result from the absorption of $HPO_4^{2-}$ and/or $H_2PO_4^-$ anions in PBS by the micelle particles via hydrogen bonding interactions between the anions and the ether groups of PEG shells or the amino groups of PPMS cores. For amphiphilic block copolymer micelles, it DTX drug molecules to the micelles. Possibly because of relatively low stability of the PEG5K-PPMS copolymer micelles as the result of their near neutral surface charges, both drug loading and entrapment efficiency appear lower for these micelle samples (Table 6).

Figures 18A, 18B:
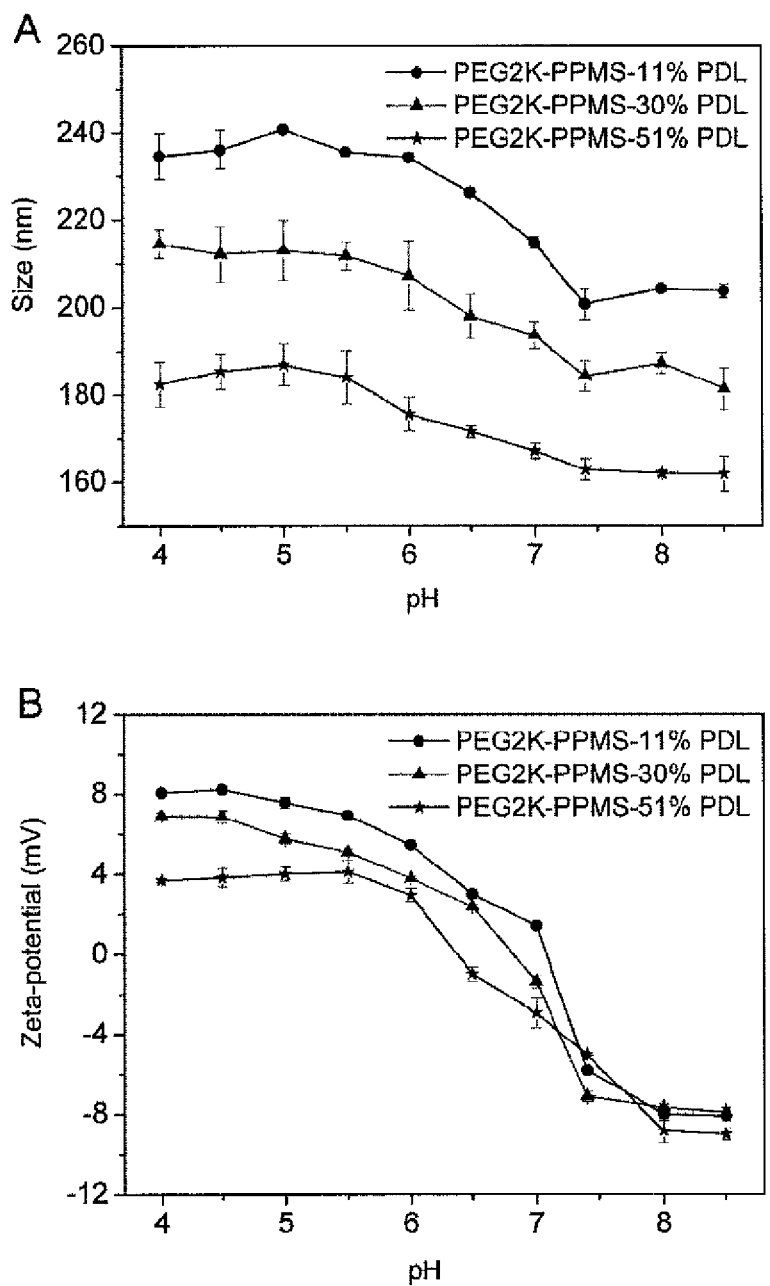
FIGS. 18A and 18B are graphs showing the variation in average size (FIG. 18A) and zeta-potential (FIG. 18B) of blank PEG2K-PPMS copolymer micelles as a function of PBS medium pH.

The size and zeta potential of the micelles were found to change significantly when the pH of the aqueous medium accommodating the micelles was varied. FIG. 18 shows the particle size and zeta potential of blank PEG2K-PPMS copolymer micelles as a function of the aqueous buffer pH. The trends in the size-pH and zeta-pH curves are remarkably similar for the micelles of the three PEG2K-PPMS copolymers with different PDL contents (11%, 30%, and 51%). It is evident that the average size of the micelle samples gradually increases upon decreasing the medium pH from 7.4 to 5.0, and then remains nearly constant when the pH value is below 5.0 (FIG. 18A). This pH-responsive behavior observed for the micelles is anticipated since upon decreasing the pH from 7.4 to 5.0, the PPMS cores of the micelles become protonated and more hydrophilic, thus absorbing more water molecules from the aqueous medium to cause swelling of the micelles. It is assumed that the micelle cores are already fully protonated at pH of 5.0, and as the result, the sizes of the micelles remain fairly constant with further decreasing of the of the pH from 5.0.

The effects of the PDL content in the PEG2K-PPMS copolymers on the magnitude of the micelle size change between 7.4 and 5.0 pH values are also notable. With decreasing PDL content and increasing tertiary amino group content in the copolymer, the capacity of the micelle cores to absorb protons and water molecules is expected to increase. Thus, upon decreasing pH from 7.4 to 5.0, the change in average micelle size was more significant for PEG2K-PPMS-11% PDL (from 200 nm to 234 nm) as compared to PEG2K-PPMS-30% PDL (from 184 nm to 214 nm) and PEG2K-PPMS-51% PDL (from 163 nm to 182 nm) (FIG. 8A).

The zeta potential of the micelles in aqueous medium also exhibits substantial pH-dependence (FIG. 18B). At physiological and alkaline pH (7.4 to 8.5), the surface charges of blank PEG2K-PPMS copolymer micelles were negative, which changed to positive when the pH of the medium decreased to acidic range (4.0-6.0). For example, the micelles of PEG2K-PPMS-11% PDL, PEG2K-PPMS-30% PDL, and PEG2K-PPMS-51% PDL possessed zeta potential values of −5.8, −7.1, −5.1 mV, respectively, at pH of 7.4, which turned to +7.6, +5.8, +4.0 mV, correspondingly, at a lower pH of 5.0. On the basis of the above discussions, this surface charge dependence on pH is attributable to the protonation or deprotonation of the PPMS cores of the micelles at different medium pH. At an alkaline pH (7.4-8.5), most of the amino groups in the micelles presumably are not protonated, and the micelle particles remain negatively charged due to the absorption of $HPO_4^{2-}$ and/or $H_2PO_4^-$ anions in PBS by the micelles. In particular, at pH of 8.5, the zeta-potential values were −8.1 mV, −7.9 mV, −9.0 mV for PEG2K-PPMS-11% PDL, PEG2K-PPMS-30% PDL, and PEG2K-PPMS-51% PDL, respectively (FIG. 18B). Upon decreasing pH from 7.4 to 5.0, the tertiary amino moieties in the micelle PPMS cores become mostly protonated, turning the micelles to positively charged particles.

Consistently, among the three micelle samples, PEG2K-PPMS-11% PDL micelles with the largest capacity to absorb protons displayed the highest zeta potential values at pH of 4.0-5.0, whereas PEG2K-PPMS-51% PDL micelles with the smallest protonation capacity showed the lowest zeta potentials (FIG. 18B). The observed micelle surface charge responses to the medium pH are highly desirable since the negative surface charge of the micelles at physiological pH can alleviate the interaction of the micelles with serum protein in the blood and prolong their in vivo circulation time. On the other hand, the reverse to positive surface charge at the tumor extracellular pH of approximately 6.5 could enhance the uptake of these micelles by target tumor cells.

Example 7

Measurement of Critical Micelle Concentration (CMC) Values of PEG-PPMS Block Copolymers The pH-responsive behavior and CMC values of the copolymer micelles were studied using fluorospectrophotometry. Pyrene was employed as the fluorescence probe. In a typical experiment, an aliquot of pyrene solution in THF was added to tube containers. After the THF solvent evaporated completely, aqueous micelle solutions with various polymer concentrations in predetermined amounts were added to each tube respectively and were vortexed to yield a final pyrene concentration of $6.0 \times 10^{-7}$ M. The solutions were kept at room temperature for 24 h to ensure that pyrene dissolution in aqueous media reaches the equilibrium before measurement. Fluorescence intensities of the pyrene solubilized in the micelle cores were determined by a fluorescence steady-state system with excitation at 334 nm wavelength and emission detection in the range from 350 to 420 nm wavelength. It is known that only at a concentration above the CMC, micelles with a hydrophobic core and a hydrophilic shell are formed. The entrapment of pyrene molecules in the cores of the micelles leads to a higher intensity of the third peak (I3) at 391 nm in the emission spectrum. Therefore, the CMC values can be evaluated by monitoring the intensity of the third peak, which is usually normalized by the intensity of the first emission peak ($I_1$) at 371 nm. In actual practice, for a given PEG-PPMS micelle sample, the I3/I1 intensity ratios are plotted against the logarithm of polymer concentrations, and the CMC value was determined from the intersection of the best-fit lines, which corresponds to the minimum polymer concentration required for formation of stable micelles in the aqueous medium.

Figures 19A, 19B:
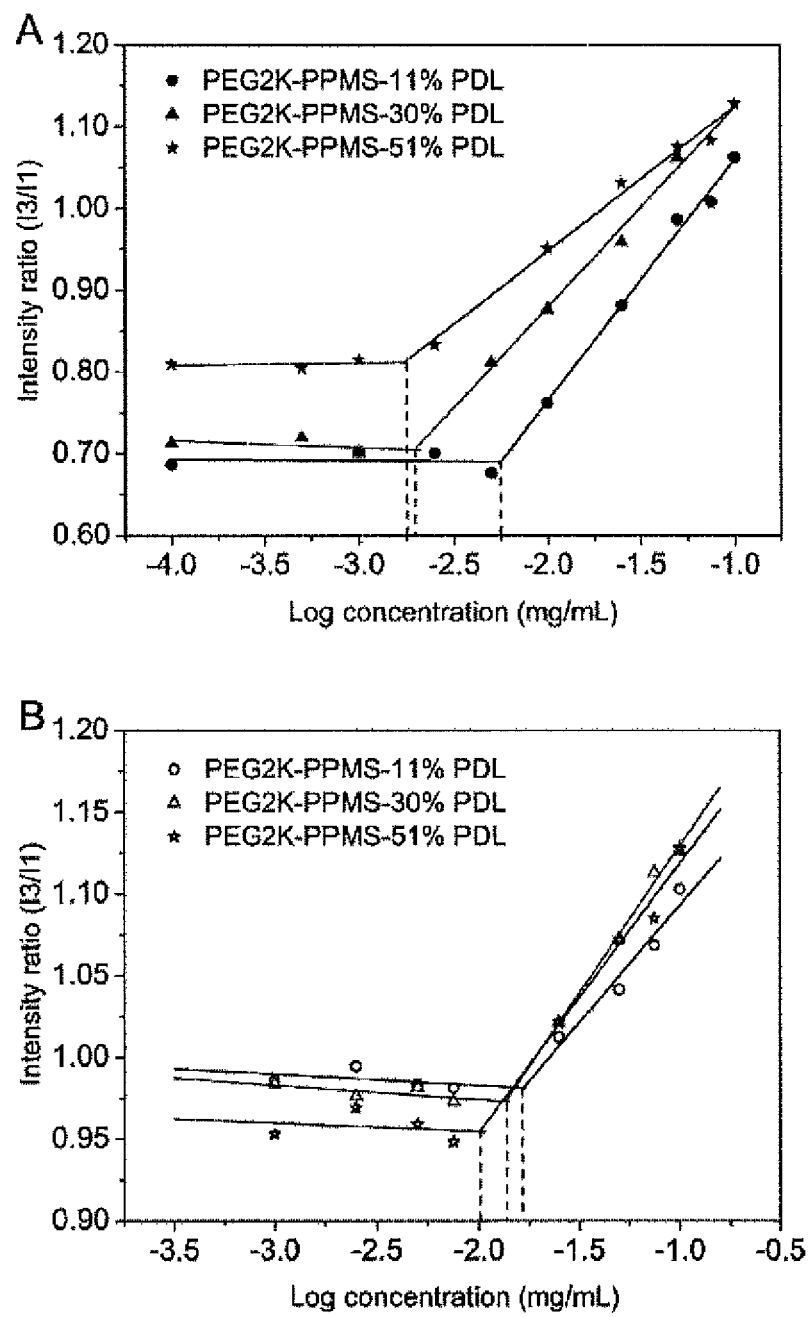
FIGS. 19A and 19B are graphs showing variations of pyrene I3/I1 intensity ratio as a function of logarithm of polymer concentration (mg/mL) for PEG2K-PPMS copolymer micelle samples in two different PBS solutions (0.01 M)

The self-assembling ability and pH-responsive micellization behaviors of PEG2K-PPMS copolymers were investigated in PBS solutions (0.01 M) with pH of 7.4 or 5.0 using fluorospectrophotometry. The fluorescence intensity ratio (I3/I1) of dissolved pyrene as a function of the logarithm of the copolymer concentration is shown in FIG. 19 for the copolymer samples PEG2K-PPMS-11% PDL, PEG2K-PPMS-30% PDL, and PEG2K-PPMS-51% PDL. The cross points of the curves correspond to the CMC values of the polymer samples, above which stable PEG2K-PPMS copolymer micelles are formed and the concentration of entrapped pyrene in the micelles increases with increasing copolymer concentration. The CMC values of PEG2K-PPMS-11% PDL, PEG2K-PPMS-30% PDL, and PEG2K-PPMS-51% PDL were respectively 5.50, 2.04, and 1.95 µg/mL at pH of 7.4, which changed correspondingly to 18.2, 14.1, and 10.7 µg/mL at pH of 5.0. This result can be explained as follows. A higher PDL content in the PPMS chain segments of the PEG2K-PPMS copolymer enhances the hydrophobicity of the micelle inner cores, thus increasing the micelle stability (or decreasing the CMC) in aqueous medium. On the other hand, for a given PEG2K-PPMS copolymer, the stability of the copolymer micelles can also substantially affected by the medium pH. As discussed in the previous section, upon decreasing the medium pH from 7.4 to 5.0, the PPMS cores of the copolymer micelles become protonated and less hydrophobic which would, of course, reduce the stability of the micelles. CMC is an important parameter indicative of micelle stability, and micelles with a low CMC is often required for effective in vivo drug delivery applications since such micelles would not disintegrate upon dilution in the blood stream after intravenous injection. The results of this study indicate that the PEG2K-PPMS copolymer micelles are sufficiently stable carriers for in vivo drug delivery applications.

Example 8

Evaluation of In Vitro Micelle Stability

Micelle solutions at 1 mg/mL concentration were prepared by mixing different PEG-PPMS copolymer micelles with a pre-determined amount of PBS solution (0.01 M, pH=7.4) containing 10 vol % human serum or FBS. The micelle solutions were gently stirred at 37° C. for 144 h. At various time intervals, aliquots were withdrawn from the solutions and were analyzed by DLS to measure the average particle size of the PEG-PPMS copolymer micelles. All measurements were performed in triplicate.

Figures 20A, 20B:
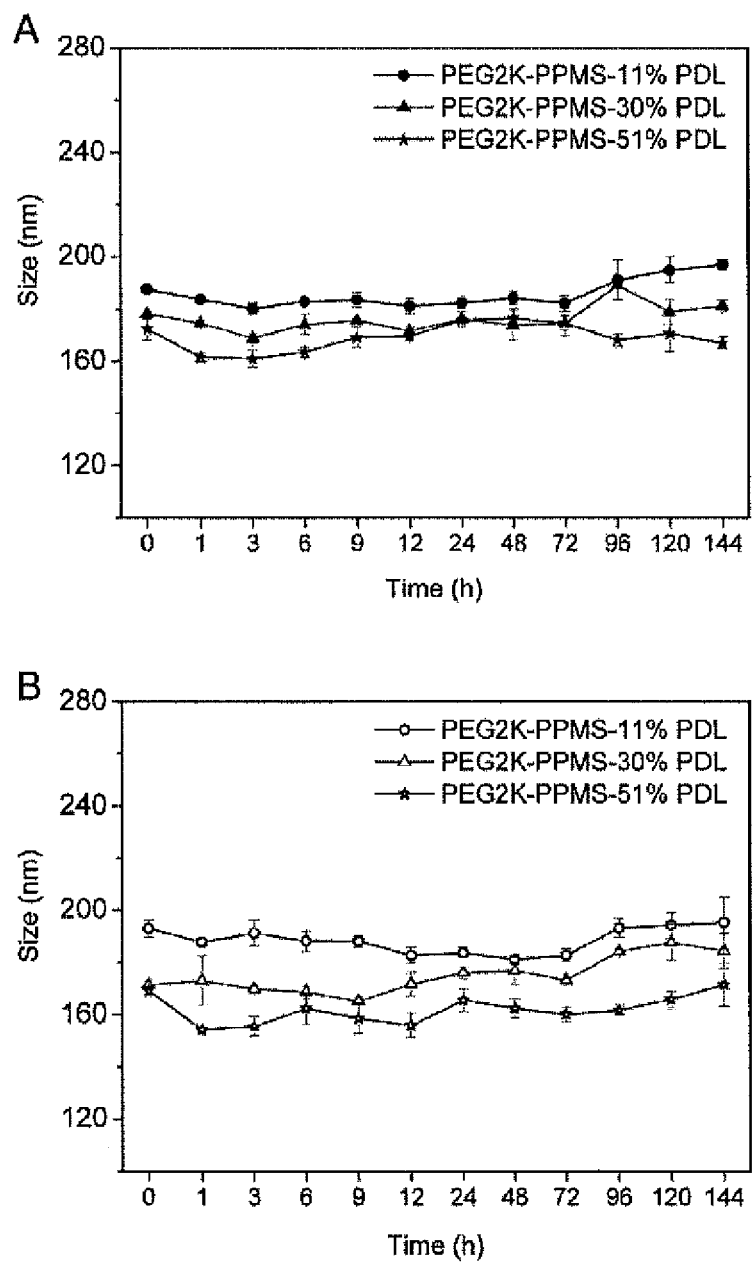
FIGS. 20A and 20B are graphs showing the average micelle size vs. incubation time for PEG2K-PPMS copolymer micelles incubated in PBS solution (0.01 M, pH=7.4) containing (FIG. 20A) 10 vol. % human serum solution and (FIG. 20B) 10 vol. % FBS solution.

In order for micelles to be suitable as carriers to deliver drugs in vivo, the micelle particles must possess sufficient stability in serum-containing aqueous medium. To evaluate the stability of PEG2K-PPMS copolymer micelles under realistic conditions for in vivo drug delivery applications, the blank micelles were incubated with PBS solution (0.01M, pH=7.4) containing either 10 vol % human serum or 10 vol % FBS and the average size of each micelle sample was monitored subsequently for 6 days. As shown in FIG. 20, the micelle sizes of all three PEG2K-PPMS copolymer samples (PEG2K-PPMS-11% PDL, PEG2K-PPMS-30% PDL, and PEG2K-PPMS-51% PDL) remained fairly constant during the whole period of the incubation time. Thus, these PEGylated poly(amine-co-ester) terpolymer micelles can stay intact with minimal interactions with serum proteins in the media, which is critically important for achieving prolonged circulation time of the micelles in the blood to effectively deliver drugs to target tissue/cells.

Example 9

In Vitro DTX Release from the Drug-Loaded PEG-PPMS Micelles

In vitro DTX release studies from the micelles were performed by dialyzing the DTX-encapsulated micelles against PBS (0.01 M) solution with a pH of 5.0 or 7.4.32 Typically, 400 µL of each micelle sample at 40 mg/mL polymer concentration was placed in a dialysis bag (MWCO 3,500 Da) which was then incubated in 10 ml of PBS solution (containing 0.5% Tween 80) at 37° C. and 100 rpm shaking speed. At different time intervals, aliquot samples of 1.0 mL volume were withdrawn from the PBS and the same amount of the fresh buffer was added after each sample withdrawal. Sink condition was maintained throughout the drug release period. The aliquot samples were centrifuged at 12,000 rpm for 5 min and the supernatant was analyzed in triplicate by HPLC to quantify the amount of released DTX as described above.

As discussed above, the physical properties (e.g., size and zeta potential) of the copolymer micelles are dependent on the pH of the medium accommodating the micelles. Therefore, variations in the rate of DTX release from PEG2K-PPMS copolymer micelles at different pH are anticipated. In vitro drug release behaviors of the DTX-encapsulated micelles of PEG2K-PPMS copolymer samples (PEG2K-PPMS-11% PDL, PEG2K-PPMS-30% PDL, and PEG2K-PPMS-51% PDL) were studied in PBS solution at both physiological pH of 7.4 and acidic pH of 5.0.

Figure 21:
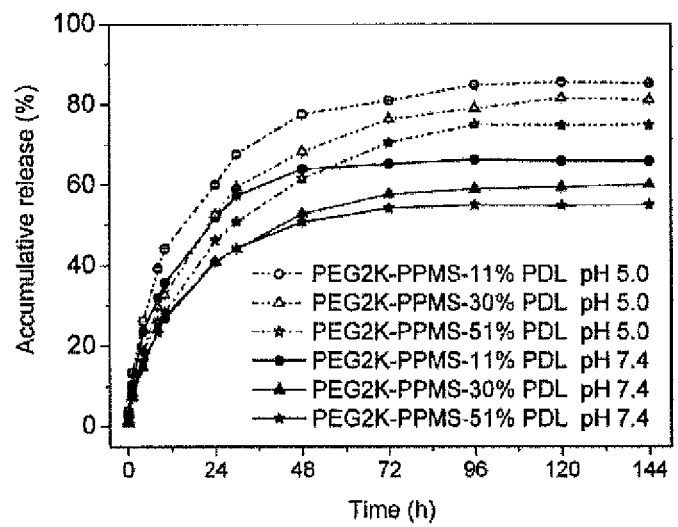
FIG. 21 is a graph showing the in vitro accumulative release of DTX from the drug-loaded PEG2K-PPMS copolymer micelles in PBS solution (0.01 M) with pH of 7.4 or 5.0.

FIG. 21 depicts the accumulative values (in percentage) of DTX released from the micelles during a period of 144 h. In general, the DTX release from all micelle samples followed biphasic release kinetics and indeed exhibited remarkable pH-dependence. The DTX-loaded PEG2K-PPMS copolymer micelles release 25-45% drug rapidly during the initial 12 h, followed by a more gradual release of additional 25-40% drug for the subsequent 132 h (FIG. 21). The influence of the medium pH on the drug release rate is substantial. For example, at the end of the incubation period (144 h), the values of accumulated DTX released from the micelles of PEG2K-PPMS-11% PDL, PEG2K-PPMS-30% PDL, and PEG2K-PPMS-51% PDL copolymers are respectively 66%, 60%, and 55% at physiological pH of 7.4, which increase correspondingly to 85%, 81%, and 75% at acidic pH of 5.0 (FIG. 21). The observed pH-triggered acceleration of DTX release from the PEG2K-PPMS copolymer micelles is consistent with the earlier observation that changing of the medium pH from 7.4 to 5.0 causes significant swelling of the micelles due to the protonation and size increase of the micelle PPMS cores. This pH-triggered micelle size expansion would certainly facilitate the diffusion and release of entrapped DTX from the micelle cores to the aqueous medium. On the other hand, at a given pH, the DTX release rate is presumably controlled by the interactions between the drug and the PPMS matrix in the micelle cores. Since PDL-rich PEG2K-PPMS copolymers are expected to form strong hydrophobic domains in their micelle inner cores to better trap and retain hydrophobic DTX molecules, the drug release from such copolymer micelles should be more gradual and sustained. This hypothesis is supported by the experimental result showing that at both pH of 7.4 and 5.0, the DTX release rate from PEG2K-PPMS copolymer micelles decreases with increasing PDL content in the PPMS chain segments of the copolymer (FIG. 21).

It is known that upon uptake of micelles by tumor cells, the micelle particles are subjected to entrapment in endosomes with pH ranging from 5.5 to 6.0 and in lysosomes with pH ranging from 4.5 to 5.0. As the above results clearly show, these acidic environments would inevitably trigger fast DTX release from PEG2K-PPMS copolymer micelles, thus enhancing the cytotoxicity of the drug-loaded micelles. The amino groups in the copolymers would act as proton sponges to facilitate endosomal escape. Therefore, the pH-responsive properties exhibited by the PEG2K-PPMS copolymer micelles are highly desirable, which render them to be superior carriers for delivery of anticancer drugs.

In Vitro Cellular Uptake Studies

For cellular uptake studies, fluorescent dye coumarin-6 (C6) with low water-solubility was used as a probe to imitate DTX and was encapsulated into PEG-PPMS copolymer micelles using the same protocol for preparation of the DTX-loaded micelles as described in an earlier section. The physicochemical properties of the C6-loaded micelles were characterized. SK-BR-3 cells were seeded into 24-well plates at $2.0 \times 10^5$ cells/well (0.5 mL) and allowed to attach overnight. Free C6 or C6 entrapped in the micelles was then added to each well at 0.2 µg/mL C6 concentration and the cells were incubated at 37° C. for 1 h, 4 h, and 8 h. A same amount of C6 was used to treat each group of the cells. For free C6, a DMSO solution of 1 mg/mL was prepared and was diluted with DMEM to the required concentration. After the incubation, C6-containing media were removed and the cells were thoroughly rinsed twice with cold PBS solution. Subsequently, the treated cells were harvested using trypsin and centrifuged at 1500 rpm for 5 min. Upon removal of the supernatants, the cells were resuspended in 0.3 ml of PBS solution and were analyzed in groups containing 10,000 cells by FACScan (Becton Dickinson, San Jose, Calif.) to measure cellular uptake efficiency of the PEG-PPMS copolymer micelles. Intracellular C6 was excited with an argon laser of 488 nm wavelength at constant intensity and the fluorescence emission was detected at 585 nm wavelength.

Confocal laser scanning microscopy (CLSM) was used to visualize the internalization of C6-loaded micelles by SK-BR-3 cells. Cells were seeded on glass-bottom dishes containing culture medium and were incubated overnight at 37° C. C6-loaded micelles were added to each dish at a C6 concentration of 0.2 µg/mL and the cells were incubated for another 4 h at 37° C. Subsequently, the medium was removed and the cells were washed twice with PBS solution. After staining the cell nuclei with Hochest 33342 (10 µg/mL) and the acidic late endosomes and lysosomes with LysoTracker Red (75 nM), the intracellular distribution of C6 was observed by CLSM using a Lecia TCS SP5 Spectral Confocal Microscope with a 63× objective and a diode laser. The excitation wavelength for detecting C6, Hochest 33342, and LysoTracker Red was 467 nm, 405 nm, and 577 nm, respectively.

The cellular uptake efficiency of the drug-loaded PEG2K-PPMS copolymer micelles was investigated with both flow cytometry and confocal laser scanning microscopy (CLSM). To simplify the experimental processes, coumarin-6 (C6, a hydrophobic fluorescent marker) was employed instead of DTX and was encapsulated in PEG2K-PPMS copolymer micelles using the same method for preparing the DTX-loaded micelles as described in the Experimental Section. Because of its substantially low solubility in water, C6 is often considered as a non-releasing agent in nanoparticle samples, which is idea for study on cellular uptake of the micelle particles. To ensure that the C6-encapsulated PEG2K-PPMS copolymer micelles are comparable to their DTX-loaded micelle counterparts, the physicochemical properties of C6-loaded micelles were characterized. The results showed that for a given PEG2K-PPMS copolymer, the average size, PDI, and zeta-potential were very similar between the C6-loaded micelles and the DTX-loaded micelles. For example, the mean sizes of the C6-loaded micelles were respectively 194±4 nm, 171±5 nm, and 210±8 nm, and the C6 entrapment efficiency of the micelles were correspondingly 81% (±1.3%), 96% (42.0%) and 99% (±1.5%) for the copolymers PEG2K-PPMS-11% PDL, PEG2K-PPMS-30% PDL, and PEG2K-PPMS-51% PDL. The accumulative values of C6 release from all three micelle samples were less than 1% over a period of 10 h incubation time.

Figure 22:
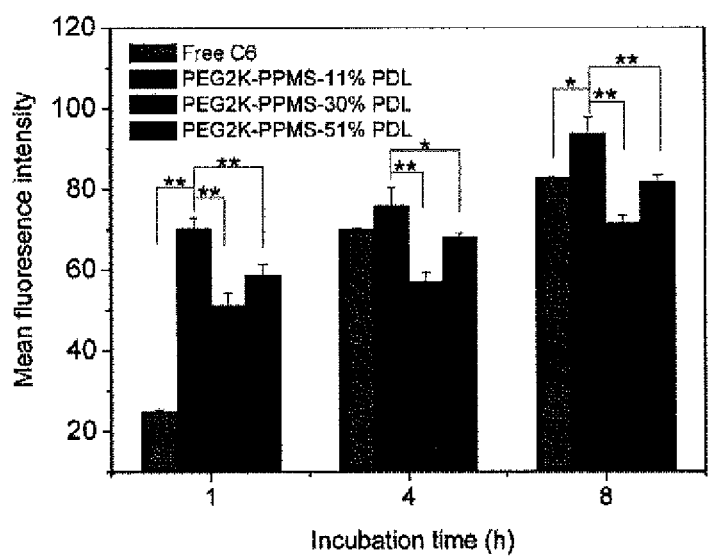
FIG. 22 is a graph showing the relative uptake efficiency of free C6 and C6-loaded micelles of PEG2K-PPMS copolymers with various PDL contents by SK-BR-3 cells at C6 concentration of 0.2 μg/mL. The intracellular C6 MFI values were measured by flow cytometry after 1-8 h incubation and are given as mean SD (n=3). *$p<0.05$ and **$p<0.01$ compared with PEG2K-PPMS-11% PDL.

Flow cytometry analysis was performed to investigate cellular uptake efficiency of the C6-loaded PEG2K-PPMS copolymer micelles at different time intervals. FIG. 22 shows the mean fluorescence intensity (MFI) values of SK-BR-3 cells incubated with free C6 or C6-loaded micelles at 37° C. for up to 8 h. It is evident that the cellular uptake process is time-dependent with an increasing number of the micelles being absorbed by the cells at an extended time. Among the three micelle samples, the uptake rate of the micelles by SK-BR-3 cells (measured by MFI of the cells) follows the order: PEG2K-PPMS-30% PDL copolymer micelles <PEG2K-PPMS-51% PDL copolymer micelles <PEG2K-PPMS-11% PDL copolymer micelles (FIG. 22). At a given incubation time, the MFI value for the cell group treated with PEG2K-PPMS-11% PDL copolymer micelles is statistically higher than that of the cells treated with free C6, PEG2K-PPMS-30% PDL copolymer micelles, or PEG2K-PPMS-51% PDL copolymer micelles. This result was confirmed by the CLSM images of SK-BR-3 cells after absorbing C6-loaded PEG2K-PPMS copolymer micelles. When treated with each of the three PEG2K-PPMS micelle samples containing same amount of C6, the cell group incubated with C6-encapsulated PEG2K-PPMS-11% PDL copolymer micelles displayed strongest green fluorescence intensity. The cellular uptake experiments also indicate that the PEG2K-PPMS copolymer micelles can be quickly absorbed by the cells since after 1 h short incubation time, the cell groups treated with each of the three micelle samples exhibited substantially higher MFI values than the cells treated with free C6 (FIG. 22).

To clarify whether or not drug-loaded PEG2K-PPMS copolymer micelles can escape from endosomes and lysosomes after cellular uptake, the locations of C6-loaded micelles in SK-BR-3 cells relative to the positions of acidic endosomes and lysosomes were visualized by staining the endosomes and lysosomes with LysoTracker Red and were observed with CLSM. The C6-loaded PEG2K-PPMS copolymer micelles were internalized by the cells and distributed all over the cytoplasm with only few of them found to co-localize (thus possibly still trapped/associated) with the LysoTracker Red-stained organelles after 4 h incubation. This result shows that the PEG2K-PPMS copolymer micelles are capable of escaping from the endosomes and lysosomes likely due to the good buffer capability of the tertiary amine groups in the copolymers which act as proton sponges.

The cellular uptake efficiency of the PEG2K-PPMS copolymer micelles could be affected by several factors, including the particle size, particle surface properties (e.g., surface charge and hydrophobicity), and polymer composition. As discussed earlier, the average particle sizes of the three C6-loaded micelle samples are around 200 nm and comparable. Thus, the observed variations in cellular uptake efficiency are possibly attributed to the differences in the micelles' surface properties and their polymer composition.

Example 10

In Vitro Cytotoxicity Study

The in vitro cytotoxicity of free DTX, blank PEG-PPMS copolymer micelles and DTX-loaded copolymer micelles were tested against SK-BR-3 cells using the standard MTT assay. To evaluate the pH-responsive characteristics of the DTX-loaded micelles, the cytotoxicity experiments were performed at different pH values as follows. The cells were seeded in a 96-well plate at a density of 2,500 cells per well in 100 μL of RPMI-1640 medium with 10% FBS, and were kept at 37° C. in 5% $CO_2$ atmosphere. After allowing the cells to adhere overnight, 100 μL of the medium containing different amount of DTX (either free drug or in PEG-PPMS copolymer micelles) was added to each well. The medium pH was adjusted with 0.1 M HCl or 0.1 M NaOH to a desired value (7.4 or 6.5) right before the treatment. When blank PEG-PPMS copolymer micelles were used instead of the DTX-loaded micelles, the concentration of both micelles was kept same. After 48 h of incubation, the medium was removed and the cells were rinsed twice with PBS solution. Subsequently, 100 μL of the fresh medium and 20 μL of PBS containing 5 mg/mL MIT were added to each well, and the plate was incubated for additional 4 h. After removal of the medium in each well, 150 μL of DMSO was added to dissolve the formazan salt crystals and the absorbance of each well at 570 nm wavelength was measured using a microplate reader (Bio Tek Synergy4). All assays were carried out in triplicate and were repeated at least twice. Cell viability was calculated as the value in percentage of (absorbance of the cells treated)/(absorbance of the cells cultured without treatment).

Figure 23:
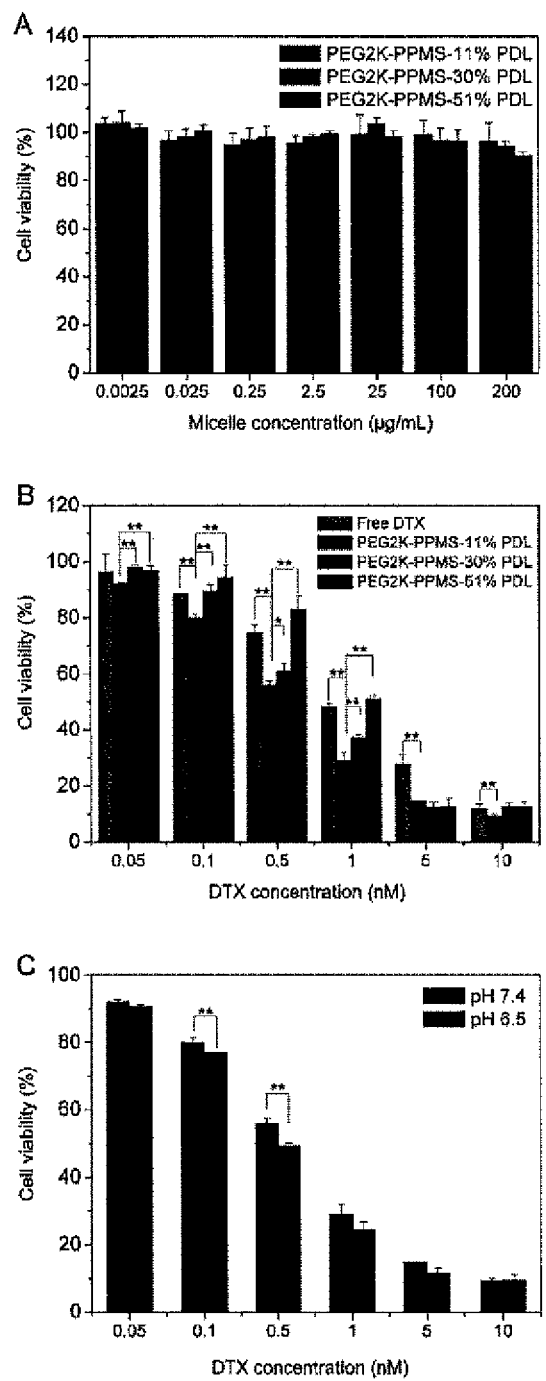
FIGS. 23A-23C are graphs showing the viabilities of SK-BR-3 cells after incubation for 48 h with various doses of PEG2K-PPMS copolymer micelles.

The cytotoxicity of blank PEG2K-PPMS copolymer micelles, DTX-loaded PEG2K-PPMS copolymer micelles, and free DTX was evaluated on SK-BR-3 cells at pH of 7.4 using the MIT assay, and the results are shown in FIG. 23. The blank micelles exhibited no obvious cytotoxicity on SK-BR-3 cells as the cell viabilities of all treated cell groups were over 90% (FIG. 23A). For example, after treatment with the micelles of PEG2K-PPMS-11% PDL, PEG2K-PPMS-30% PDL, and PEG2K-PPMS-51% PDL copolymers at concentration as high as 200 μg/mL, the three treated cell groups had respectively 97%, 94%, and 90% of the cells remaining viable. FIG. 23B depicts the cytotoxicity of the DTX-loaded micelles and free DTX incubated with SK-BR-3 cells for 48 h. As expected, the cell viability decreases with increasing concentration of DTX either in the form of the free drug or in the form of the drug encapsulated in the micelles. To quantify the in vitro efficacy of these micelle formulations, IC50 values for DTX-loaded micelles of copolymers PEG2K-PPMS-11% PDL, PEG2K-PPMS-30% PDL, and PEG2K-PPMS-51% PDL were calculated to be 0.57 nM, 0.83 nM, and 1.42 nM, respectively. In comparison, the IC50 value for free DTX was found to be 1.27 nM. IC50 is defined as the drug concentration of a specific formulation which is required to kill 50% of cells after they are incubated with the drug for a designated time period (48 h). Thus, except the PEG2K-PPMS-51% PDL copolymer micelles, both DTX-loaded PEG2K-PPMS-11% PDL copolymer micelles and DTX-loaded PEG2K-PPMS-30% PDL copolymer micelles possess significantly higher cytotoxicity against SK-BR-3 cells than free DTX. The exceptionally high efficacy observed for DTX-loaded PEG2K-PPMS-11% PDL copolymer micelles is likely attributed to fast cellular uptake of the micelles (FIG. 22) and anticipated rapid intracellular DTX release from the micelles upon entrapment of the micelle particles in acidic endosomes/lysosomes (FIG. 21). The rate of DTX release from the micelles, particularly pH-triggered acceleration of the drug release, appears to play a more important role than the cellular uptake in influencing the cytotoxicity of the DTX-loaded micelles. Thus, although the cellular uptake is faster for DTX-loaded PEG2K-PPMS-51% PDL copolymer micelles vs. DTX-loaded PEG2K-PPMS-30% PDL copolymer micelles (FIG. 22), the latter micelles release the drug at a higher rate to exert higher cytotoxicity toward SK-BR-3 cells (FIG. 21).

To elucidate how the cell viability is affected by the release and cellular uptake of the drug in an acidic tumor extracellular matrix environment, the cytotoxicity of the DTX-loaded PEG2K-PPMS copolymer micelles toward SK-BR-3 cells were also investigated at pH of 6.5. The obtained IC50 values at pH of 6.5 for free DTX and DTX-loaded micelles of copolymers PEG2K-PPMS-11% PDL, PEG2K-PPMS-30% PDL, and PEG2K-PPMS-51% PDL were correspondingly 1.34, 0.45, 0.58, and 1.20 nM. Thus, all three micelle samples exhibited decreased IC50 values and enhanced cytotoxicity upon changing of the medium pH from 7.4 to 6.5. This acid-promoted, cytotoxicity enhancement for the PEG2K-PPMS copolymer micelles appears to be independent on the concentration of the encapsulated drug. For example, at various doses (0.05-10 nM) of DTX encapsulated in PEG2K-PPMS-11% PDL copolymer micelles, the viability of the SK-BR-3 cells treated at acidic pH of 6.5 was always lower than that of the cells treated at pH of 7.4 (FIG. 23C). This acid-enhanced cytotoxicity presumably results from increased cellular uptake efficiency of the micelles upon changing the medium pH from slightly basic (pH of 7.4) to mildly acidic (pH of 5.0-6.5). As shown in FIG. 18B, when the medium pH was adjusted from 7.4 to 6.5, the surface charges of the PEG2K-PPMS-11% PDL, PEG2K-PPMS-30% PDL, and PEG2K-PPMS-51% PDL copolymer micelles changed from negative values to near neutral or positive charges, which should promote binding of the micelles with the cell membrane and accelerate the cellular uptake of the micelles at the lower pH.

Example 11

Erythrocyte Agglutination and Hemolysis

The erythrocyte agglutination and hemolytic activity of PEG-PPMS copolymer micelles were investigated using literature procedures. Human blood was centrifuged at 1000 rpm for 5 min to isolate erythrocytes (RBC). The obtained erythrocytes were washed in isotonic PBS (0.01 M, pH=7.4) until the supernatant was clear. The cells were then diluted in PBS to decrease the cell density to $3 \times 10^7$ cells/mL. This erythrocyte solution was always freshly prepared and was used within 24 h after collection. Blank PEG-PPMS copolymer micelle solutions with various polymer concentrations were added to the erythrocytes and the resultant mixtures were incubated at 37° C. for 2 h. Triton X-100 (0.1%, w/v) and isotonic PBS were used as positive control and negative control, respectively. At the end of the incubation period, the cell/polymer mixed solutions were transferred to a 24-well plate and were observed with an optical microscope. Meanwhile, the absorbance at 413 nm was measured for the supernatant of each sample using a microplate reader.

The relative hemolytic activity (%) is calculated using the following equation:

$$\text{Hemolysis (\%)} = \frac{A_{Sample} - A_{PBS}}{A_{Triton} - A_{PBS}} \times 100\%$$

where $A_{sample}$, $A_{PBS}$, $A_{Triton}$ represent the absorbance intensity values of the supernatants from RBC treated with PEG-PPMS copolymer micelles, PBS, and Triton X-100, respectively.

Figure 24:
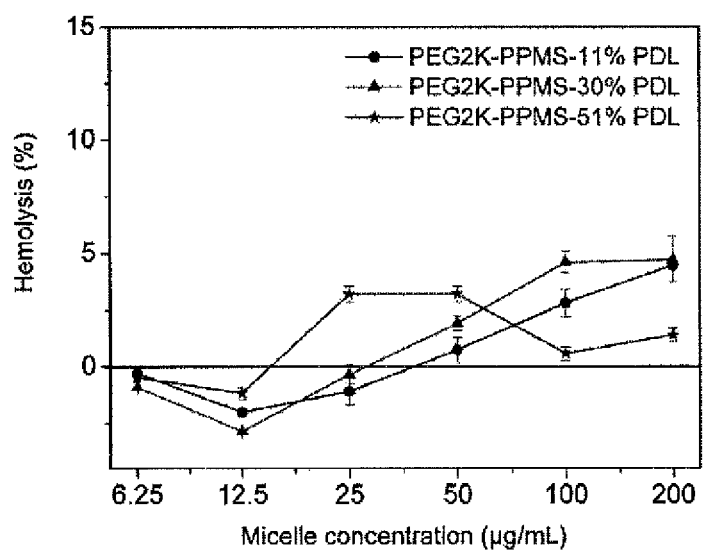
FIG. 24 is a graph showing the hemolytic activity of blank PEG2K-PPMS copolymer micelles. Triton X-100 and PBS were used as the positive and negative controls, respectively. Data are given as mean±SD (n=3).

Hemolysis and agglutination behaviors are two major biocompatibility issues that frequently occur during in vivo application of new drug formulations. To verify that the PEG2K-PPMS copolymer micelles are biocompatible, the blank micelles at various concentrations were incubated with erythrocytes to evaluate the tendency of the copolymers to induce hemolysis and agglutination. Erythrocytes treated with PEG2K-PPMS-11% PDL, PEG2K-PPMS-30% PDL, and PEG2K-PPMS-51% PDL copolymer micelles, along with PBS solution, showed no agglutination and the erythrocytes retained the integrity of double-concave disc shape. The quantitative hemolysis results on the copolymer micelles are illustrated in FIG. 24. Although the hemolysis activity (percentage ratio vs. Triton X-100 activity) of the three micelle samples increased slightly with increasing micelle concentration, the hemolysis ratios for PEG2K-PPMS-11% PDL, PEG2K-PPMS-30% PDL, and PEG2K-PPMS-51% PDL copolymer micelles were respectively 4.5%, 4.6%, and 3.2% even at the highest polymer concentration of 200 μg/ml. These hemolysis values are substantially lower than the maximum nonhemolytic value (8%) set by ASTM F756-08 standard test method. According to the method, samples with a hemolysis ratio below 8% are considered nonhemolytic. Thus, the PEG-PPMS copolymers can be defined as nonhemolytic with minimal tendency to cause agglutination.

A series of PEGylated poly(amine-co-ester) terpolymers were successfully synthesized in one step via lipase-catalyzed copolymerization of PDL, DES, and MDEA comonomers in presence of poly(ethylene glycol) methyl ether as a chain-terminating agent. The resultant amphiphilic PEG-PPMS block copolymers consisted of hydrophilic PEG chain segments with molecular weight (Mn) ranging from 2000 Da to 5000 Da and hydrophobic random PPMS copolymer chain segments with PDL content ranging from 10 to 50 mol %. TGA analysis shows that the block copolymers are thermally stable up to 300° C. with the fastest degradation taking place at 408-424° C. Consistent with the copolymer block structures, a major melting temperature at 43-54° C. due to PEG crystallites was observed for all PEG-PPMS copolymers, and an additional weak melting event was detected for the PDL-rich copolymers (e.g., PEG2K-PPMS-40% PDL, PEG2K-PPMS-51% PDL, PEG5K-PPMS-41% PDL, and PEG5K-PPMS-50% PDL) possibly due to the presence of second crystallites formed by PDL-rich PPMS chain segments.

Upon dissolution in water, the PEG2K-PPMS copolymers with 42 wt % PEG content readily formed micelles with average particle size in the range between 160 and 190 nm, which were stable at physiological pH of 7.4 in presence of serum proteins. The PEG2K-PPMS copolymers possessed high blood compatibility and exhibited minimal activity to induce hemolysis and agglutination. The copolymer micelles are pH-responsive: with decreasing the medium pH from 7.4 to 5.0, the sizes of the micelles increased significantly while the micelle surface charges reversed from negative charges to positive charges. Correspondingly, DTX-encapsulated PEG2K-PPMS copolymer micelles showed gradual sustained drug release at physiological pH of 7.4, but remarkably accelerated DTX release at acidic pH of 5.0. Cellular uptake study revealed that the drug-loaded micelle particles were readily absorbed by SK-BR-3 cells. CLSM experiments indicated that the micelles were able to escape from entrapment by endosomes and lysosomes after the cellular uptake. Because of these desirable properties, DTX-loaded micelles of PEG2K-PPMS copolymers (e.g., PEG2K-PPMS-11% PDL and PEG2K-PPMS-30% PDL) with low PDL content, high protonation capability, and fast drug release at an acidic pH exert substantially higher potency against SK-BR-3 cancer cells than free DTX drug. These results demonstrate that PEG2K-PPMS copolymer micelles have great potential to serve as pH-responsive nano-carriers for controlled release delivery of DTX to treat cancers.

We claim:
1. A polymer of formula I:

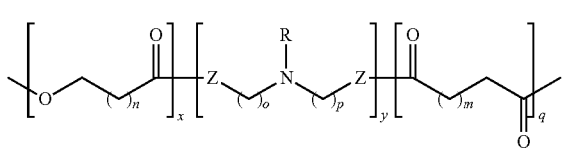

Formula I wherein each occurrence of n is an integer from 1-30, each occurrence of m, o, and p are independently integers from 1-20, each occurrence of x, y, and q are independently integers from 1-1000, and Z is O or NR', wherein R' is hydrogen, substituted or unsubstituted alkyl, or substituted or unsubstituted aryl.

2. The polymer of claim 1, wherein n is 4, 10, 13, or 14.
3. The polymer of claim 2, wherein m is 5, 6, or 7.
4. The polymer of claim 1, wherein R is substituted or unsubstituted alkyl.
5. The polymer of claim 4, wherein alkyl is methyl, ethyl, propyl, n-butyl, or t-butyl.
6. The polymer of claim 4, wherein R is substituted or unsubstituted aryl.
7. The polymer of claim 6, wherein aryl is phenyl.
8. The polymer of claim 1, wherein the molar ratio of the monomers is from about 10:90:90 to about 90:10:10.
9. The polymer of claim 1, wherein the weight average molecular weight, as measured by gel permeation chromatography using narrow polydispersity polystyrene standards, is from about 10,000 Daltons to about 50,000 Daltons.
10. A particle comprising the polymer of claim 1 and one or more therapeutic, prophylactic, or diagnostic agents.
11. The particle of claim 10, wherein the one or agents is a small molecule, a macromolecule, or combinations thereof.
12. The polymer of claim 9, wherein the weight average molecular weight, as measured by gel permeation chromatography using narrow polydispersity polystyrene standards, is from about 15,000 Daltons to about 40,000 Daltons.
13. The particle of claim 11, wherein the macromolecule is a polynucleotide.
14. The particle of claim 10 coated with an agent that reduce the surface charge of the nanoparticle at physiological a pH.
15. The particle of claim 14 wherein the surface charge of the coated nanoparticle is neutral or negative at physiological pH.
16. The particle of claim 14 wherein the agent comprises a polypeptide comprising a series of negatively charged amino acids, and wherein the polypeptide has a net negative charge at physiological pH.
17. The particle of claim 16 wherein the series of negatively charged amino acids comprise six glutamic acids or six aspartic acids.
18. The particle of claim 16 wherein the polypeptide further comprises a cell targeting signal or cell targeting domain that enhances targeting of the nanoparticle to a cell-type or cell-state.
19. The particle of claim 18 wherein the cell targeting domain enhances targeting of the nanoparticle to cancer cells.
20. The particle of claim 19 wherein the cell targeting domain is selected from the group consisting of RGD, R/KxxR/K where "x" is any amino acid, GdPdLGdVdRG (SEQ ID NO:5), and ASGPR (SEQ ID NO:6).

21. The particle of claim 16 wherein the stretch of negatively charged amino acids and the cell targeting domain are linked by a linker polypeptide.
22. The particle of claim 21 wherein the linker polypeptide comprises 5 or more glycines.
23. The particle of claim 10 wherein the particle has a mean diameter of between about 150 nm and about 275 nm.
24. The particle claim 10 wherein the weight:weight ratio of polymer:agent is between about 25:1 and about 250:1.
25. The particle of claim 13 wherein the polynucleotide comprises a coding sequence that encodes a protein.
26. The particle of claim 25 wherein the coding sequence is operably linked to an expression control sequence.
27. The particle of claim 13 wherein the polynucleotide is an expression vector.
28. The particle of claim 27, wherein the polynucleotide is a functional nucleic acid, or an expression vector comprising sequence encoding a functional nucleic acid operably linked to an expression control sequence.
29. The particle of claim 28 wherein the functional nucleic acid is selected from the group consisting of antisense molecules, siRNA, miRNA, aptamers, ribozymes, triplex forming molecules, RNAi, and external guide sequences.
30. A pharmaceutical composition comprising the particles of claim 10 and a pharmaceutically acceptable carrier.
31. A method of administering one or more therapeutic, diagnostic, or prophylactic agents, or combinations thereof in vivo, comprising administering the composition of claim 30.
32. A method of transfecting cells comprising contacting cells with the particle of claim 10.
33. The method of claim 32 wherein the particles are administered to a subject in an effective amount to treat a disease or condition.
34. The method of claim 33 wherein the disease or condition is selected from the group consisting of mitochondrial diseases, infectious diseases, cancers, metabolic disorders, autoimmune diseases, inflammatory disorders, and age-related disorders.
35. The method of claim 31 wherein the route of administering the particles is selected from the group consisting of enteral, parenteral, transdermal, and transmucosal.
36. The method of claim 35 wherein the composition is administered systemically.
37. The method of claim 36 wherein the composition is administered locally.
38. The method of claim 32 wherein the contacting occurs in vitro.
39. The method of claim 38 wherein the cells are primary cells or cells from a cell line.
40. The method of claim 39 wherein the primary cells are harvested from a subject.
41. The method of claim 40 further comprising returning the cells to the subject.
42. The method of claim 41 wherein the cells are used to treat a disease or condition selected from the group consisting of mitochondrial diseases, infectious diseases, cancers, metabolic disorders, autoimmune diseases, inflammatory disorders, and age-related disorders.
43. The method of claim 32, wherein the particle is less toxic, more efficient at transfecting polynucleotides, or a combination thereof when compared to a control.
44. The method of claim 43 wherein the control is cells transfected with LIPOFECTAMINE 2000 or polyethylenimine (PEI).

* * * * *

```
                        SEQUENCE LISTING

<160> NUMBER OF SEQ ID NOS: 6

<210> SEQ ID NO 1
<211> LENGTH: 26
<212> TYPE: PRT
<213> ORGANISM: Artificial Sequence
<220> FEATURE:
<223> OTHER INFORMATION: Synthetic Construct

<400> SEQUENCE: 1

Glu Glu Glu Glu Glu Glu Glu Glu Glu Glu Glu Glu Glu Glu Glu Glu
1               5                   10                  15

Gly Gly Gly Gly Gly Gly Arg Gly Asp Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Construct

<400> SEQUENCE: 2

Arg Gly Asp Lys Gly Gly Gly Gly Gly Gly Glu Glu Glu Glu Glu Glu
1               5                   10                  15

Glu Glu Glu Glu Glu Glu Glu Glu Glu Glu
            20                  25

<210> SEQ ID NO 3
<211> LENGTH: 22
<212> TYPE: PRT
<213> ORGANISM: Artificial Sequence
<220> FEATURE:
<223> OTHER INFORMATION: Synthetic Construct

<400> SEQUENCE: 3

Gly Gly Gly Gly Gly Gly Glu Glu Glu Glu Glu Glu Glu Glu Glu Glu
1               5                   10                  15

Glu Glu Glu Glu Glu Glu
            20

<210> SEQ ID NO 4
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D or L amino acid
```

```
<220> FEATURE:
<221> NAME/KEY: MISC_FEATURE
<222> LOCATION: (3)..(3)
<223> OTHER INFORMATION: D or L amino acid
<220> FEATURE:
<221> NAME/KEY: MISC_FEATURE
<222> LOCATION: (5)..(5)
<223> OTHER INFORMATION: D or L amino acid
<220> FEATURE:
<221> NAME/KEY: MISC_FEATURE
<222> LOCATION: (6)..(6)
<223> OTHER INFORMATION: D or L amino acid
<220> FEATURE:
<221> NAME/KEY: MOD_RES
<222> LOCATION: (29)..(29)
<223> OTHER INFORMATION: AMIDATION

<400> SEQUENCE: 4

Gly Pro Leu Gly Val Arg Gly Gly Gly Gly Gly Gly Gly Glu Glu Glu
1               5                   10                  15

Glu Glu Glu Glu Glu Glu Glu Glu Glu Glu Glu Glu Glu
            20                  25

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D or L amino acid
<220> FEATURE:
<221> NAME/KEY: MISC_FEATURE
<222> LOCATION: (3)..(3)
<223> OTHER INFORMATION: D or L amino acid
<220> FEATURE:
<221> NAME/KEY: MISC_FEATURE
<222> LOCATION: (5)..(5)
<223> OTHER INFORMATION: D or L amino acid
<220> FEATURE:
<221> NAME/KEY: MISC_FEATURE
<222> LOCATION: (6)..(6)
<223> OTHER INFORMATION: D or L amino acid

<400> SEQUENCE: 5

Gly Pro Leu Gly Val Arg Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Ala Ser Gly Pro Arg
1               5
```